(12) United States Patent
Mazmanian et al.

(10) Patent No.: US 12,329,786 B2
(45) Date of Patent: *Jun. 17, 2025

(54) REGULATE GUT MICROBIOTA TO TREAT NEURODEGENERATIVE DISORDERS

(71) Applicant: California Institute of Technology, Pasadena, CA (US)

(72) Inventors: Sarkis K. Mazmanian, Porter Ranch, CA (US); Timothy R. Sampson, Los Angeles, CA (US)

(73) Assignee: CALIFORNIA INSITUTE OF TECHNOLOGY, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/335,889

(22) Filed: Jun. 15, 2023

(65) Prior Publication Data

US 2024/0000862 A1 Jan. 4, 2024

Related U.S. Application Data

(63) Continuation of application No. 16/302,321, filed as application No. PCT/US2017/033881 on May 22, 2017, now Pat. No. 11,707,493.

(60) Provisional application No. 62/443,952, filed on Jan. 9, 2017, provisional application No. 62/370,578, filed on Aug. 3, 2016, provisional application No. 62/340,408, filed on May 23, 2016.

(51) Int. Cl.
| | |
|---|---|
| *A61K 35/741* | (2015.01) |
| *A61K 38/14* | (2006.01) |
| *C12Q 1/6883* | (2018.01) |
| *C12Q 1/689* | (2018.01) |
| *G01N 33/569* | (2006.01) |

(52) U.S. Cl.
CPC ............ *A61K 35/741* (2013.01); *A61K 38/14* (2013.01); *C12Q 1/6883* (2013.01); *C12Q 1/689* (2013.01); *G01N 33/56911* (2013.01); *G01N 2800/2835* (2013.01)

(58) Field of Classification Search
CPC ....... A61K 35/741; A61K 38/14; A61P 25/00; A61P 29/00
See application file for complete search history.

(56) References Cited

U.S. PATENT DOCUMENTS

| | | | |
|---|---|---|---|
| 5,443,826 A | 8/1995 | Brody | |
| 5,951,977 A | 9/1999 | Nisbet et al. | |
| 7,041,814 B1 | 5/2006 | Weinstock | |
| 9,452,189 B2 | 9/2016 | Mazmanian et al. | |
| 11,147,792 B2 | 10/2021 | Sampson | |
| 11,707,493 B2 * | 7/2023 | Mazmanian | A61K 38/14 424/93.4 |
| 2002/0013270 A1 | 1/2002 | Bolte | |
| 2004/0005304 A1 | 1/2004 | Brudnak | |
| 2004/0028689 A1 | 2/2004 | Borody | |
| 2004/0137092 A1 | 7/2004 | Castillo et al. | |
| 2004/0170617 A1 | 9/2004 | Finegold | |
| 2006/0167057 A1 | 7/2006 | Kong et al. | |
| 2007/0116779 A1 | 5/2007 | Mazzio | |
| 2008/0015247 A1 | 1/2008 | Lines | |
| 2008/0153114 A1 | 6/2008 | Fleming et al. | |
| 2009/0118257 A1 | 5/2009 | Jankowski et al. | |
| 2009/0156471 A1 | 6/2009 | Gazit et al. | |
| 2010/0040558 A1 | 2/2010 | Shytle et al. | |
| 2011/0081320 A1 | 4/2011 | Westall et al. | |
| 2011/0118135 A1 | 5/2011 | State et al. | |
| 2012/0087895 A1 | 4/2012 | Mazmanian et al. | |
| 2012/0088841 A1 | 4/2012 | Majeed et al. | |
| 2012/0190055 A1 | 7/2012 | Cezar et al. | |
| 2012/0207726 A1 | 8/2012 | Lipkin et al. | |
| 2012/0237482 A1 | 9/2012 | Rodriguez | |
| 2012/0252775 A1 | 10/2012 | Finegold | |
| 2012/0309701 A1 | 12/2012 | Janetka et al. | |
| 2013/0115257 A1 | 5/2013 | Gysemans et al. | |
| 2013/0303397 A1 | 11/2013 | Vebø et al. | |
| 2014/0065132 A1 | 3/2014 | Hsiao et al. | |
| 2015/0152484 A1 | 6/2015 | Krajmalnik-Brown et al. | |
| 2015/0259728 A1 | 9/2015 | Cutliffe et al. | |
| 2016/0040215 A1 | 2/2016 | Henn et al. | |
| 2016/0058808 A1 | 3/2016 | Hsiao et al. | |
| 2016/0120916 A1 | 5/2016 | Hsaio et al. | |
| 2016/0120917 A1 | 5/2016 | Bailey et al. | |
| 2016/0120920 A1 | 5/2016 | Hsiao et al. | |

(Continued)

FOREIGN PATENT DOCUMENTS

| | | |
|---|---|---|
| WO | WO 92/018529 | 10/1992 |
| WO | WO 96/011014 | 4/1996 |

(Continued)

OTHER PUBLICATIONS

Adams et al. (2011). Gastrointestinal flora and gastrointestinal status in children with autism—comparisons to typical children and correlation with autism severity. BMC Gastroenterol 11, 22.
Agrawal et al, 2015, Molecular diagnostics of neurodegenerative disorders, Front Mol Biosciences, 2:1-10.
Aho et al., 2021, Relationships of gut microbiota, short-chain fatty acids, inflammation, and the gut barrier in Parkinson's disease, Mol Neurodegeneration, 16(6):1-14.
Al-Asmakh et al. (2012). Gut microbial communities modulating brain development and function. Gut Microbes 3, 366-373.

(Continued)

*Primary Examiner* — Ruth A Davis
(74) *Attorney, Agent, or Firm* — Knobbe Martens Olson & Bear LLP

(57) ABSTRACT

Disclosed herein are methods and compositions that can be used to improve motor deficits and neuroinflammation in subjects in need, for example subjects suffering from neurodegenerative disorders (e.g., Parkinson's disease). Also disclosed are methods and compositions that can be used to diagnose neurodegenerative disorders, such as Parkinson's disease.

14 Claims, 31 Drawing Sheets

Specification includes a Sequence Listing.

(56) References Cited

U.S. PATENT DOCUMENTS

| | | |
|---|---|---|
| 2016/0339065 A1 | 11/2016 | Adams et al. |
| 2017/0024527 A1 | 1/2017 | Apte et al. |
| 2018/0196044 A1 | 7/2018 | Mazmanian et al. |
| 2019/0388481 A1 | 12/2019 | Mazmanian et al. |
| 2022/0040145 A1 | 2/2022 | Sampson |

FOREIGN PATENT DOCUMENTS

| | | |
|---|---|---|
| WO | WO 01/19361 | 3/2001 |
| WO | WO 01/049281 | 7/2001 |
| WO | WO 02/007741 | 1/2002 |
| WO | WO 03/037891 | 5/2003 |
| WO | WO 06/090185 | 8/2006 |
| WO | WO 06/110406 | 10/2006 |
| WO | WO 07/080721 | 7/2007 |
| WO | WO 09/055362 | 4/2008 |
| WO | WO 09/003147 | 12/2008 |
| WO | WO 10/056985 | 5/2010 |
| WO | WO 10/082205 | 7/2010 |
| WO | WO 10111516 | 9/2010 |
| WO | WO 11/050397 | 5/2011 |
| WO | WO 11/139914 | 11/2011 |
| WO | WO 12/048152 | 4/2012 |
| WO | WO 12/159052 | 11/2012 |
| WO | WO 14/076655 | 5/2014 |
| WO | WO 14/121301 | 8/2014 |
| WO | WO 15/181449 | 12/2015 |
| WO | WO 16/110768 | 7/2016 |
| WO | WO 17/205302 | 11/2017 |

OTHER PUBLICATIONS

Altieri et al. (2011). Urinary p-cresol is elevated in small children with severe autism spectrum disorder. Biomarkers 16, 252-260.

Amaral et al. (2008). Commensal microbiota is fundamental for the development of inflammatory pain. Proc Natl Acad Sci USA 105, 2193-2197.

Amasheh et al. (2009). Na+ absorption defends from paracellular back-leakage by claudin-8 upregulation. Biochem Biophys Res Commun 378, 45-50.

American Psychiatric Association: Diagnostic and Statistical Manual of Mental Disorders, Fourth Edition, Text Revision. Washington, DC, pp. 69-84, American Psychiatric Association, 2000.

Atladottir, et al. (2010). Maternal infection requiring hospitalization during pregnancy and autism spectrum disorders. J Autism Dev Disord 40, 1423-1430.

Bailey, K.R., and Crawley, J.N. (2009). Anxiety-Related Behaviors in Mice. In Methods of Behavior Analysis in Neuroscience, J.J. Buccafusco, ed. (Boca Raton (FL)).

Barbara, et al. (2005) "Interactions between commensal bacteria and gut sensorimotor function in health and disease" The American journal of gastroenterology 100, 2560-2568.

Barnhart et al, 2006, Curli biogenesis and function, Ann Rev Microbiol 60: 131-147.

Bercik et al. (2011). The anxiolytic effect of Bifidobacterium longum NCC3001 involves vagal pathways for gut-brain communication. Neurogastroenterol Motil 23, 1132-1139.

Blumberg, R., and Powrie, F. (2012). Microbiota, disease, and back to health: a metastable journey. Sci Transl Med 4, 137rv137.

Boksa, P. (2010). Effects of prenatal infection on brain development and behavior: a review of findings from animal models. Brain Behav Immun 24, 881-897.

Bourin et al. (2007). Animal models of anxiety in mice. Fundamental & clinical pharmacology 21, 567-574.

Bravo et al. (2011). Ingestion of Lactobacillus strain regulates emotional behavior and central GABA receptor expression in a mouse via the vagus nerve. Proc Natl Acad Sci U S A 108, 16050-16055.

Breiman, L. (2001). Random forests. Mach Learn 45, 5-32.

Brown, et al. (2000). Stress produced by gavage administration in the rat. Contemporary topics in laboratory animal science—American Association for Laboratory Animal Science 39, 17-21.

Buie, et al. (2010). Evaluation, diagnosis, and treatment of gastrointestinal disorders in individuals with ASDs: a consensus report. Pediatrics 125 Suppl 1, S1-18.

Bull et al. (2003). Indolyl-3-acryloylglycine (IAG) is a putative diagnostic urinary marker for autism spectrum disorders. Med Sci Monit 9, CR422-425.

Burlingham et al. (2003). 34S isotope effect on sulfate ester hydrolysis: mechanistic implications. J Am Chem Soc 125, 13036-13037.

Campbell et al., Bacterial diversity, community structure and potential growth rates along an estuarine salinity gradient, Isme J, (2012).

Canitano, R., and Scandurra, V. (2008). Risperidone in the treatment of behavioral disorders associated with autism in children and adolescents. Neuropsychiatr Dis Treat 4, 723-730.

Caporaso et al. (2010). PyNAST: a flexible tool for aligning sequences to a template alignment. Bioinformatics 26, 266-267.

Caporaso et al. (2010). QIIME allows analysis of high-throughput community sequencing data. Nat Methods 7, 335-336.

Cassani et al., 2015, Increased urinary indoxyl sulfate (indican): new insights into gut dysbiosis in Parkinson's disease, Parkinsonism and Related Disorders, 21:389-393.

CDC (2012). Prevalence of autism spectrum disorders—autism and developmental disabilities monitoring network, 14 sites, United States, 2008. MMWR Surveill Summ 61, 1-19.

Chen et al., 2016, Exposure to the functional bacterial amyloid protein curli enhances alpha-synuclein aggregation in aged fischer 344 rats and caenorhabditis elegans, Scientific Reports, 6:1-10.

Chi, "Clinical, animal studies probe DISC1's role in autism" Spectrum, Mar. 1, 2010, https://spectrumnews.org/news/clinical-animal-studies-probe-disc1s-role-in-autism/.

Chorell et al. "Bacterial Chaperones CsgE and CsgC Differentially Modulate Human α-Synuclein Amyloid Formation via Transient Contacts", (2015). PLoS ONE 10(10).

Clemente et al. (2012). The impact of the gut microbiota on human health: an integrative view. Cell 148, 1258-1270.

Cohen-Poradosu et al. (2011). Bacteroides fragilis-stimulated interleukin-10 contains expanding disease. The Journal of infectious diseases 204, 363-371.

Collins et al. (2012). The interplay between the intestinal microbiota and the brain. Nat Rev Microbiol 10, 735-742.

Collinson et al., "Purification and characterization of thin, aggregative fimbriae from *Salmonella enteritidis*", (1991), *Journal of Bacteriology.* 173(15).

Coury, et al. (2012). Gastrointestinal conditions in children with autism spectrum disorder: developing a research agenda. Pediatrics 130 Suppl 2, S160-168.

Credle et al., 2015, GSK-3β3 dysregulation contributes to parkinson's-like pathophysiology with associated region-specific phosphorylation and accumulation of tau and a-synuclein, Cell Death & Differentiation, 22: 838-851.

Critchfield, et al. (2011). The potential role of probiotics in the management of childhood autism spectrum disorders. Gastroenterology research and practice 2011, 161358.

Cryan, J.F., and Dinan, T.G. (2012). Mind-altering microorganisms: the impact of the gut microbiota on brain and behaviour. Nat Rev Neurosci 13, 701-712.

De Angelis et al., "Fecal Microbiota and Metabolome of Children with Autism and Pervasive Developmental Disorder Not Otherwise Specified", PLOS ONE, vol. 8, No. 10, e76993, pp. 1-18, Oct. 2013.

De Hoon et al. (2004). Open source clustering software. Bioinformatics 20, 1453-1454.

De Magistris et al. (2010). Alterations of the intestinal barrier in patients with autism spectrum disorders and in their first-degree relatives. J Pediatr Gastroenterol Nutr 51, 418-424.

Desbonnet, et al. (2013). Microbiota is essential for social development in the mouse. Molecular psychiatry.

D'Eufemia, et al. (1996). Abnormal intestinal permeability in children with autism. Acta Paediatr 85, 1076-1079.

Edgar, et al. (2011). UCHIME improves sensitivity and speed of chimera detection. Bioinformatics 27, 2194-2200.

Edgar, R.C. (2010). Search and clustering orders of magnitude faster than BLAST. Bioinformatics 26, 2460-2461.

Evans et al., 2015, The bacterial curli system possesses a potent and selective inhibitor of amyloid formation, Mol Cell 57:1-23.

(56) References Cited

OTHER PUBLICATIONS

Ewaschuk, et al. (2008). Secreted bioactive factors from Bifidobacterium infantis enhance epithelial cell barrier function. Am J Physiol Gastrointest Liver Physiol 295, G1025-1034.
Faith, D.P. (1992). Conservation Evaluation and Phylogenetic Diversity. Biol Conserv 61, 1-10.
Farlow et al., May 24, 2014, Parkinson disease overview, GeneReviews, pp. 1-2 (abstract).
Fasano et al., May 27, 2013, The role of small intestinal bacterial overgrowth in Parkinson's disease: sibo in Parkinson's disease, Movement Disorders, 28(9):1241-1249.
Finegold, et al. (2002). Gastrointestinal microflora studies in late-onset autism. Clin Infect Dis 35, S6-S16.
Finegold, et al. (2010). Pyrosequencing study of fecal microflora of autistic and control children. Anaerobe 16, 444-453.
Finegold, et al. (2012). Microbiology of regressive autism. Anaerobe 18, 260-262.
Finegold, S.M. (2011). Desulfovibrio species are potentially important in regressive autism. Medical hypotheses 77, 270-274.
Fleming et al. "Early and Progressive Sensorimotor Anomalies in Mice Overexpressing Wild-Type Human-Synuclein", J. Neurosci. 24, 9434-9440 (2004).
Frye, et al. (2013). Unique acyl-carnitine profiles are potential biomarkers for acquired mitochondrial disease in autism spectrum disorder. Translational psychiatry 3, e220.
Ganapathy et al., "Endogenous Elevation of Homocysteine Induces Retinal Neuron Death in the Cystathionine-Beta-Synthease Mutant Mouse," Invest. Opthamol. Vis. Sci., 50(9):4460-4470 (2009).
Geyer, M.A., and Swerdlow, N.R. (2001). Measurement of startle response, prepulse inhibition, and habituation. Curr Protoc Neurosci Chapter 8, Unit 8 7.
Gondalia, et al. (2012). Molecular characterisation of gastrointestinal microbiota of children with autism (with and without gastrointestinal dysfunction) and their neurotypical siblings. Autism Res 5, 419-427.
Gorrindo, et al. (2012). Gastrointestinal dysfunction in autism: parental report, clinical evaluation, and associated factors. Autism Res 5, 101-108.
Gorrindo, et al. (2013). Enrichment of elevated plasma f2t-isoprostane levels in individuals with autism who are stratified by presence of gastrointestinal dysfunction. PLoS One 8, e68444.
Grenham, G. Clarke, J. F. Cryan, T. G. Dinan, Brain-gut-microbe communication in health and disease. Front Physiol 2, 94 (Dec. 7, 2011).
Grimes, A.J. (1959). Synthesis of 35S-labelled arylsulphates by intact animals and by tissue preparations, with particular reference to l-tyrosine O-sulphate. Biochem J 73, 723.
Grimsley, et al. (2011). Development of social vocalizations in mice. PLoS one 6, e17460.
Gulati et al., Mouse Background Strain Profoundly Influences Paneth Cell Function and Intestinal Microbial Composition, PLoS One 7, e32403 (2012).
Gupta, "The phylogeny of proteobacteria: relationships to other eubacterial phyla and eukaryotes.", FEMS Microbiology Reviews 24 (4):367-402, 2000.
Hallmayer, et al. (2011). Genetic heritability and shared environmental factors among twin pairs with autism. Arch Gen Psychiatry 68, 1095-1102.
Hammock et al., "2003 Progress Report: Environmental Factors in the Etiology of Autism: Analytic Biomarkers (xenobiotic) Core," Extramural Research, United States Environmental Protection Agency (2003), retrieved online from EPA. <http://cfpub.epa.gov/ncer_abstracts/index.cfm/fuseaction/display.abstractDetail/abstract/7872/report/2003>.
Han, et al. (2012). Autistic-like behaviour in Scn1a+--mice and rescue by enhanced GABA-mediated neurotransmission. Nature 489, 385-390.
Hansen et al. The colitis-associated transcriptional profile of commensal Bacteroides thetaiotaomicron enhances adaptive immune responses to a bacterial antigen. PLoS One. 2012;7(8):e42645. doi: 10.1371/journal.pone.0042645. Epub Aug. 3, 2012.
Heijtz, et al. (2011). Normal gut microbiota modulates brain development and behavior. Proc Natl Acad Sci U S A 108, 3047-3052.
Hering, et al. (2012). Determinants of colonic barrier function in inflammatory bowel disease and potential therapeutics. The Journal of physiology 590, 1035-1044.
Holmes, et al. (2006). Claudin profiling in the mouse during postnatal intestinal development and along the gastrointestinal tract reveals complex expression patterns. Gene Expr Patterns 6, 581-588.
Hooper, et al. (2012). Interactions between the microbiota and the immune system. Science 336, 1268-1273.
Horvath, K., and Perman, J.A. (2002). Autism and gastrointestinal symptoms. Curr Gastroenterol Rep 4, 251-258.
Hsiao et al., "Microbiota modulate behavioral and physiological abnormalities associated with neurodevelopmental disorders," Cell, vol. 155, No. 7, pp. 1451-1463 Dec. 1, 2013.
Hsiao, E.Y., and Patterson, P.H. (2011). Activation of the maternal immune system induces endocrine changes in the placenta via IL-6. Brain Behav Immun 25, 604-615.
Hsiao, Elaine, "Gastrointestinal Issues in Autism spectrum disorder", Harvard Review of Psychiatry, Mar.-Apr. 2014, vol. 22(2), pp. 104-111.
Hsiao, et al. (2012). Modeling an autism risk factor in mice leads to permanent immune dysregulation. Proc Natl Acad Sci U S A 109, 12776-12781.
Huang, et al. (2011). The human commensal Bacteroides fragilis binds intestinal mucin. Anaerobe 17, 137-141.
Hung et al., 2014, The bacterial amyloid curli is associated with urinary source bloodstream infection, PLOS ONE 9:1-6.
Ibrahim, et al. (2009). Incidence of gastrointestinal symptoms in children with autism: a population-based study. Pediatrics 124, 680-686.
Jandhyala et al., "Role of the normal gut microbiota", World Journal of Gastroenterology 21(9): 8787-8803, 2015.
Kang, et al. (2013). Reduced Incidence of and Other Fermenters in Intestinal Microflora of Autistic Children. PLoS One 8, e68322.
Kau, et al. (2011). Human nutrition, the gut microbiome and the immune system. Nature 474, 327-336.
Keshavarzian et al., 2015, Colonic bacterial composition in Parkinson's disease, Movement Disorders, 30(10):1351-1360.
Keszthelyi, et al. (2009). Understanding the role of tryptophan and serotonin metabolism in gastrointestinal function. Neurogastroenterol Motil 21, 1239-1249.
Kidd, Autism, an extreme challege to integrative medicine. Part 2: medical management. Altern. Med. Rev. vol. 7, No. 6, pp. 472-499 (2002).
Kilpinen, et al., Association of DISC1 with autism and Asperger syndrome Molecular Psychiatry (2008) 13, 187-196.
Kim et al., 2009, Minocycline and Neurodegenerative diseases, Behavioural Brain Research 196:168-179.
Klein et al., 2015, Chaos controlled: discovery of a powerful amyloid inhibitor, Mol Cell Previews, 57:391-393.
Knights, et al. (2011). Supervised classification of human microbiota. FEMS microbiology reviews 35, 343-359.
Koenig, et al. (2011). Succession of microbial consortia in the developing infant gut microbiome. Proc Natl Acad Sci U S A 108 Suppl 1, 4578-4585.
Kohane, et al. (2012). The co-morbidity burden of children and young adults with autism spectrum disorders. PLoS One 7, e33224.
Korosi, et al. (2012). Early-life stress mediated modulation of adult neurogenesis and behavior. Behav Brain Res 227, 400-409.
Kursa, M.B., and Rudnicki, W.R. (2010). Feature Selection with the Boruta Package. J Stat Softw 36, 1-13.
Lafaye, et al. (2004). Profiling of sulfoconjugates in urine by using precursor ion and neutral loss scans in tandem mass spectrometry. Application to the investigation of heavy metal toxicity in rats. J Mass Spectrom 39, 655-664.
Lavatelli et al., 2011, Proteomic typing of amyloid deposits in systemic amyloidoses, Amyloid 18:177-182.

(56) References Cited

OTHER PUBLICATIONS

Lazic, S.E. (2013). Comment on "Stress in puberty unmasks latent neuropathological consequences of prenatal immune activation in mice". Science 340, 811; discussion 811.
Leatham, et al. (2009). Precolonized human commensal *Escherichia coli* strains serve as a barrier to *E. coli* O157:H7 growth in the streptomycin-treated mouse intestine. Infect Immun 77, 2876-2886.
Lee et al., in International Meeting for Autism Research (Toronto, Canada, May 17-19, 2012).
Lee, A., and Gemmell, E. (1972). Changes in the mouse intestinal microflora during weaning: role of volatile fatty acids. Infect Immun 5, 1-7.
Li et al., 2004, Dopamine and L-dopa disaggregate amyloid fibrils: implications for Parkinson's and Alzheimer's disease, The Faseb Journal express article, pp. 1-22.
Lionnet et al., 2018, Does Parkinson's disease start in the gut?, Acta Neuropathol, 135:1-12.
Lopetuso et al., "Commensal Clostridia: leading players in the maintenance of gut homeostasis", Gut Pathogents 5(1): 23, 2013.
Lozupone, C., and Knight, R. (2005). UniFrac: a new phylogenetic method for comparing microbial communities. Appl Environ Microbiol 71, 8228-8235.
Ludwig, et al. (2004). ARB: a software environment for sequence data. Nucleic Acids Res 32, 1363-1371.
MacFabe, D.F. (2012). Short-chain fatty acid fermentation products of the gut microbiome: implications in autism spectrum disorders. Microbial Ecology in Health & Disease 23, 19260.
Malkova, et al. (2012). Maternal immune activation yields offspring displaying mouse versions of the three core symptoms of autism. Brain Behav Immun 26, 607-616.
Mandal, et al. (2011). Maternal immune stimulation during pregnancy affects adaptive immunity in offspring to promote development of TH17 cells. Brain Behav Immun 25, 863-871.
Maslowski, et al., "Diet, gut microbiota and immune responses" Nature Immunology vol. 12 No. 1, pp. 5-9, Jan. 2011.
Matsumoto, et al. (2012). Impact of intestinal microbiota on intestinal luminal metabolome. Sci Rep 2, 233.
Mayer, E.A. (2011). Gut feelings: the emerging biology of gut-brain communication. Nat Rev Neurosci 12, 453-466.
Mazmanian, et al. (2008). A microbial symbiosis factor prevents intestinal inflammatory disease. Nature 453, 620-625.
Mazurek, et al. (2013). Anxiety, sensory over-responsivity, and gastrointestinal problems in children with autism spectrum disorders. J Abnorm Child Psychol 41, 165-176.
McCarthy et al. (2015), STC-1 Cells. In: Verhoeckx K. et al. (eds) *The Impact of Food Bioactives on Health*. Springer, Cham.
Ming, et al. (2012). Metabolic perturbance in autism spectrum disorders: a metabolomics study. Journal of proteome research 11, 5856-5862.
Mulder, et al. (2004). Platelet serotonin levels in pervasive developmental disorders and mental retardation: diagnostic group differences, within-group distribution, and behavioral correlates. J Am Acad Child Adolesc Psychiatry 43, 491-499.
Mulle et al., "The Gut Microbiome: A New Frontier in Autism Research", Curr Psychiatry Rep., vol. 15, No. 2, pp. 1-13, Feb. 2013.
Nemeroff et al., "Are platelets the link between depression and ischemic heart disease?", American Heat Journal 140(4): S57-S62, 2000.
Nicholson, et al. (2012) "Host-gut microbiota metabolic interactions" Science 336, 1262-1267.
Nieswandt, et al. (2004) "Flow-cytometric analysis of mouse platelet function" Methods Mol Biol 272, 255-268.
Nikolov, et al. (2009). Gastrointestinal symptoms in a sample of children with pervasive developmental disorders. J Autism Dev Disord 39, 405-413.
Novarino, et al. (2012). Mutations in BCKD-kinase lead to a potentially treatable form of autism with epilepsy. Science 338, 394-397.
Ochoa-Reparaz, et al. (2010). Central nervous system demyelinating disease protection by the human commensal Bacteroides fragilis depends on polysaccharide A expression. J Immunol 185, 4101-4108.
Odamaki, et al. (2008). Distribution of different species of the Bacteroides fragilis group in individuals with Japanese cedar pollinosis. Appl Environ Microbiol 74, 6814-6817.
O'Mahony, et al. (2009). Early life stress alters behavior, immunity, and microbiota in rats: implications for irritable bowel syndrome and psychiatric illnesses. Biological psychiatry 65, 263-267.
Ono et al., 2006, Antioxidant compounds have potent anti-fibriliogenic and fibril-destabilzing effects for alpha-synuclein fibrils in vitro, Journal of Neurochemistry, 97:105-115.
Onore, et al. (2012). The role of immune dysfunction in the pathophysiology of autism. Brain Behav Immun 26, 383-392.
Parracho, et al. (2005b). Differences between the gut microflora of children with autistic spectrum disorders and that of healthy children. Journal of medical microbiology 54, 987-991.
Patterson, Maternal Infection and Immune Involvement in Autism, Trends Mol Med 17, 389 (Jul. 2011).
Patterson, P. H. 2011. Modeling features of autism in animals. Pediatric Res 69:34R-40R.
Penagarikano et al., "What does CNTNAP2 reveal about autism spectrum disorder?" Trends in Molecular Medicine, 2012, vol. 18, pp. 156-163.
Penagarikano, et al. (2011). Absence of CNTNAP2 leads to epilepsy, neuronal migration abnormalities, and core autism-related deficits. Cell 147, 235-246.
Perry, et al. (2007). Sensorimotor gating deficits in adults with autism. Biological psychiatry 61, 482-486.
Persico, A.M., and Napolioni, V. (2012). Urinary p-cresol in autism spectrum disorder. Neurotoxicology and teratology 36, 82-90.
Petra, Louis, "Does the human gut mircrobiota contribute to the etiology of autism spectrum disorders?", Digestive diseases and sciences, vol. 57, No. 8, Jun. 27, 2012, pp. 1987-1989.
Phillips et al., 2009, Alpha-synuclein immunopositive aggregates in the myenteric plexus of the aging Fischer 344 rat, Experiment Neural, 220:109-119.
Portfors, C.V. (2007). Types and functions of ultrasonic vocalizations in laboratory rats and mice. J Am Assoc Lab Anim Sci 46, 28-34.
Price, et al. (2009). FastTree: Computing Large Minimum Evolution Trees with Profiles instead of a Distance Matrix. Mol Biol Evol 26, 1641-1650.
Pruesse, et al. (2012). SINA: Accurate high-throughput multiple sequence alignment of ribosomal RNA genes. Bioinformatics 28, 1823-1829.
Quast, et al. (2013). The SILVA ribosomal RNA gene database project: improved data processing and web-based tools. Nucleic Acids Res 41, D590-D596.
Rao, et al. (2009). A randomized, double-blind, placebo-controlled pilot study of a probiotic in emotional symptoms of chronic fatigue syndrome. Gut Pathog 1, 6.
Resta-Lenert, S.C., and Barrett, K.E. (2009). Modulation of intestinal barrier properties by probiotics: role in reversing colitis. Ann N Y Acad Sci 1165, 175-182.
Riehle, et al. (2012). The Genboree Microbiome Toolset and the analysis of 16S rRNA microbial sequences. Bmc Bioinformatics 13.
Rietdijk et al., "Exploring Braak's Hypothesis of Parkinson's Disease", Front. Neurol., Feb. 13, 2017.
Robinson, et al. "From Structure to Function: the Ecology of Host-Associated Microbial Communities" Microbiology and Molecular Biology Reviews, Sep. 2010, pp. 456-476.
Rong et al., "Cystathionine Beta Synthase Participates in Murine Oocyte Maturation Mediated by Homocysteine," Reprod. Toxicol., 24(1):89-96 (2007).
Rossignol, D.A., and Frye, R.E. (2012). Mitochondrial dysfunction in autism spectrum disorders: a systematic review and meta-analysis. Mol Psychiatry 17, 290-314.
Round et al.: "Coordination of tolerogenic immune responses by the commensal microbiota." J. Autoimmun., 34:J220-225 (2010).

(56) References Cited

OTHER PUBLICATIONS

Round, J.L., and Mazmanian, S.K. (2009). The gut microbiota shapes intestinal immune responses during health and disease. Nat Rev Immunol 9, 313-323.
Round, J.L., and Mazmanian, S.K. (2010). Inducible Foxp3+ regulatory T-cell development by a commensal bacterium of the intestinal microbiota. Proc Natl Acad Sci U S A 107, 12204-12209.
Rowland et al., 2018, Gut microbiota functions: metabolism of nutrients and other food components, Eur J Nutr. 57(1):1-24.
Saldanha, A.J. (2004). Java Treeview-extensible visualization of microarray data. Bioinformatics 20, 3246-3248.
Sampson et al., "Gut Microbiota Regulate Motor Deficits and Neuroinflammation in a Model of Parkinson's Disease", Cell 167(6):1469-1480 (2016).
Sandler, et al. (2000). Short-term benefit from oral vancomycin treatment of regressive-onset autism. J Child Neurol 15, 429-435.
Sankoorikal, et al. (2006). A mouse model system for genetic analysis of sociability: C57BL/6J versus BALB/cJ inbred mouse strains. Biological psychiatry 59, 415-423.
Scattoni, et al. (2011). Unusual repertoire of vocalizations in adult BTBR T+tf/J mice during three types of social encounters. Genes, brain, and behavior 10, 44-56.
Schmeisser, et al. (2012). Autistic-like behaviours and hyperactivity in mice lacking ProSAP1/Shank2. Nature 486, 256-260.
Schwartzer, et al. (2013). Maternal immune activation and strain specific interactions in the development of autism-like behaviors in mice. Translational psychiatry 3, e240.
Segata, et al. (2011). Metagenomic biomarker discovery and explanation. Genome biology 12, R60.
Seltzer, et al., "The Symptoms of Autism Spectrum Disorders in Adolescence and Adulthood" Journal of Autism and Developmental Disorders, vol. 33, No. 6, pp. 565-581, Dec. 2003.
Sharma, et al. (2010) "Molecular modulation of intestinal epithelial barrier: contribution of microbiota" Journal of biomedicine & biotechnology 2010, 305879.
Shen et al., Feb. 12, 2021, The Association Between the Gut Microbiota and Parkinson's Disease, a Meta-Analysis, Front. Aging Neurosci., 13(636645):1-12.
Shi, et al. (2009). Activation of the maternal immune system alters cerebellar development in the offspring. Brain Behav Immun 23, 116-123.
Silverman, et al. (2010). Behavioural phenotyping assays for mouse models of autism. Nature Reviews Neuroscience 11, 490-502.
Smith et al. (1997). Formation of Phenolic and Indolic Compounds by Anaerobic Bacteria in the Human Large Intestine. Microb Ecol 33, 180-188.
Smith et al., Host Genetics and Environmental Factors Regulate Ecological Succession of the Mouse Colon Tissue-Associated Microbiota, PLoS One 7, e30273 (Jan. 2012).
Smith, et al. (2007). Maternal immune activation alters fetal brain development through interleukin-6. J Neurosci 27, 10695-10702.
Sommese, et al. (2012). Evidence of Bacteroides fragilis protection from Bartonella henselae-induced damage. PLoS One 7, e49653.
Song, et al. (2004). Real-time PCR quantitation of clostridia in feces of autistic children. Appl Environ Microbiol 70, 6459-6465.
Suzuki, et al. (2011). Interleukin-6 (IL-6) regulates claudin-2 expression and tight junction permeability in intestinal epithelium. J Biol Chem 286, 31263-31271.
Tabuchi, et al. (2007). A neuroligin-3 mutation implicated in autism increases inhibitory synaptic transmission in mice. Science 318, 71-76.
Tamura, et al. (2011). Loss of claudin-15, but not claudin-2, causes Na+ deficiency and glucose malabsorption in mouse small intestine. Gastroenterology 140, 913-923.
Thomas, et al. (2009). Marble burying reflects a repetitive and perseverative behavior more than novelty-induced anxiety. Psychopharmacology 204, 361-373.
Tillisch, et al. (2013). Consumption of fermented milk product with probiotic modulates brain activity. Gastroenterology 144, 1394-1401 e1394.

Tsai, et al. (2012). Autistic-like behaviour and cerebellar dysfunction in Purkinje cell Tsc1 mutant mice. Nature 488, 647-651.
Turner, J.R. (2009). Intestinal mucosal barrier function in health and disease. Nat Rev Immunol 9, 799-809.
Unger et al., Nov. 2016, Short chain fatty acids and gut microbiota differ between patients with Parkinson's disease and age-matched controls, Parkinsonism & Related Disorders, 32:66-72.
Van Kessel et al., 2019, Gut bacterial tyrosine decarboxylases restrict levels of levodopa in the treatment of Parkinson's disease, Nature Communications, 10(310):1-11.
Venegas et al., Mar. 11, 2019, Short Chain Fatty Acids (SCFAs)-Mediated Gut Epithelial and Immune Regulation and Its Relevance for Inflammatory Bowel Diseases, Front. Immunol., 19(277):1-16.
Wang et al., "Is Urinary Indolyl-3-Acryloylglycine A Biomarker for Autism with Gastrointestinal Symptoms?" Biomarkers, 14(8):596-603 (2009).
Wang, et al. (2011). The prevalence of gastrointestinal problems in children across the United States with autism spectrum disorders from families with multiple affected members. Journal of developmental and behavioral pediatrics, JDBP 32, 351-360.
Wang, et al. (2012). Elevated fecal short chain fatty acid and ammonia concentrations in children with autism spectrum disorder. Dig Dis Sci 57, 2096-2102.
White, et al. (2009). Statistical Methods for Detecting Differentially Abundant Features in Clinical Metagenomic Samples. Plos Comput Biol 5.
White, J.F. (2003). Intestinal pathophysiology in autism. Exp Biol Med (Maywood) 228, 639-649.
Wikoff, et al. (2009) "Metabolomics analysis reveals large effects of gut microflora on mammalian blood metabolites", Proc Natl Acad Sci USA 106, 3698-3703.
Williams, et al. (2011). Impaired carbohydrate digestion and transport and mucosal dysbiosis in the intestines of children with autism and gastrointestinal disturbances. PLoS One 6, e24585.
Williams, et al. (2012). Application of novel PCR-based methods for detection, quantitation, and phylogenetic characterization of *Sutterella* species in intestinal biopsy samples from children with autism and gastrointestinal disturbances. MBio 3.
Winek et al., "The Gut Microbiome as Therapeutic Target I Central Nervous System Diseases: Implications for Stroke", Neurotherapeutics 13(4): 762-774, 2016.
Wirtz, et al. (2007). Chemically induced mouse models of intestinal inflammation. Nature protocols 2, 541-546.
Wittebolle, et al. (2009). Initial community evenness favours functionality under selective stress. Nature 458, 623-626.
Won, et al. (2012). Autistic-like social behaviour in Shank2-mutant mice improved by restoring NMDA receptor function. Nature 486, 261-265.
Wu et al., Mar. 1, 2002, Blockade of microglial activation is neuroprotective in the 1-methyl-4-phenyl-1,2,3,6-tetrahydropyrine mouse model of Parkinson disease. The Journal of Neuroscience, 22(5):1763-1771.
Yadav, et al., "Pharmacological inhibition of gut-derived serotonin synthesis is a potential bone anabolic treatment for osteoporosis", Nature Medicine 16(3):308-312, 2010.
Yanamandra et al., Apr. 25, 2011, ?-synuclein reactive antibodies as diagnostic biomarkers in blood sera of Parkinson's disease patients, PLoS One, 6(4):e18513, 13 pp.
Yanamandra et al., Apr. 25, 2011, α-synuclein reactive antibodies as diagnostic biomarkers in blood sera of Parkinson's disease patients, PLoS One, 6(4):e18513.
Yang, et al. (2011). Automated three-chambered social approach task for mice. Curr Protoc Neurosci Chapter 8, Unit 8 26.
Yap, et al. (2010). Urinary metabolic phenotyping differentiates children with autism from their unaffected siblings and age-matched controls. Journal of proteome research 9, 2996-3004.
Yong et al, Dec. 2004, The promise of minocycline in neurology, Lancet Neurol, 3:744-751.
Zhou et al., "Promiscuous Cross-seeding between Bacterial Amyloids Promotes Interspecies Biofilms", (2012). Journal of Biological Chemistry 287(42).
International Search Report and Written Opinion dated Oct. 30, 2017 in International Application No. PCT/US17/33881.

(56) References Cited

OTHER PUBLICATIONS

Alkasir et al., Nov. 19, 2016, Human gut microbiota: the links with dementia development, Protein & Cell, 8(2):90-102.

Horvath et al, 2012, Mechanisms of protein oligomerization: inhibitor of functional amyloids templates ?-synuclein fibrillation, JACS 134:3439-3444.

Otzen et al., 2008, We find them here, we find them there: functional bacterial amyloid, Cell. Mol. Life Sci, 65:910-927.

Pistollato et al., Sep. 15, 2016, Role of gut microbiota and nutrients in amyloid formation and pathogenesis of Alzheimer disease, Nutrition Reviews, 74(10):624-634.

Schwartz et al., 2012, Microbial amyloids-functions and interactions within the host, Current Opinion in Microbiology, 16:93-99.

International Preliminary Report on Patentability issued Nov. 27, 2018 in International Application No. PCT/US17/33881.

\* cited by examiner

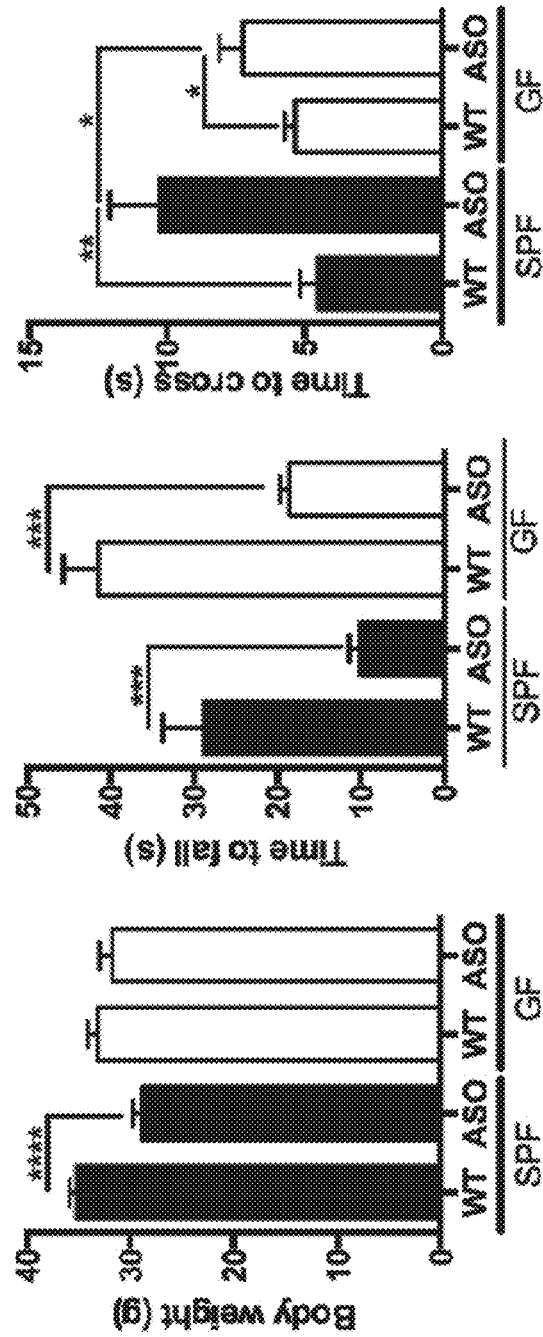
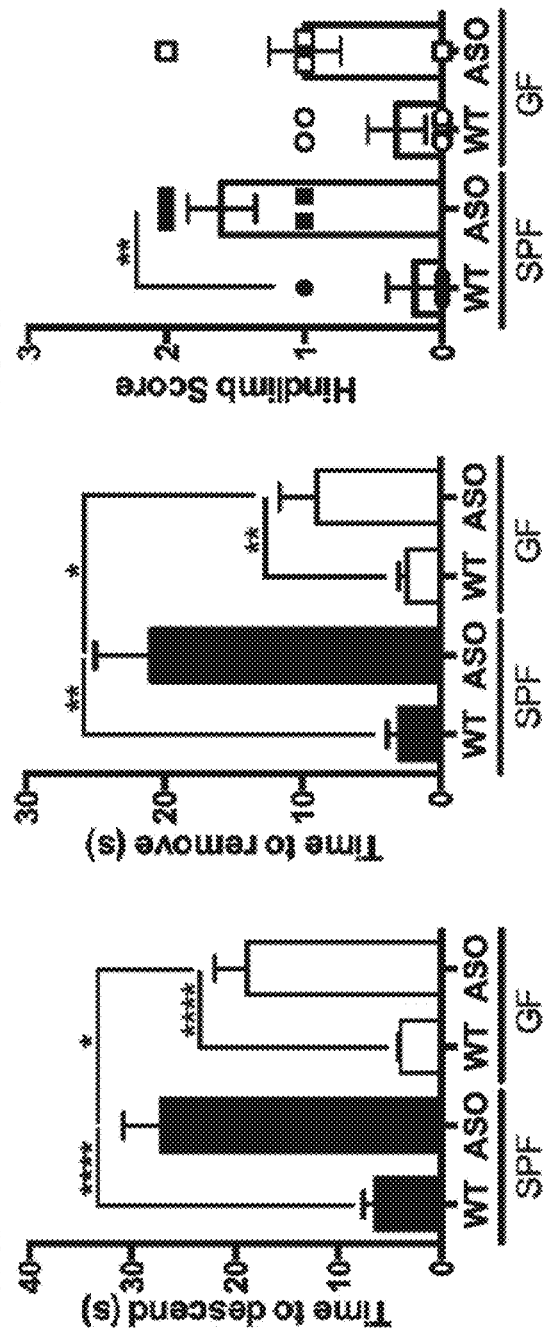

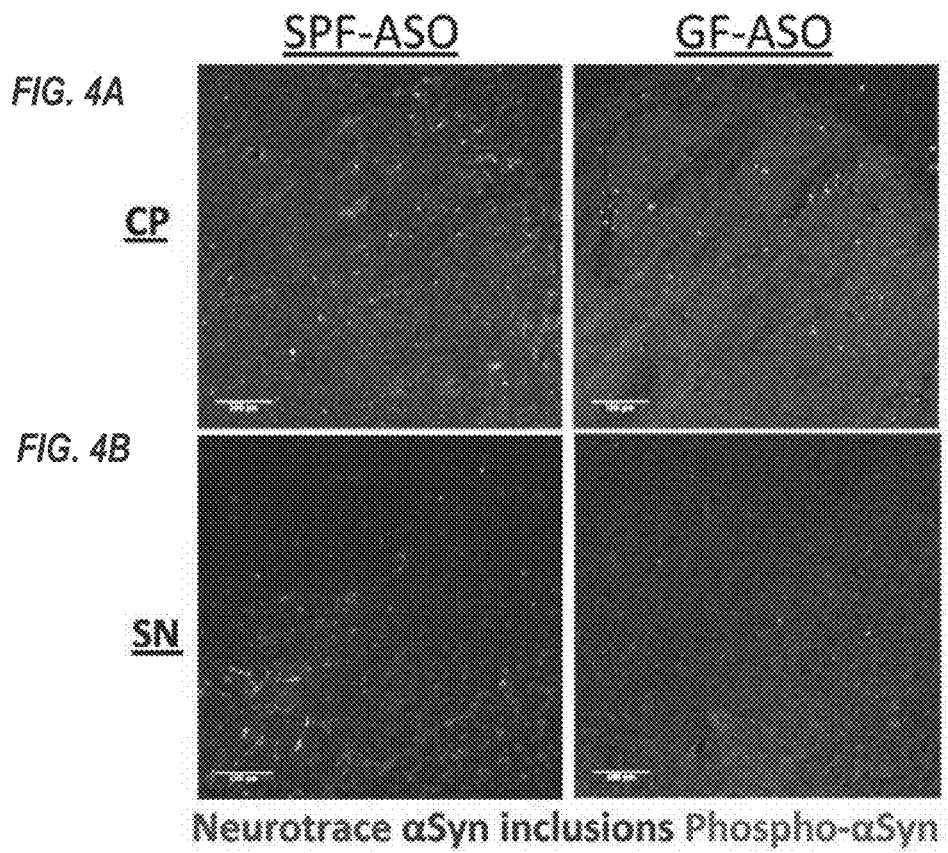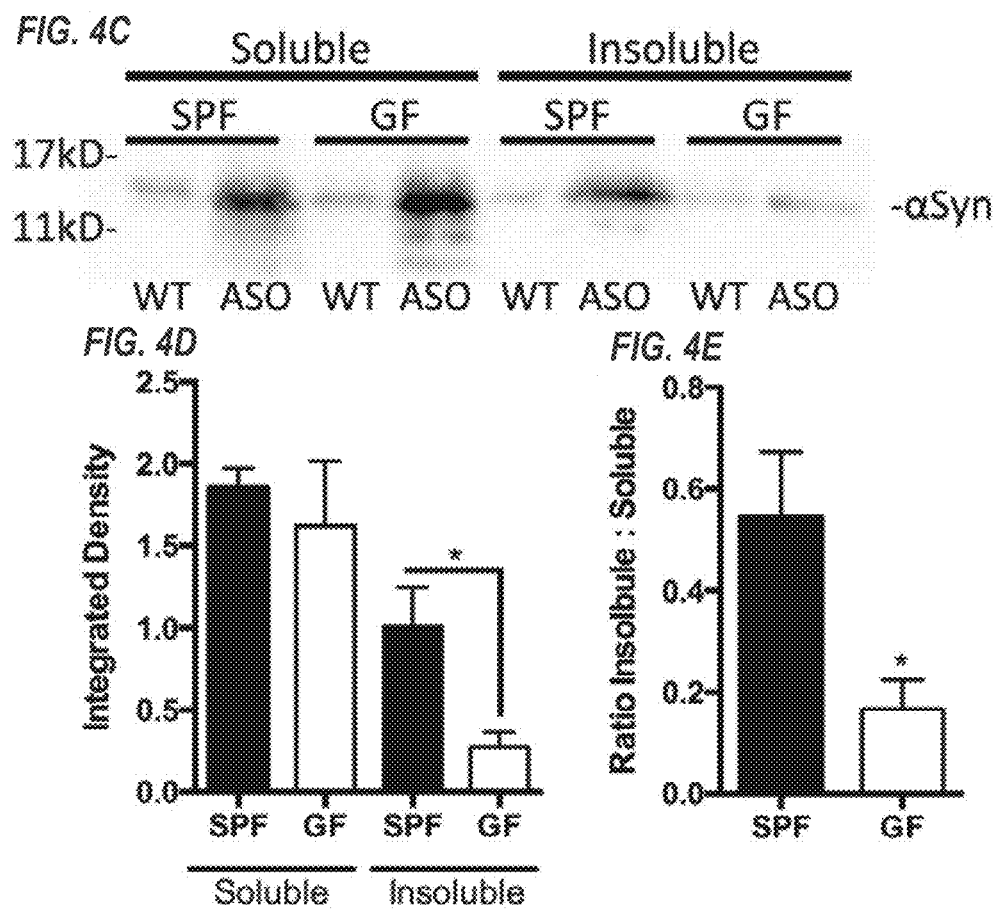

FIG. 4F
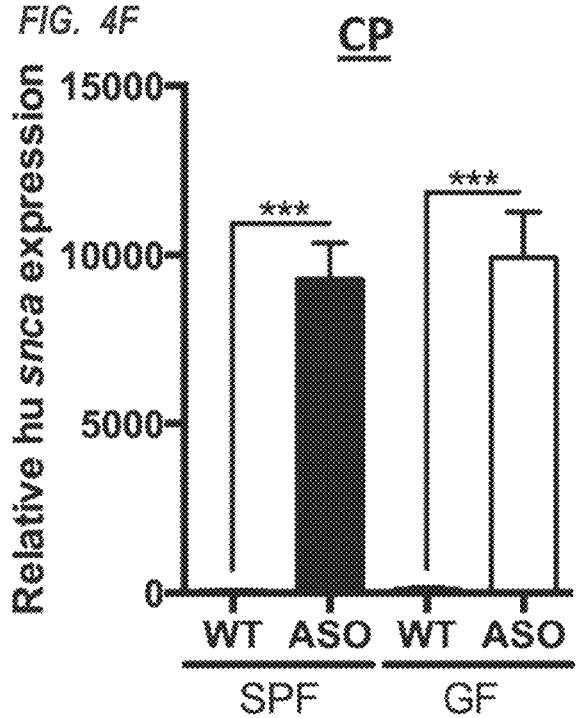
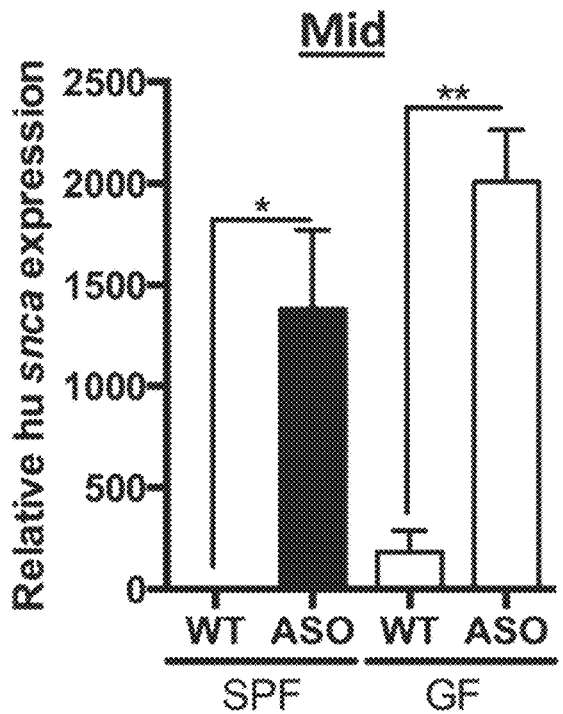
FIG. 4G
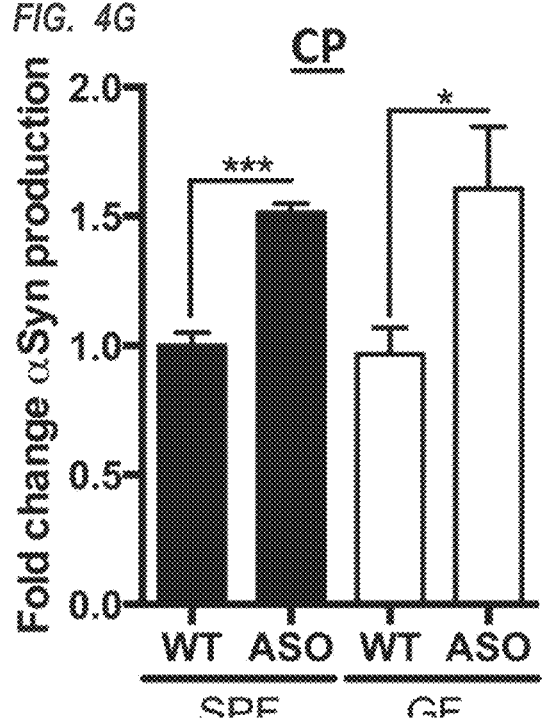
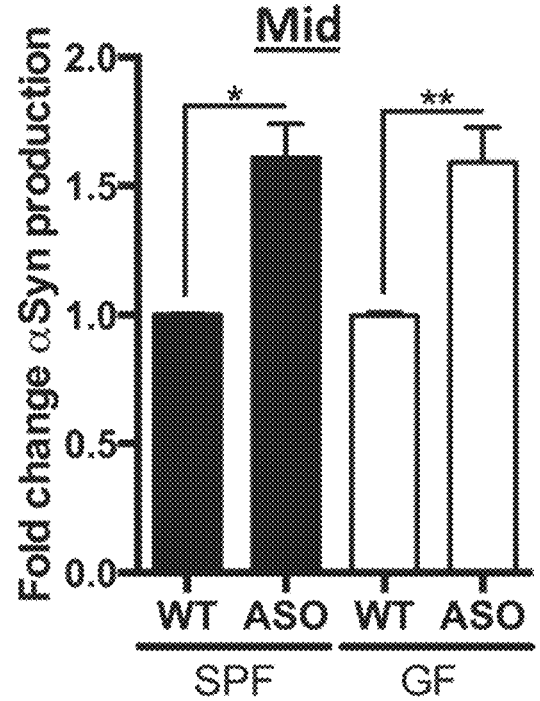

FIG. 5A
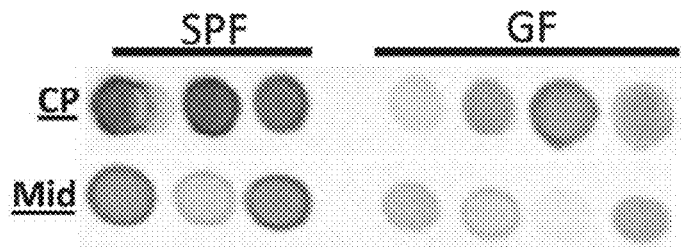
FIG. 5B CP
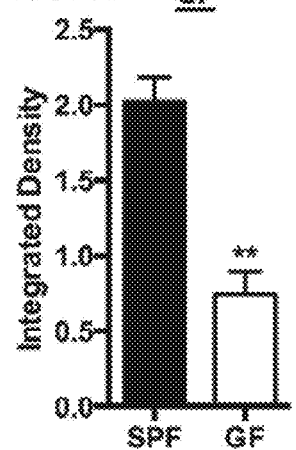
FIG. 5C Mid
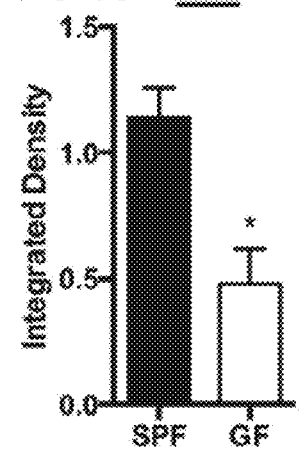
SPF GF
FIG. 5D
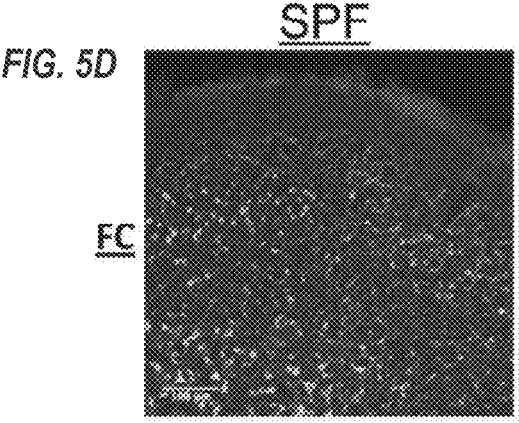
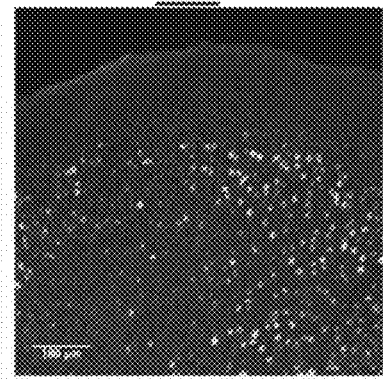
FC
FIG. 5E
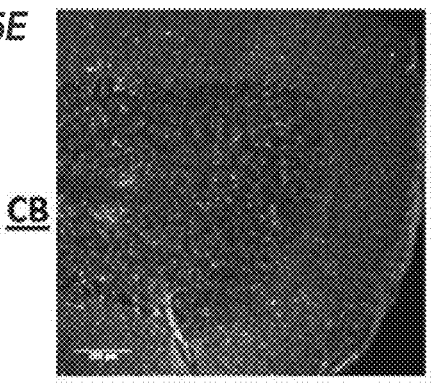
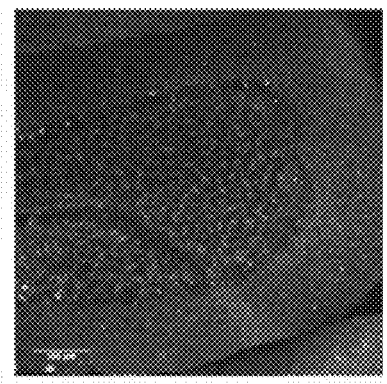
CB
Neurotrace αSyn inclusions Phospho-αSyn FIG. 5F
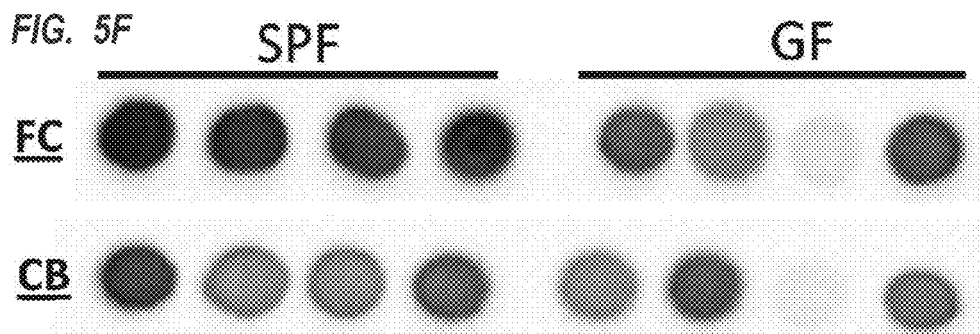

FIG. 5I
CD11b⁺
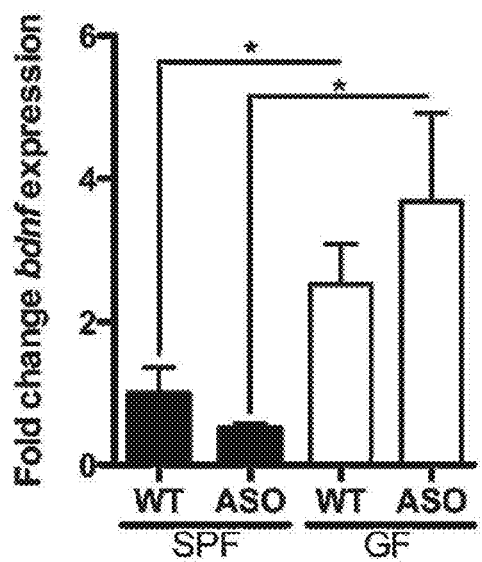 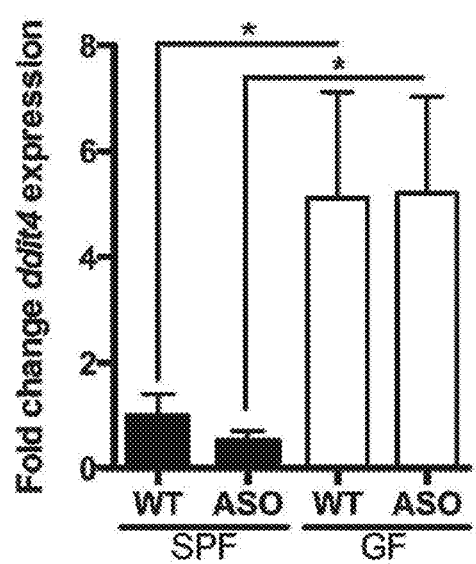

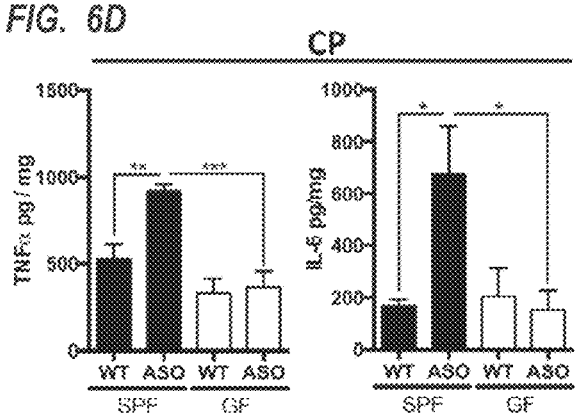
FIG. 6D
FIG. 6E
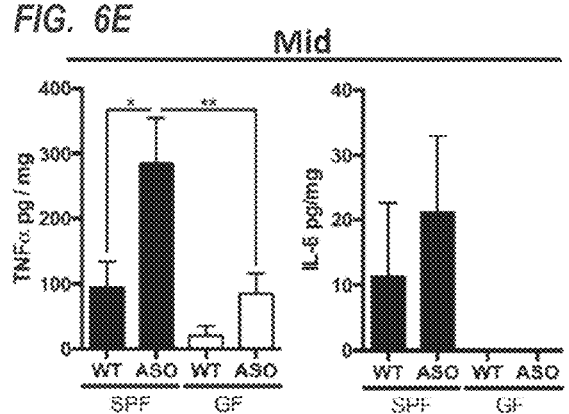
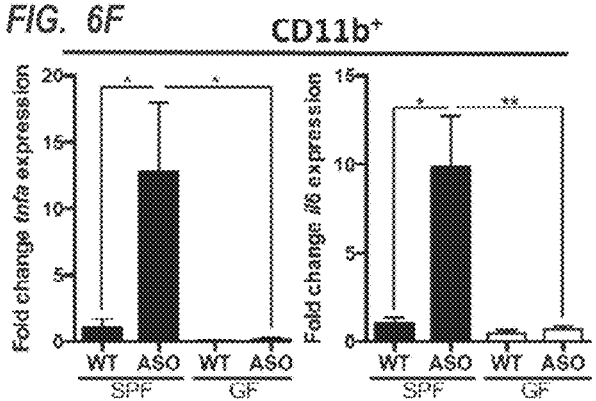
FIG. 6F
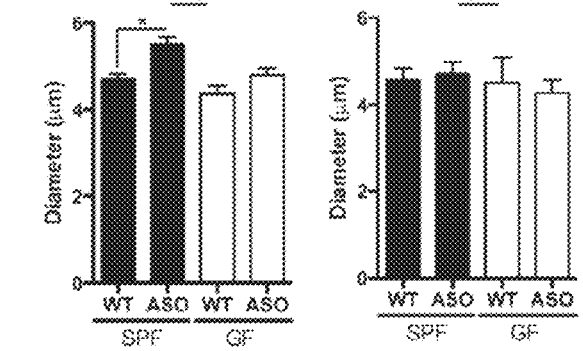
FIG. 6G
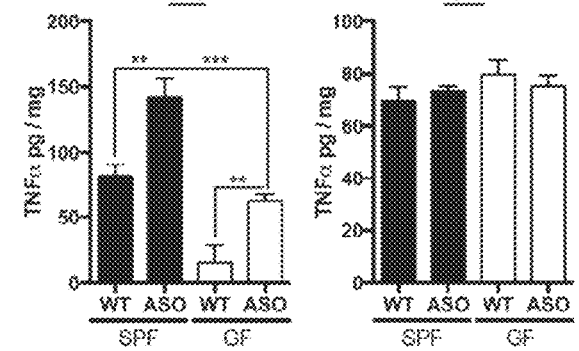
FIG. 6H FIG. 7F
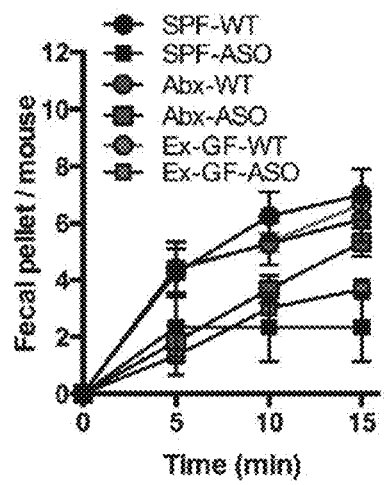
FIG. 7G
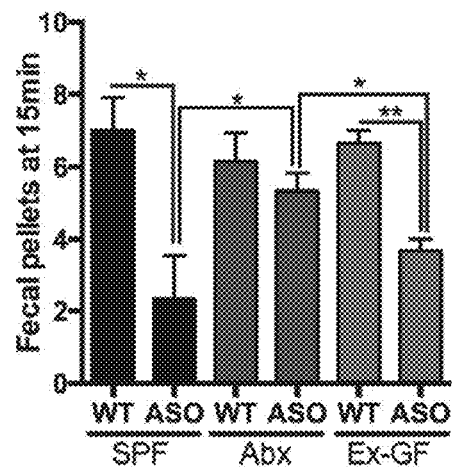
FIG. 7H
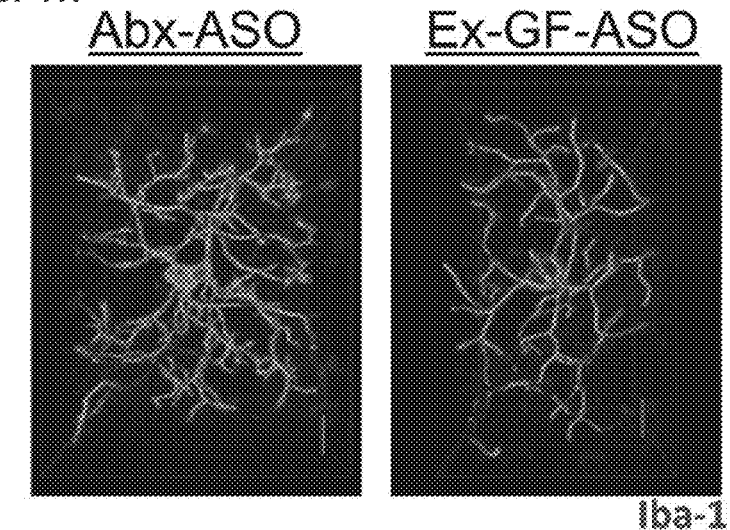
FIG. 7I
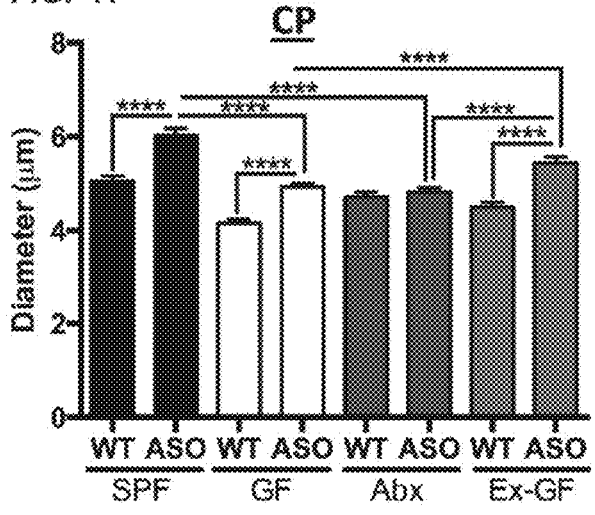
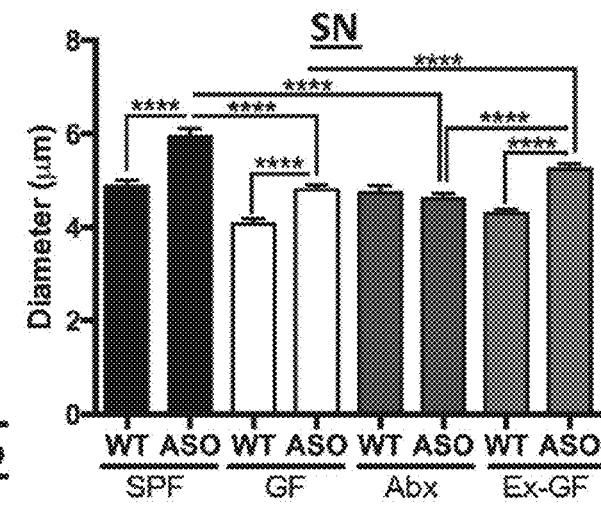
b

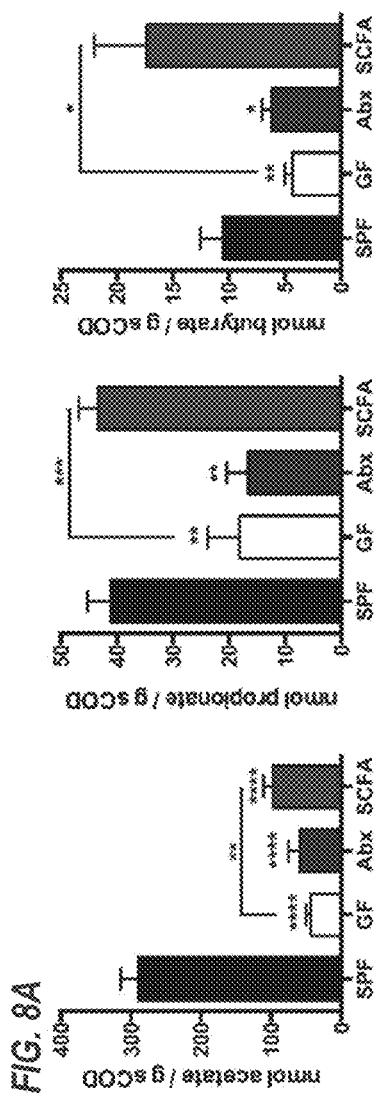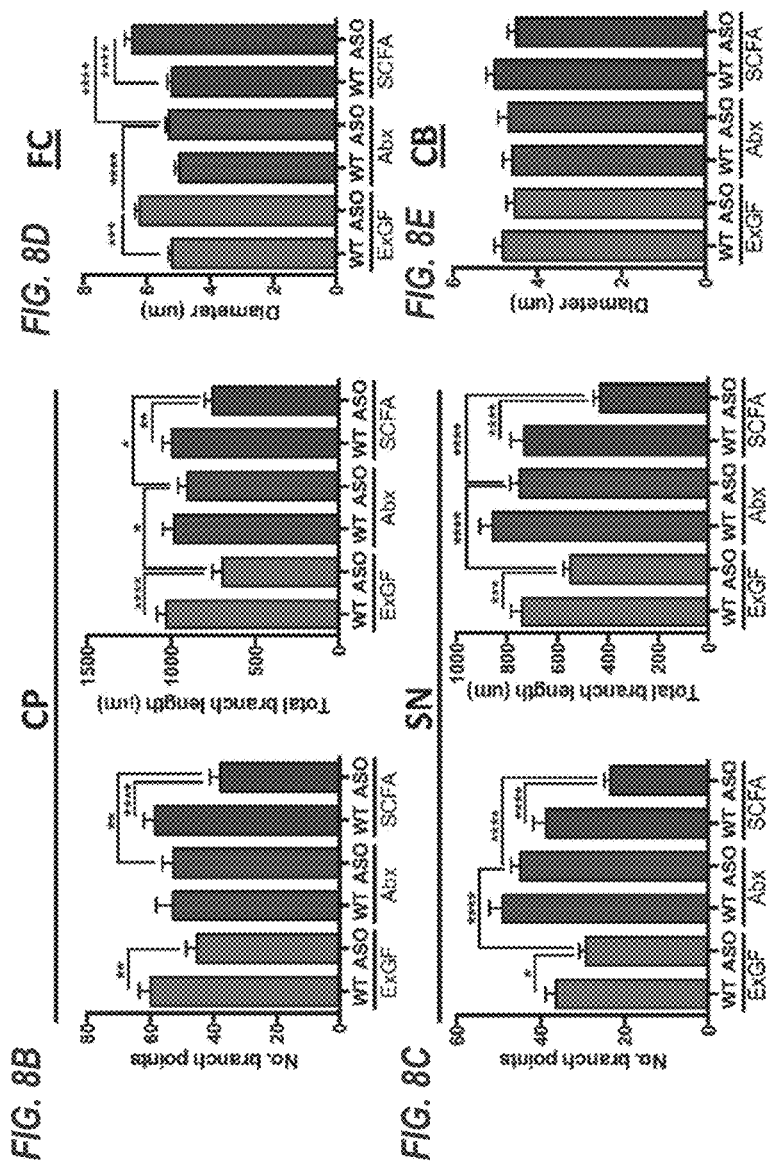

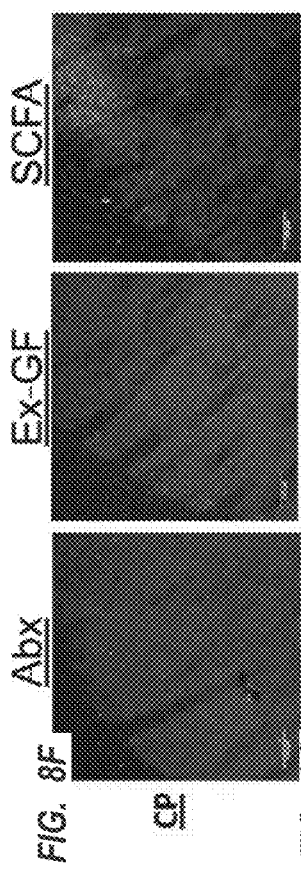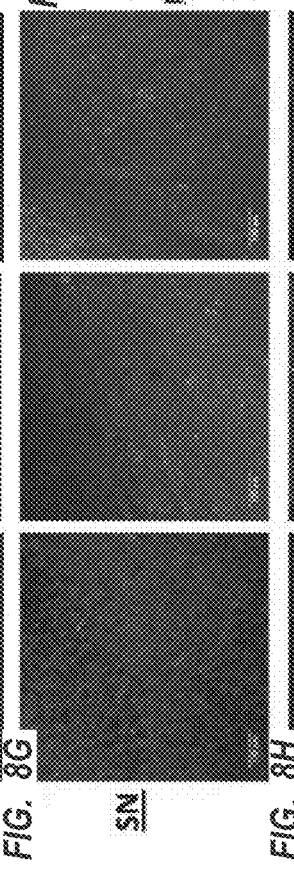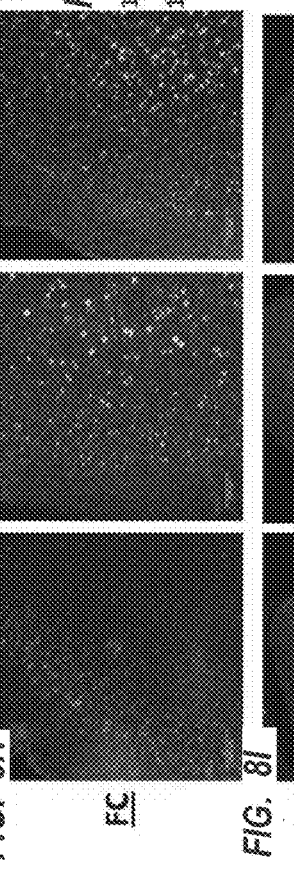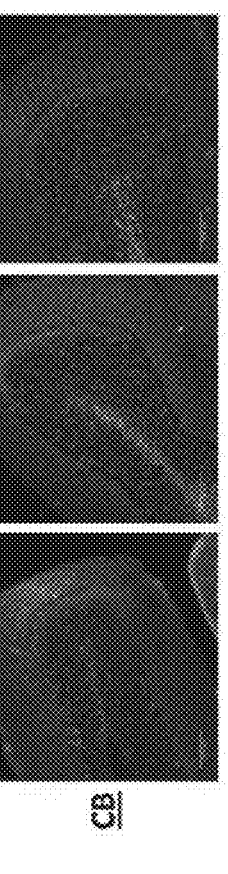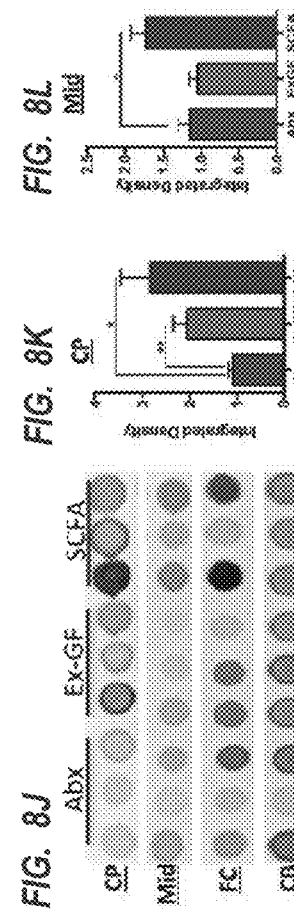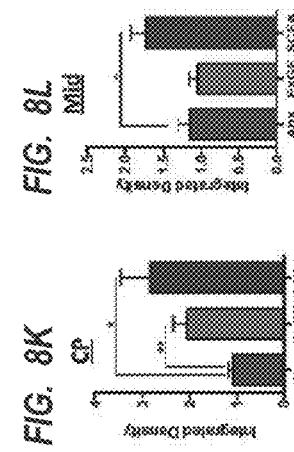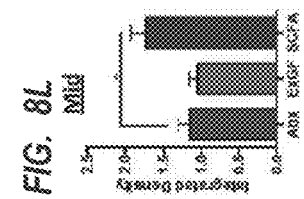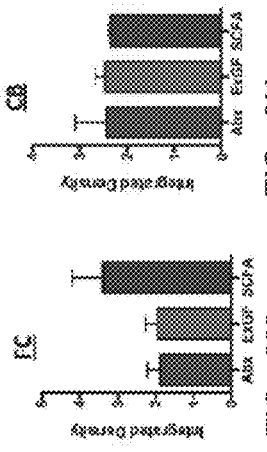

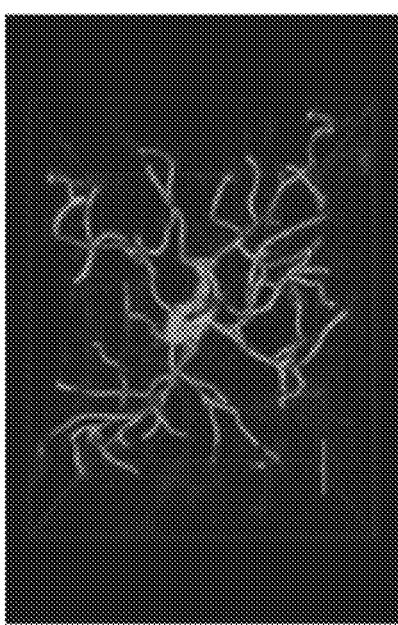
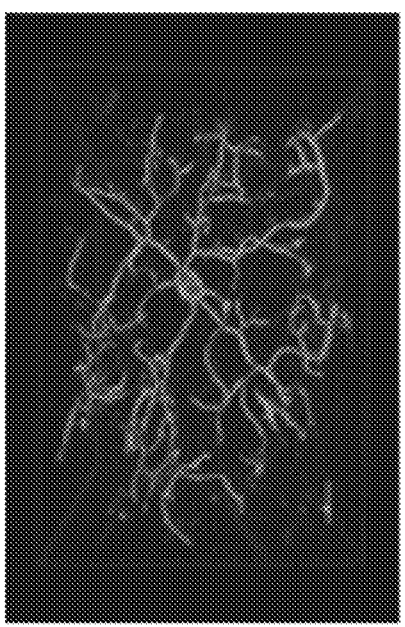
FIG. 9A
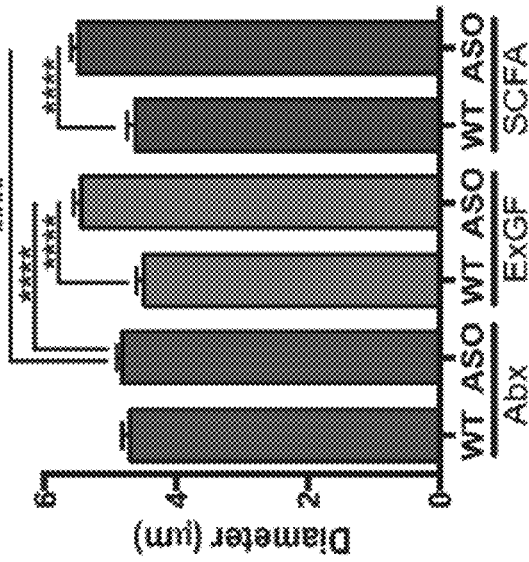
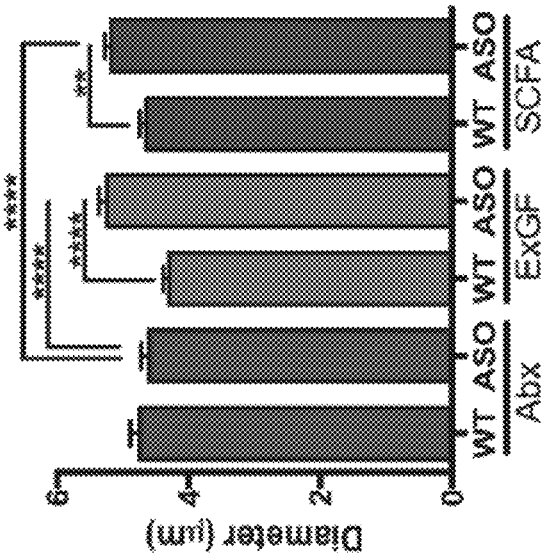
FIG. 9B

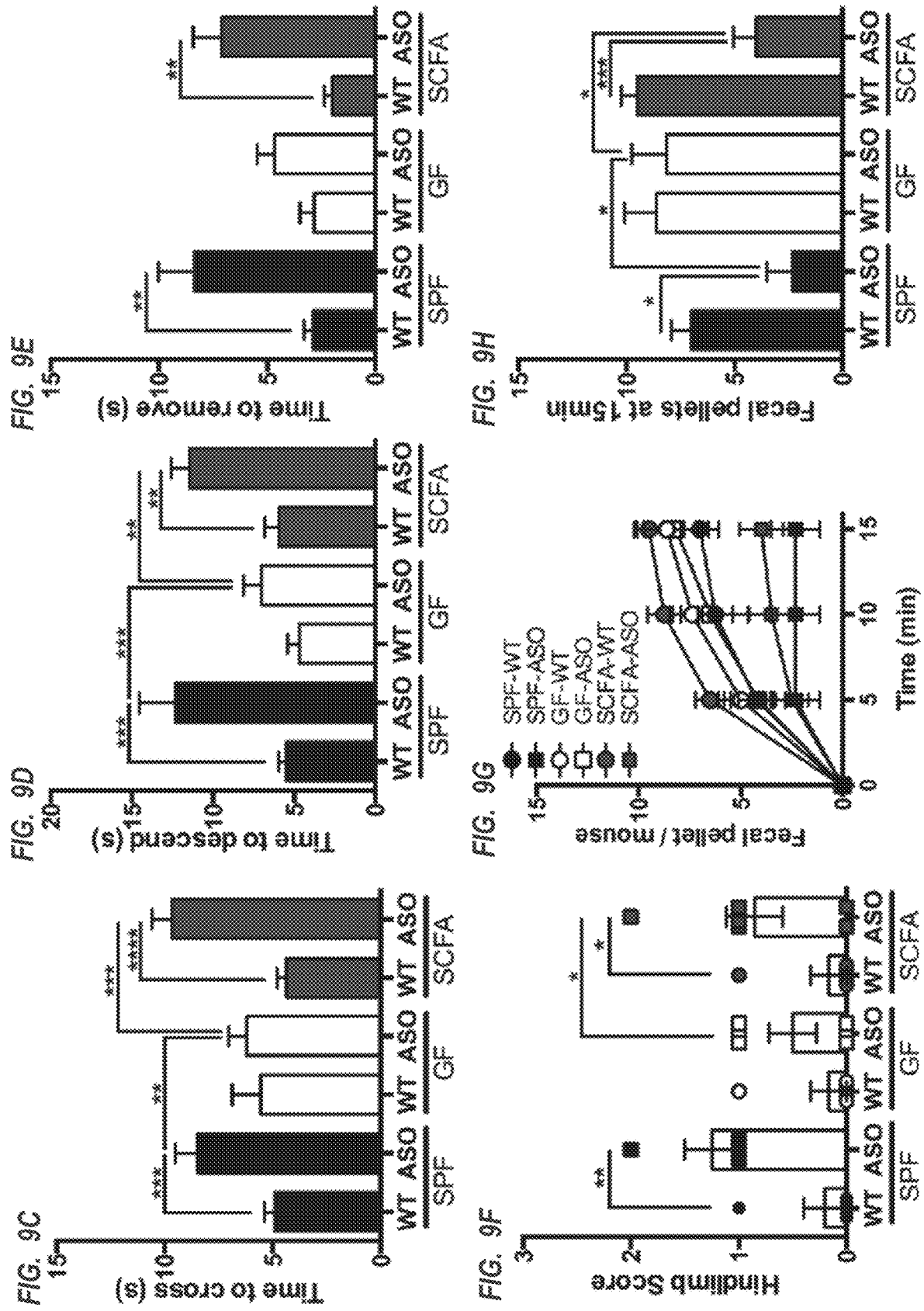

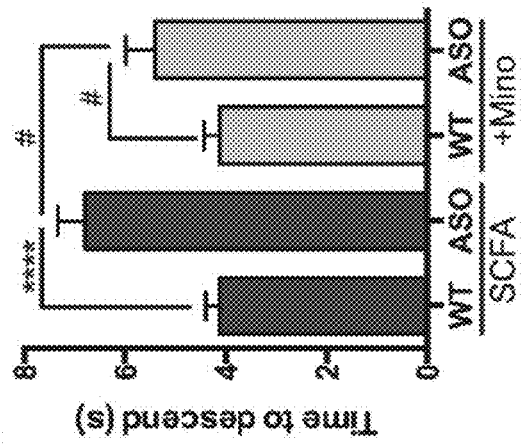
FIG. 11D
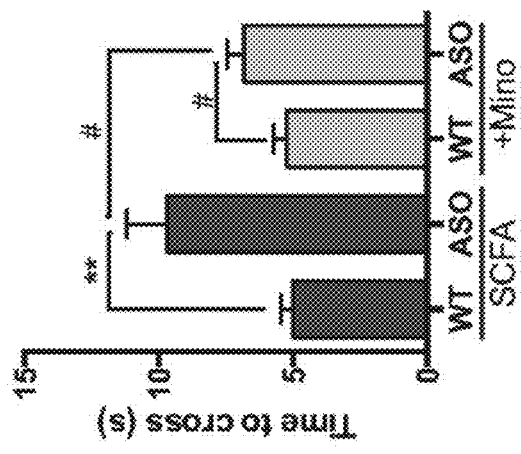
FIG. 11E
FIG. 11F
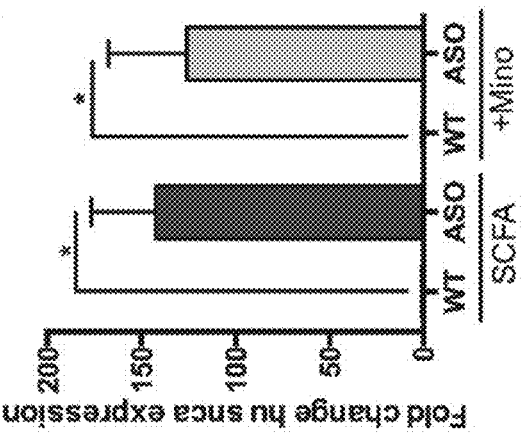
FIG. 11G
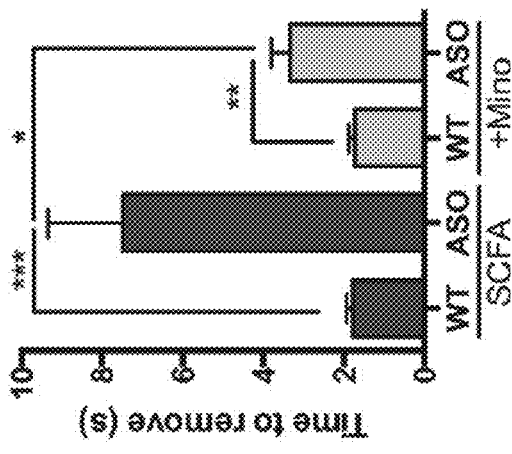
FIG. 11H
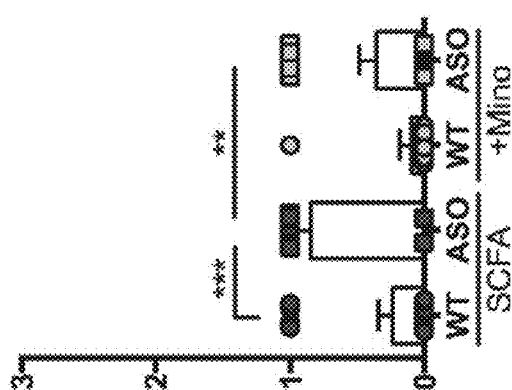

FIG. 13D
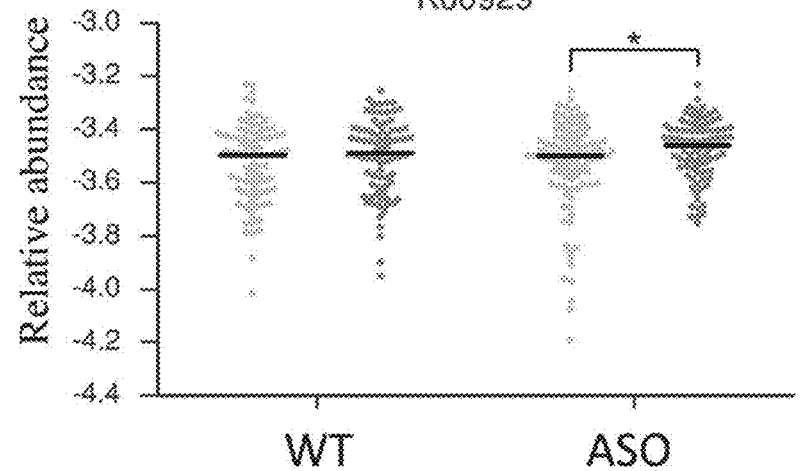
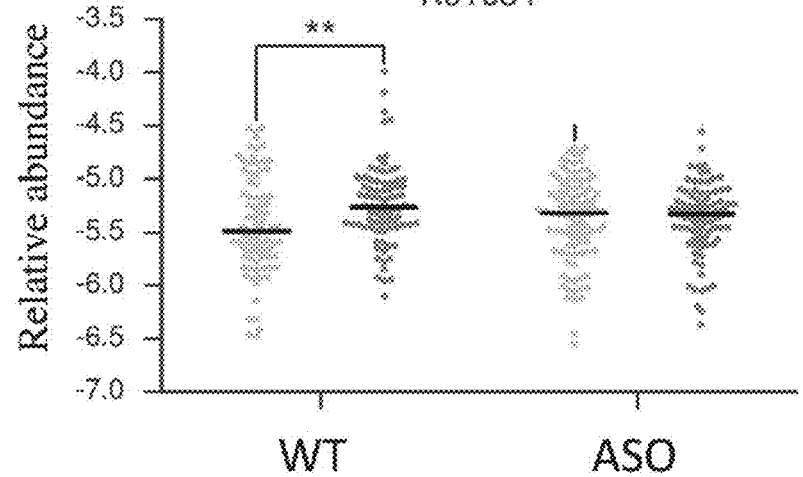
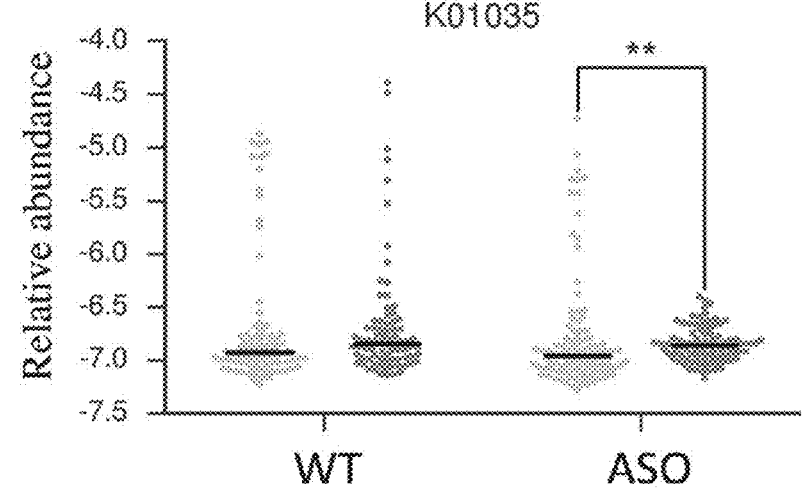

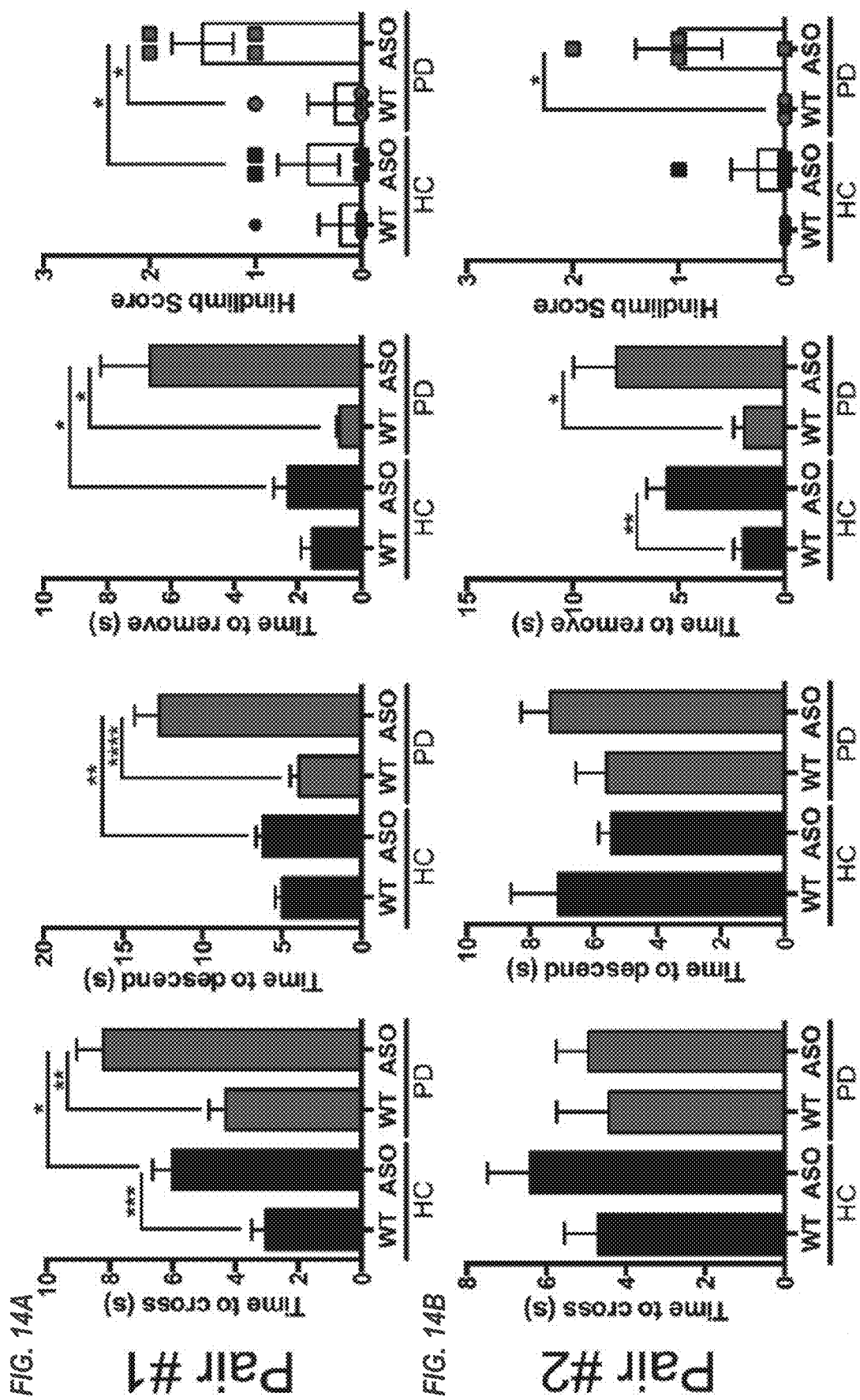

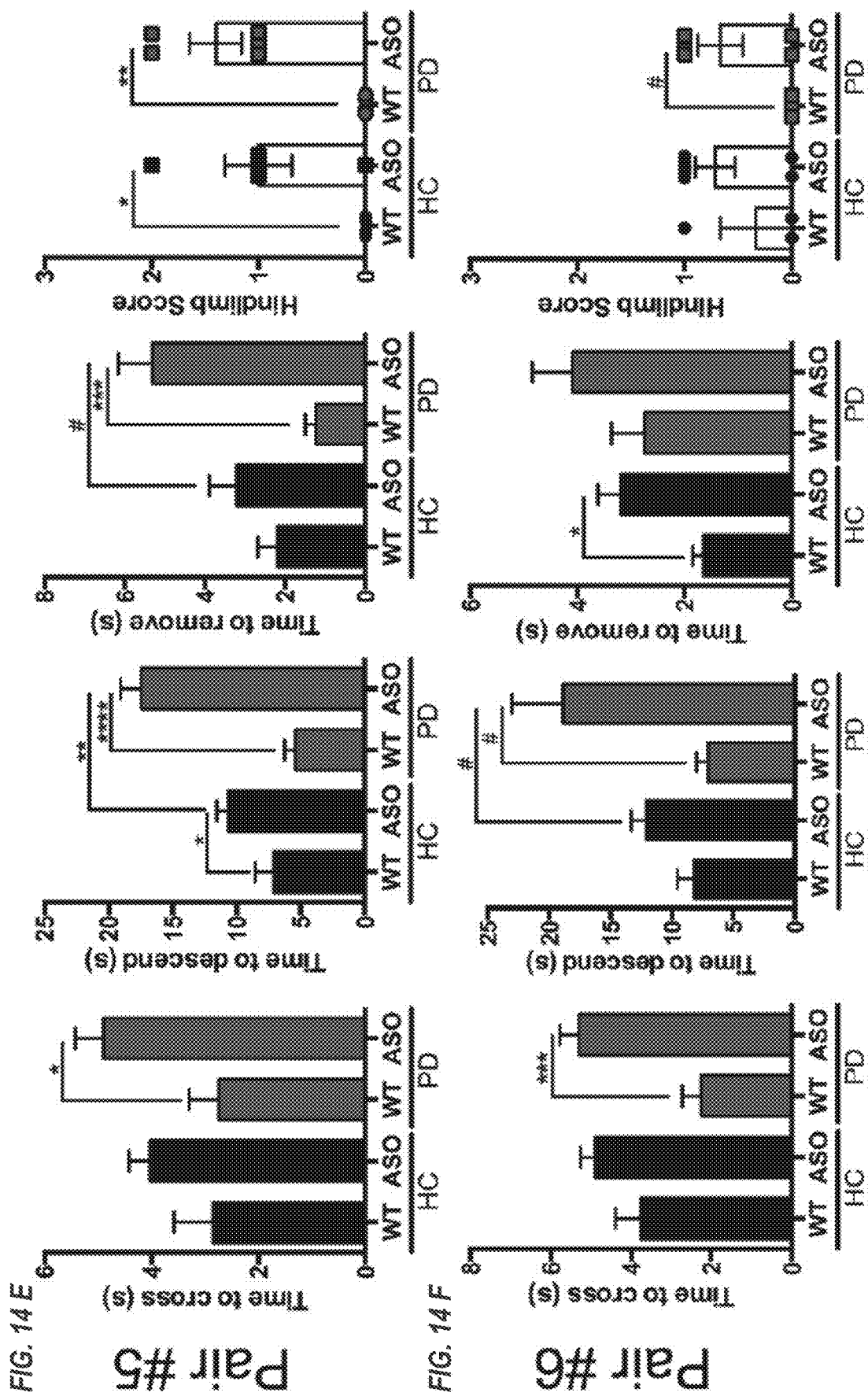

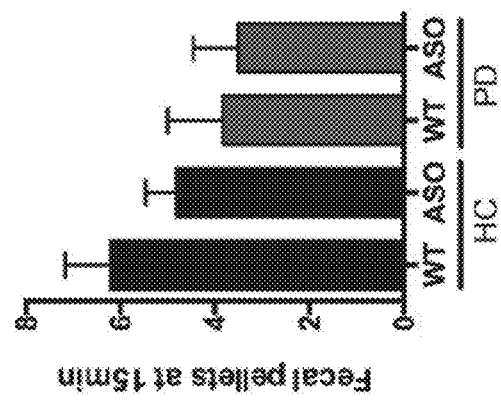
FIG. 15A
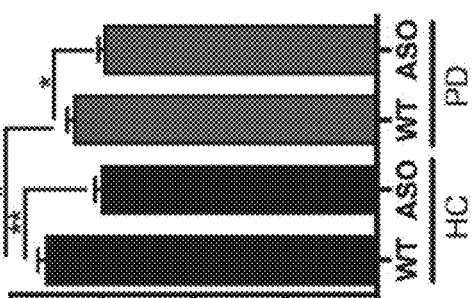
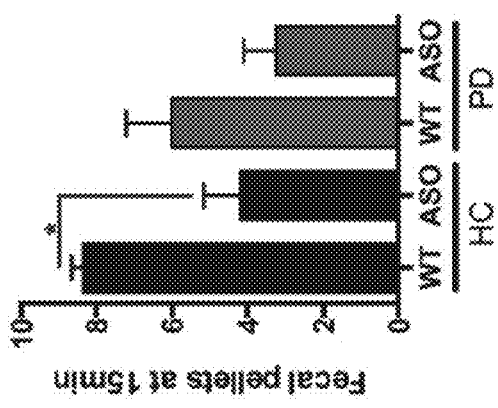
FIG. 15C
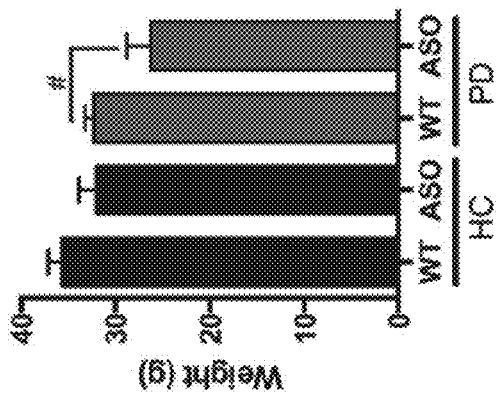
FIG. 15D
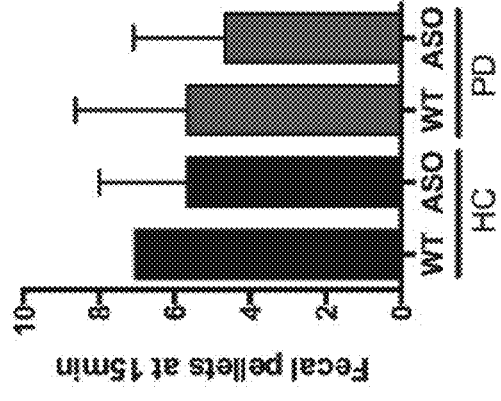
FIG. 15B
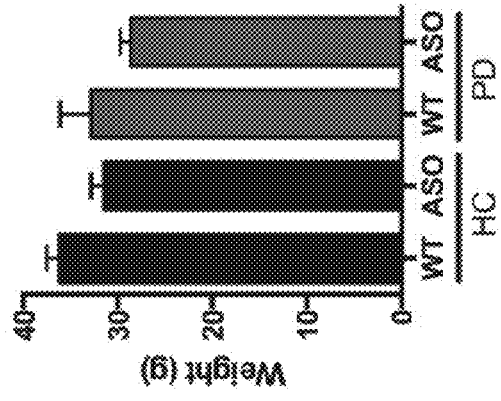
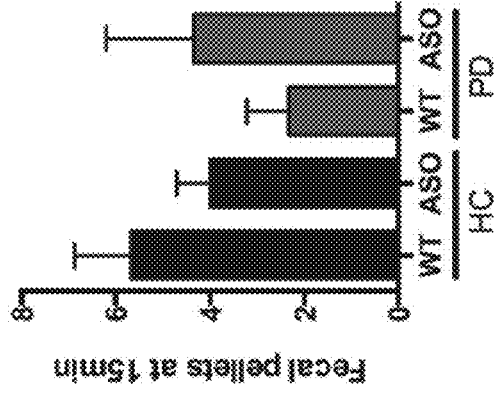
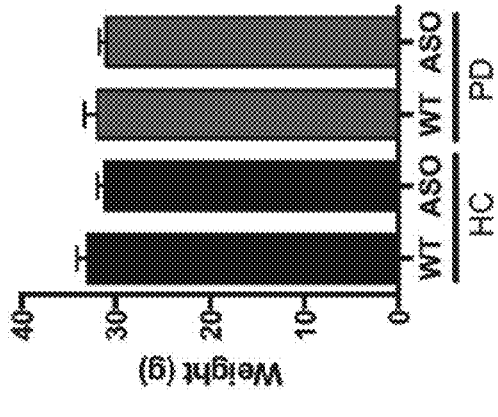

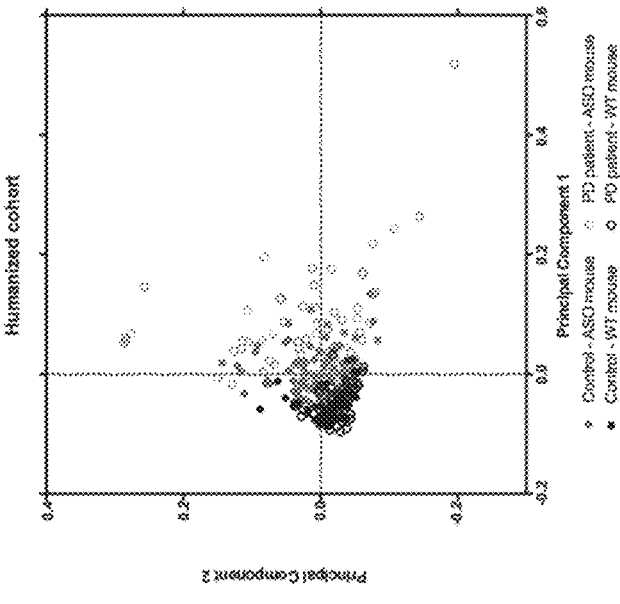
FIG. 15G
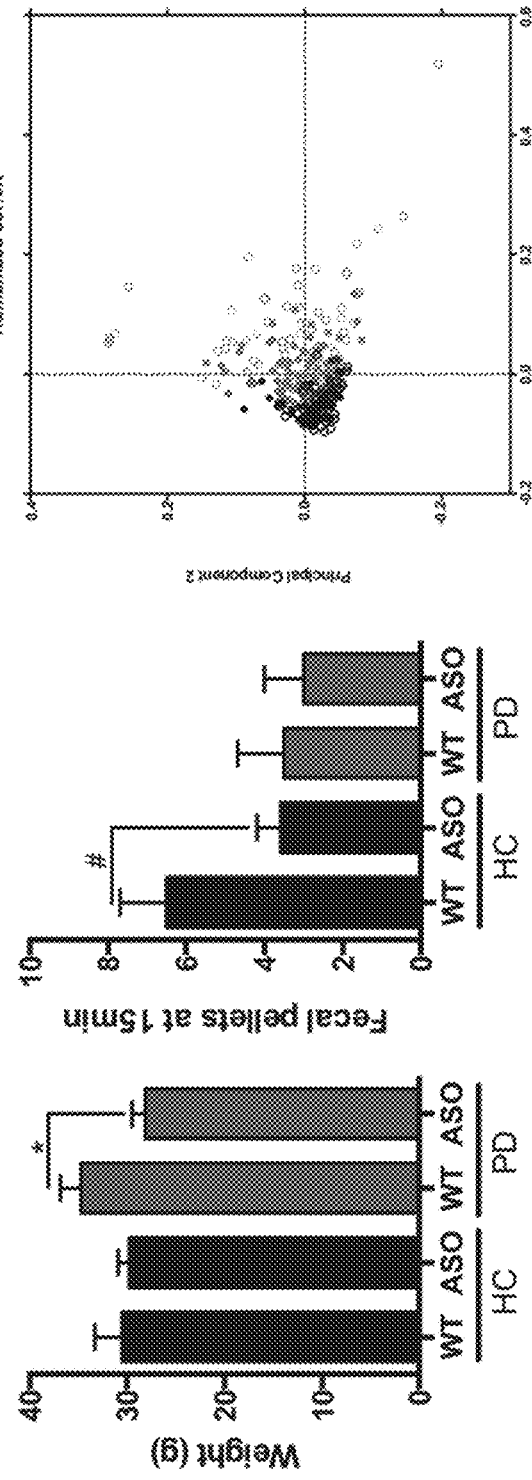
FIG. 15E
FIG. 15F
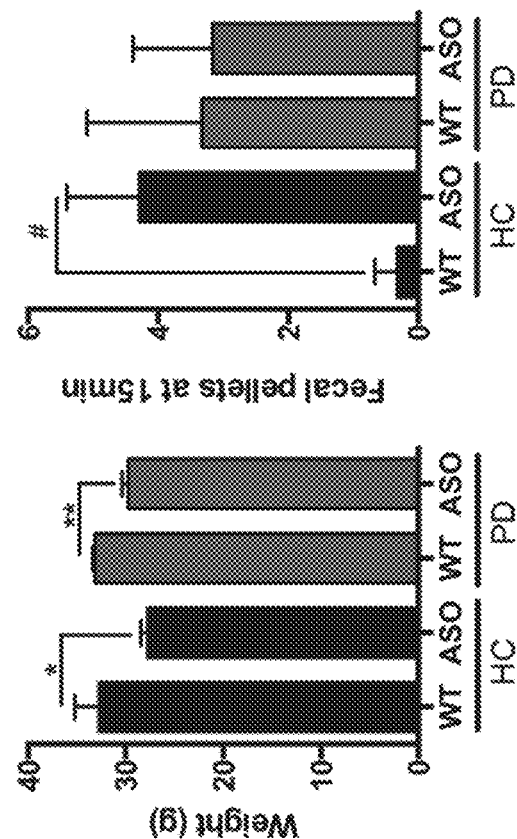

REGULATE GUT MICROBIOTA TO TREAT NEURODEGENERATIVE DISORDERS

RELATED APPLICATIONS

The present application is a continuation of U.S patent application Ser. No. 16/302,321, filed Nov. 16, 2018, which is a U.S. National Phase of International Application No. PCT/US2017/033881, filed May 22, 2017, which claims priority under 35 U.S.C. § 119(e) to U.S. Provisional Application No. 62/340,408 filed on May 23, 2016, U.S. Provisional Application No. 62/370,578 filed on Aug. 3, 2016, and U.S. Provisional Application No. 62/443,952 filed on Jan. 9, 2017, each of which is incorporated herein by reference in its entirety.

The present application is being filed along with a Sequence Listing in electronic format. The Sequence Listing is provided as a file entitled CALTE119C1_SEQUENCE.XML, created Jun. 14, 2023, which is 16,108 bytes in size. The information in the electronic format of the Sequence Listing is incorporated herein by reference in its entirety.

STATEMENT REGARDING FEDERALLY SPONSORED R&D

This invention was made with government support under grant no. NS085910 awarded by the National Institutes of Health. The government has certain rights in the invention.

BACKGROUND

Field

The present disclosure relates generally to the field of diagnosing and treating neurodegenerative disorders, for example Parkinson's disease.

Description of the Related Art

Neurological dysfunction is the basis of numerous human diseases. Behavioral, psychiatric, and neurodegenerative disorders often display hallmark neuropathologies within the central nervous system (CNS). One neuropathology, amyloidosis, results from aberrant aggregation of specific neuronal proteins that disrupt many cellular functions. Affected tissues often contain insoluble aggregates of proteins that display altered conformations, a feature believed to contribute to an estimated 50 distinct human diseases (Sacchettini and Kelly, 2002). Neurodegenerative amyloid disorders, including Alzheimer's, Huntington's, and Parkinson's diseases (PD), are associated with various distinct amyloid proteins (Brettschneider et al., 2015). PD is the second most common neurodegenerative disease in the United States, affecting an estimated 1 million people and 1% of the US population over 60 years of age (Nalls et al., 2014). Worldwide, about 3 million patients and caregivers suffer from the often-debilitating symptoms of PD, which involve motor deficits including tremors, muscle rigidity, bradykinesia, and impaired gait. It is a multifactorial disorder that has a strong environmental component, as less than 10% of cases are hereditary (Nalls et al., 2014). Aggregation of α-synuclein (αSyn) is thought to be pathogenic in a family of diseases termed synucleinopathies, which includes PD, multiple system atrophy, and Lewy body disease (Brettschneider et al., 2015; Luk et al., 2012; Prusiner et al., 2015). αSyn aggregation is a stepwise process, leading to oligomeric species and intransient fibrils that accumulate within neurons. Dopaminergic neurons of the substantia nigra pars compacta (SNpc) appear particularly vulnerable to effects of αSyn aggregates. Dopamine modulators are a first-line therapeutic in PD; however, treatments can carry serious side effects and often lose effectiveness (Jenner, 2008). Discovery of safe and effective therapeutics are needed to address the increasing burden of PD in an ever-aging population, a paradoxical consequence of mankind's achievements in increased lifespan.

SUMMARY

Disclosed herein are methods and compositions that can be used to improve motor deficits and neuroinflammation in subjects in need, for example subjects suffering from neurodegenerative disorders (e.g., Parkinson's disease). Also disclosed are methods and compositions that can be used to diagnose neurodegenerative disorders, such as Parkinson's disease.

Some embodiments provide methods for treating a neurodegenerative disorder in a subject, where the methods comprise adjusting the composition of gut microbiota in a subject in need, wherein the subject in need is suffering from a neurodegenerative disorder. Some embodiments provide methods for delaying or reducing the likelihood of onset of a neurodegenerative disorder in a subject, where the method comprise adjusting the composition of gut microbiota in a subject in need, wherein the subject in need is at a risk of developing a neurodegenerative disorder. In some embodiments, the neurodegenerative disorder is a synucleinopathy, for example Parkinson's disease (PB), dementia with Lewy body disease, multiple system atrophy, or any combination thereof.

Some embodiments provide methods for improving a motor deficit in a subject in need (for example, a subject having a synucleinopathy (including Parkinson's disease)), where the methods comprise adjusting the composition of gut microbiota in the subject. Some embodiments provide a method for reducing microglia activation in a subject in need, where the method comprises adjusting the composition of gut microbiota in the subject. Some embodiments provide a method for reducing α-synuclein (αSyn) aggregates in a subject in need, where the method comprises adjusting the composition of gut microbiota in the subject. In some embodiments, the method promotes clearance of insoluble αSyn protein aggregates, reduces aggregation of αSyn protein, or both. In some embodiments, the method comprises measuring the rate and/or level of αSyn aggregation in the subject, measuring the clearance rate and/or level of insoluble αSyn protein aggregate in the subject, or a combination thereof. In some embodiments, the rate and/or level of αSyn aggregation in the brain of the subject, the clearance rate and/or level of insoluble αSyn protein aggregate in the brain the subject, or a combination thereof is measured. In some embodiments, the method further comprises measuring the rate and/or level of αSyn aggregation in the subject, measuring the clearance rate and/or level of insoluble αSyn protein aggregate in the subject, or a combination thereof after adjusting the composition of gut microbiota in the subject Some embodiments provide a method for reducing neuroinflammation in a subject in need, where the method comprises adjusting the composition of gut microbiota in the subject.

The subject in need in the methods disclosed herein can be, for example, a subject suffering from a neurodegenerative amyloid disorder, for example a synucleinopathy. Non-limiting examples of synucleinopathy include Parkinson's disease, dementia with Lewy body disease, multiple system atrophy, and any combination thereof. In some embodiments, the subject in need is a subject suffering from Parkinson's disease. In some embodiments, the methods disclosed herein can further comprise identifying a subject in need, wherein the subject in need has an abnormal level of aggregation of α-synuclein (αSyn). In some embodiment, identifying the subject in need comprises measuring the rate and/or level of αSyn aggregation in the subject, measuring the clearance rate and/or level of insoluble αSyn protein aggregate in the subject, or a combination thereof. In some embodiment, the rate and/or level of αSyn aggregation in the brain of the subject, the clearance rate and/or level of insoluble αSyn protein aggregate in the brain the subject, or a combination thereof is measured. In some embodiment, the method further comprises measuring the rate and/or level of αSyn aggregation in the subject, measuring the clearance rate and/or level of insoluble αSyn protein aggregate in the subject, or a combination thereof after adjusting the composition of gut microbiota in the subject. In some embodiment, the method improves one or more physical impairments in the subject. In some embodiment, the method improves one or more GI functions of the subject. In some embodiment, the method relieves constipation of the subject. In some embodiment, the motor deficit is tremors, muscle rigidity, bradykinesia, impaired gait, or any combination thereof.

The methods disclosed herein can, in some embodiments, restore the composition of the gut microbiota in the subject to a normal level. In some embodiments, adjusting the composition of the gut microbiota in the subject comprises administering one or more antibiotics to the subject. The antibiotics can be natural, synthetic, or semi-synthetic. The one or more antibiotics can comprise, for example, ampicillin, vancomycin, neomycin, gentamycin, erythromycin, teicoplanin, doxycycline, tetracycline, norfloxacin, ciprofloxacin, augmentin, cephalexin (e.g., Keflex), penicillin, ampicillin, kanamycin, rifamycin, rifaximin, neomycin, metronidazole, or any combination thereof. The antibiotic may be administered orally, intravenously, rectally, or a combination thereof. In some embodiments, the one or more antibiotics do not comprise rifampicin and/or minocycline. In some embodiments, adjusting the composition of the gut microbiota in the subject comprises administering to the subject an inhibitor of one or more PD-enhancing microbial metabolites. In some embodiments, adjusting the composition of the gut microbiota in the subject comprises administering to the subject an antibody against one or more PD-enhancing microbial metabolites, an antibody against an intermediate for the in vivo synthesis of one or more PD-enhancing microbial metabolites, or an antibody against a substrate for the in vivo synthesis of one or more PD-enhancing microbial metabolites.

In some embodiments, adjusting the composition of the gut microbiota in the subject comprises administering to the subject an inhibitor of an enzyme involved in the in vivo synthesis of one or more PD-enhancing microbial metabolites. The one or more PD-enhancing microbial metabolites can comprise, for example, one or more fatty acids, salt or ester thereof, or any combination thereof. In some embodiments, the one or more PD-enhancing microbial metabolites comprise one or more short-chain fatty acids (SCFAs), salt or ester thereof, or any combination thereof. In some embodiments, the one or more PD-enhancing microbial metabolites comprise one or more medium-chain fatty acids, one or more long-chain fatty acids, salt or ester of medium-chain fatty acids, salt or ester of long-chain fatty acids, or any combination thereof. In some embodiments, the one or more PD-enhancing microbial metabolites comprise SCFAs acetate, SCFAs propionate, SCFAs butyrate, or any combination thereof.

In some embodiments, adjusting the composition of the gut microbiota in the subject comprises enhancing the level of one or more PD-protective bacterial species in the subject. In some embodiments, adjusting the composition of the gut microbiota in the subject comprises administering to the subject a composition comprising one or more PD-protective bacterial species. At least one of the one or more PD-protective bacterial species can belong to, for example, Lachnospiraceae, Rikenellaceae, Peptostreptococcaceae, Clostridiaceae, *Enterococcus, Clostridium, Bacteroides,* or *Butyricicoccus* sp. family. In some embodiments, the composition is a probiotic composition, a nutraceutical composition, a pharmaceutical composition, or any combination thereof.

In some embodiments, adjusting the composition of the gut microbiota in the subject comprises fecal transplantation, microbiota conventionalization, microbial colonization, reconstitution of gut microbiota, probiotic treatment, or a combination thereof. In some embodiments, adjusting the composition of the gut microbiota in the subject comprises reducing the level of one or more PD-enhancing bacterial species in the subject. At least one of the one or more PD-enhancing bacterial species can belong to, for example, *Proteus* sp., *Bilophila* sp., *Roseburia* sp., *Pseudoramibacter Eubacterium*, or Veillonellaceae family. In some embodiments, at least one of the one or more PD-enhancing bacterial species is a SCFA-producing bacterium. Non-limiting examples of SCFA-producing bacteria include bacteria belonging to KEGG family K00929, K01034, and K01035.

In some embodiments, adjusting the composition of the gut microbiota in the subject comprises introducing gut microbiota from a healthy subject to the subject being treated.

Some embodiments provide a method for treating a neurodegenerative disorder in a subject, where the methods comprise one or more of: administering an antibiotic to the subject; and administering to the subject an inhibitor of PD-enhancing microbial metabolite. Some embodiments provide methods for delaying or reducing the likelihood of onset of a neurodegenerative disorder in a subject, where the methods comprise one or more of: administering an antibiotic to the subject; and administering to the subject an inhibitor of PD-enhancing microbial metabolite. The neurodegenerative disorder can be, for example, a synucleoinopthy (e.g., Parkinson's disease, dementia with Lewy body disease, multiple system atrophy, or a combination thereof).

Some embodiments provide methods of improving a parkinsonian symptom in a subject in need, where the methods comprise one or more of: administering an antibiotic to the subject; administering an anti-inflammatory agent to the subject; and administering to the subject an inhibitor of one or more PD-enhancing microbial metabolites. In some embodiments, the anti-inflammatory agent and the antibiotic is not minocycline. In some embodiments, the parkinsonian symptom comprises an impaired motor function, enhanced α-synuclein (αSyn) aggregation, abnormal microglia activation, or any combination thereof. In some embodiments, the parkinsonian symptom comprises tremor, bradykinesia, muscle rigidity, impaired posture and balance, loss of automatic movements, speech impairment, writing impairment, or any combination thereof. In some embodiments, the inhibitor of PD-enhancing microbial metabolite is an antibody against one or more PD-enhancing microbial metabolites, an antibody against an intermediate for the in vivo synthesis of one or more PD-enhancing microbial metabolites, an antibody against a substrate for the in vivo synthesis of one or more PD-enhancing microbial metabolites, an inhibitor of an enzyme involved in the in vivo synthesis of one or more PD-enhancing microbial metabolites, or a combination thereof. In some embodiments, the subject or the subject in need is not receiving an antibiotic treatment. In some embodiments, the method does not comprise administering the subject or the subject in need any antibiotics. In some embodiments, the subject or the subject in need is not being treated with rifampicin and/or minocycline. In some embodiments, the subject or the subject in need did not receive any antibiotic treatment at least 12 hours, 1 day, 5 days, 10 days, or 20 days before being adjusted of gut microbiota composition or other treatment. In some embodiments, the subject or the subject in need does not receive any antibiotic treatment at least 12 hours, 1 day, 5 days, 10 days, or 20 days after being adjusted of gut microbiota composition or other treatment. In some embodiments, the method further comprises determining the presence and/or level of one or more PD-associated bacterial species in the subject to identify a subject in need.

Some embodiments provide methods of diagnosing parkinsonism in a subject, where the methods comprise determining the presence and/or level of one or more PD-associated bacterial species in the subject, whereby the presence and/or abnormal level of the one or more PD-associated bacterial species indicates that the subject has a risk of developing, or is suffering from a symptom of parkinsonism. In some embodiments, at least one of the one or more PD-associated bacterial species belonging to *Proteus* sp., *Bilophila* sp., *Roseburia* sp., *Pseudoramibacter Eubacterium*, or Veillonellaceae family. In some embodiments, the presence and/or level of one or more PD-associated bacterial species is determined in the gut of the subject. In some embodiments, the presence and/or abnormal level of the one or more PD-associated bacterial species indicates that the subject has a risk of developing parkinsonism. In some embodiments, the presence and/or abnormal level of the one or more PD-associated bacterial species indicates that the subject is suffering from parkinsonism. In some embodiments, the parkinsonism is a primary or idiopathic parkinsonism, secondary or acquired parkinsonism, hereditary parkinsonism, Parkinson plus syndromes or multiple system degeneration, or any combination thereof. In some embodiments, the parkinsonism is Parkinson's disease. In some embodiments, the subject is an adult.

Some embodiments provide compositions comprising one or more PD-protective bacterial species. In some embodiments, the compositions do not comprise PD-enhancing bacterial species. In some embodiments, at least one of the one or more PD-protective bacterial species belongs to Lachnospiraceae, Rikenellaceae, Peptostreptococcaceae, Clostridiaceae, *Enterococcus, Clostridium, Bacteroides*, or *Butyricicoccus* sp. family. In some embodiments, the composition does not comprise bacterial species belong to at least one of *Proteus* sp., *Bilophila* sp., *Roseburia* sp., *Pseudoramibacter Eubacterium*, and Veillonellaceae family. In some embodiments, the composition does not comprises bacterial species belong to *Proteus* sp., *Bilophila* sp., *Roseburia* sp., *Pseudoramibacter Eubacterium*, and Veillonellaceae family. In some embodiments, the composition does not comprise pathogenic Clostridia bacteria. In some embodiments, at least one of the one or more PD-protective bacterial species is viable bacteria. In some embodiments, the one or more PD-protective bacterial species are viable bacteria. The composition can be, for example, a probiotic composition, a nutraceutical composition, a pharmaceutical composition, or any combination thereof. In some embodiments, the composition is a pharmaceutical composition comprising one or more pharmaceutically acceptable carriers Some embodiments provide pharmaceutical compositions comprising an inhibitor of a PD-enhancing microbial metabolite, and one or more pharmaceutically acceptable carriers. The PD-enhancing microbial metabolite can be any microbial metabolite, for example, a fatty acid, or a salt or ester thereof. In some embodiments, the PD-enhancing microbial metabolite is a short-chain fatty acid (SCFA), a medium-chain fatty acid, a long-chain fatty acid, a salt or ester of a short-chain fatty acid, a salt or ester of a medium-chain fatty acid, or a salt or ester of a long-chain fatty acid. The inhibitor of PD-enhancing microbial metabolite can be, for example, an antibody against the PD-enhancing microbial metabolite, an antibody against an intermediate for the in vivo synthesis of the PD-enhancing microbial metabolite, an antibody against a substrate for the in vivo synthesis of the PD-enhancing microbial metabolite, an inhibitor of an enzyme involved in the in vivo synthesis of the PD-enhancing microbial metabolite, or a combination thereof

BRIEF DESCRIPTION OF THE DRAWINGS

FIG. 2A shows that ASO animals harboring aA complex microbiota (SPF-ASO) required significantly more time to cross a challenging beam compared to wild-type littermates (SPF-WT), measure of gross motor function. FIG. 2B shows that ASO animals harboring a complex microbiota exhibited increased time to descend a pole compared to wild-type littermates, another measure of gross motor function. FIG. 2C shows that removal of an adhesive from the nasal bridge, a test of fine motor control, was impaired in SPF-ASO mice compared to SPF-WT mice. FIG. 2D shows that the hindlimb clasping reflex, a measure of striatal dysfunction, was defective in SPF-ASO mice. FIGS. 2A-2D also show that 12- to 13-week-old ASO mice (GF-ASO) and wild-type mice (GF-WT) re-derived under germ-free conditions exhibited reduced deficits in beam traversal, pole descent, adhesive removal, and hindlimb clasping. FIGS. 2E-2F show that in SPF-ASO animals, a marked decrease in the total output of fecal pellets, at 12-13 weeks of age, was observed while fecal output was unaltered in GF-ASO animals. FIG. 2E shows time course of fecal output in a novel environment over 15 min. FIG. 2F shows total fecal pellets produced in 15 min. See also FIGS. 3A-3K.

FIGS. 3A-3K show that body weight of SPF and GF animals, and analysis of aged mice (related to FIGS. 2A-2F). N=4-6, error bars represent the mean and standard error. From 3 trials per animal for motor tests. Data are representative of 2 experiments. $0.1>p>0.05$; $*p\leq0.05$; $p\leq0.01$; $*p\leq0.001$; $****p\leq0.0001$. SPF=specific-pathogen free, GF=germ-free, WT=wild-type, ASO=Thy1-α-synuclein genotype. FIG. 3A shows that 12- to 13-week-old GF-ASO mice did not exhibit differences in weight compared to 12- to 13-week-old SPF-ASO animals. FIG. 3B shows that both SPF-ASO and GF-ASO animals displayed defects in the inverted grid assay, a measure of limb strength based on the time to fall from an inverted grid. FIGS. 3C-3G show that at a later age (24-25 weeks old), SPF-ASO animals exhibited a progressive decline in motor function, which was significantly delayed in GF-ASO animals. FIG. 3C shows time to traverse beam by 24-25 week old animals. FIG. 3D shows time to descend pole by 24-25 week old animals. FIG. 3E shows time to removal adhesive from nasal bridge by 24-25 week old animals. FIG. 3F shows hindlimb clasping reflex scores by 24-25 week old animals. FIG. 3G shows body weight of 24-25 week old animals. FIGS. 3H-3I show that in SPF-ASO animals, a marked decrease in the total output of fecal pellets, at 24-4513 weeks of age, was observed while fecal output was unaltered in GF-ASO animals (3H, and 3I). FIG. 3H shows time course of fecal output in a novel environment over 15 min by 24-25 week old animals. FIG. 3I shows total fecal pellets produced in 15 min by 24-25 week old animals. FIG. 3J shows that fecal pellets produced by 12- to 13-week-old SPF-ASO mice contained reduced water content compared to 12- to 13-week-old GF-ASO mice, revealing reduced GI defects in GF animals. FIG. 3K shows Principle Component Analysis (PCoA) compiling all motor function scores from SPF-WT, SPF-ASO, GF-WT, and GF-ASO cohorts. Compilation of all motor phenotypes into a principal-component analysis displayed a striking segregation by the SPF-ASO group, while GF-ASO animals clustered more similarly to WT mice.

FIGS. 4A-4G show that αSyn pathology is increased in mice harboring a gut microbiota. Tissues collected from mice at 12-13 weeks of age. n=3-4, error bars represent the mean and standard error. $*p\leq0.05$; $p\leq0.01$; $*p\leq0.001$. Abbreviations: SPF, specific-pathogen-free; GF, germ-free; WT, wild-type; ASO, Thy1-α-synuclein genotype. See also FIGS. 5A-5H. FIGS. 4A and 4B show that under SPF conditions, notable aggregation of αSyn in the caudoputamen (CP) and substantia nigra (SN) of ASO animals was observed. FIG. 4A show representative images of the caudoputamen (CP) rom SPF-ASO or GF-ASO animals stained with aggregation-specific αSyn antibody, Phospho-Ser129-αSyn antibody, and Neurotrace/Nissl. FIG. 4B shows representative images of the substantia nigra (SN) from SPF-ASO or GF-ASO animals, stained as above. FIG. 4C is a representative western blot of triton soluble and insoluble brain homogenates, immunostained with anti-αSyn antibody to quantify αSyn aggregation. FIGS. 4D and 4E show significantly less insoluble αSyn in brains of GF-ASO animals was observed. FIG. 4D shows densitometry quantification of anti-αSyn western blots for all αSyn staining. FIG. 4E shows densitometry quantification of anti-αSyn western blots for ratios of insoluble to soluble αSyn staining. FIGS. 4F and 4G show that levels of αSyn transcript and protein in the inferior midbrain and the CP between SPF- and GF-ASO animals were determined to be similar. FIG. 4F shows qRT-PCR analysis of human αSyn in the CP or inferior midbrain (Mid). FIG. 4G shows ELISA analysis of total αSyn present in homogenates from the CP or inferior midbrain (Mid).

FIGS. 5A-5I show gut microbes promote regional-specific αSyn pathology (related to FIGS. 4A-2G and 6A-6H). Animals were tested at 12-13 weeks of age. N=3-4, error bars represent the mean and standard error. $*p\leq0.05$. SPF=specific pathogen free, GF=germ-free, WT=wild-type, ASO=Thy1-α-synuclein genotype. FIGS. 5A-5C show that, compared to FIGS. 4C-4E, similarly decreased αSyn aggregation in GF-ASO animals was observed. FIG. 5A shows aggregate-specific αSyn dot blots derived from caudoputamen (CP) and inferior midbrain (Mid) homogenates from SPF-ASO and GF-ASO animals. FIGS. 5B and 5C show densitometry quantification of dot blots of the (B) CP or (C) inferior midbrain. FIGS. 5D-5H show regional specificity of αSyn aggregation was observed: in the frontal cortex (FC), GF-ASO animals harbor fewer αSyn aggregation than SPF animals, while in the cerebellum (CB), nearly equal quantities of αSyn in SPF and GF mice were observed. FIG. 5D shows representative images of the frontal cortex (FC) from SPF-ASO or GF-ASO animals stained with aggregation-specific αSyn antibody, Phospho-Ser129-αSyn antibody, and Neurotrace/Nissl. FIG. 5E shows representative images of the cerebellum (CB) from SPF-ASO or GF-ASO animals, stained as above. FIG. 5F shows dot blot images of homogenates from the FC or CB from SPF-ASO and GF-ASO animals, immunostained with aggregation-specific αSyn antibody. FIGS. 5G and 5H show densitometry quantification of dot blots from the (G) FC and (H) CB. FIG. 5I shows that neuroprotective Bdnf and the cell cycle marker Ddit4 levels were upregulated in GF animals using qPCR analysis of CD11b+ cells derived from brain homogenate for bdnf and ddit4.

FIGS. 6A-6H shows αSyn-dependent microglia activation by the microbiota. Tissues collected from mice at 12-13 weeks of age. n=3-4 (with 20-60 cells per region per animal analyzed); error bars represent the mean and standard error. $*p\leq0.05$; $p\leq0.01$; $*p\leq0.001$; $****p\leq0.0001$. Abbreviations: SPF, specific-pathogen-free; GF, germ-free; WT, wild-type; ASO, Thy1-α-synuclein genotype. See also FIGS. 5A-5I. FIGS. 6A-6C show that within the CP and SN, microglia in GF-WT mice displayed increased numbers and total lengths of microglia branches compared to SPF-WT animals. FIG. 6A shows representative 3D reconstructions of Iba1-stained microglia residing in the caudoputamen (CP) of SPF-WT, SPF-ASO, GF-WT, and GF-ASO animals. FIG. 6B shows CP-resident microglia parameters diameter, number of branch points, and total branch length. FIG. 6C shows substantia nigra (SN)-resident microglia parameters diameter, number of branch points, and total branch length. FIGS. 6D and 6E show that tissue homogenates from the CP and inferior midbrain of SPF-ASO mice contained a marked increase in the pro-inflammatory cytokines tumor necrosis factor-a (TNF-a) and interleukin-6 (IL-6) compared to GF-ASO mice. FIG. 6D shows ELISA analysis for TNF-a and IL-6 present in homogenates from the CP. FIG. 6E shows ELISA analysis for TNF-a and IL-6 present in homogenates from the inferior midbrain (Mid). FIG. 6F shows that qPCR analysis of CD11b+ cells derived from brain homogenate for tnfa and il6 revealed increased Tnfa and Il6 expression in SPF-ASO animals, which is nearly absent in GF animals. FIGS. 6G and 6H show that neuroinflammatory responses were region specific with increased in microglia diameter and TNF-a production in the FC but not the CB. FIG. 6G shows the diameters of microglia residing in the frontal cortex (FC) or cerebellum (CB). FIG. 6H shows ELISA analysis for TNF-a present in homogenates from the FC or CB.

FIGS. 7A-7I show that postnatal microbial signals promote motor and gastrointestinal dysfunction. Animals were tested at 12-13 weeks of age. n=6-12; error bars represent the mean and standard error from 3 trials per animal, and compiled from 2 independent cohorts or 20-60 microglia per region analyzed. #$0.05<p<0.1$; *$p≤0.05$; $p≤0.01$; *$p≤0.001$; ****$p≤0.0001$. Abbreviations: SPF, specific-pathogen-free; GF, germ-free; Abx, antibiotic-treated; Ex-GF, recolonized germ-free animals; WT, wild-type; ASO, Thy1-α-synuclein genotype. See also FIGS. 8A-8O. FIG. 7A is a time course schema for animal treatment and testing. FIGS. 7B-7E show that antibiotic-treated (Abx) animals displayed little αSyn-dependent motor dysfunction, closely resembling mice born under GF conditions. FIGS. 7B-7E also show that postnatal colonization of previously GF animals (Ex-GF) recapitulated the genotype effect observed in SPF mice, with mice that overexpressed αSyn displaying significant motor dysfunction. FIG. 7B shows time to traverse beam apparatus. FIG. 7C shows time to descend pole. FIG. 7D shows time to remove nasal adhesive. FIG. 7E shows hindlimb clasping reflex score. FIGS. 7F and 7G show that GI function, as measured by fecal output, was also significantly improved in Abx-treated animals, while Ex-GF mice exhibit an αSyn-dependent decrease in total fecal output. FIG. 7F shows time course of fecal output in a novel environment over 15 min. FIG. 7G Total fecal pellets produced in 15 min. FIGS. 7H and 7I show that in the transgenic ASO line, microglia from Ex-GF animals had increased cell body diameters comparable to those in SPF mice. FIGS. 7H and 7I also show that Abx-ASO animals, however, harbored microglia with diameters similar to GF animals. FIG. 7H shows representative 3D reconstructions of Iba1-stained microglia residing in the caudoputamen (CP) of Abx-ASO or Ex-GF-ASO animals. FIG. 7I shows the diameters of microglia residing in the CP or substantia nigra (SN).

FIGS. 8A-8O show SCFA alterations and increased αSyn pathology in Abx, Ex-GF, and SCFA mice (related to FIGS. 7A-7I and 9A-9H). Animals were tested at 12-13 weeks of age. N=3-6, with 20-60 microglia per region analyzed. Error bars represent the mean and standard error. *$p≤0.05$; $p≤0.01$; *$p≤0.001$; ****$p≤0.0001$. Abbreviations: SPF=specific pathogen free, GF=germ-free, Abx=antibiotic-treated animals, Ex-GF=recolonized germ-free animals, SCFA=short-chain fatty acid-treated animals, WT=wild-type, ASO=Thy1-α-synuclein genotype. FIG. 8A shows that lower fecal SCFA concentrations were observed in GF and Abx-treated animals, compared to SPF mice. In FIG. 8A, fecal concentrations of acetate, propionate, and butyrate, were normalized by soluble chemical oxygen demand (sCOD). FIGS. 8B-8C show that within affected brain regions (i.e., CP and SN), microglia in SCFA-administered animals displayed morphology indicative of increased activation compared to untreated mice, and similar to cells from Ex-GF and SPF mice. Abx-treated animals, however, displayed microglia morphology similar to GF animals. FIG. 8B shows Caudoputamen (CP)-resident microglia parameters: number of branch points and total branch length. FIG. 8C shows that substantia nigra (SN)-resident microglia parameters: number of branch points and total branch length. FIGS. 8D and 8E show that changes in microglia diameter were also observed in the FC, but not the CB, demonstrating region-specific responses. FIG. 8D shows the diameters of microglia resident in the frontal cortex (FC). FIG. 8E shows the diameters of microglia resident in cerebellum (CB). FIGS. 8F-8O show that αSyn aggregated in mice administered SCFAs compared to untreated and Abx-treated mice, and similar to Ex-GF animals. FIGS. 8F-8I show representative images of the CP, SN, FC, and CB, respectively from Abx-ASO, ex-GF-ASO, or SCFA-ASO animals stained with aggregation-specific αSyn antibody, Phospho-Ser129-αSyn antibody, and Neurotrace/Nissl. FIG. 8J shows dot blot images of CP, inferior midbrain (Mid), FC, and CB homogenate from Abx-ASO, ex-GF-ASO, and SCFA-ASO animals immunostained with aggregation-specific αSyn antibody. FIGS. 8K-8N show densitometry quantification of dot blots from the (K) CP, (L) inferior midbrain, (M) FC, and (N) CB. FIG. 8O shows a western blot for αSyn from Triton soluble and insoluble fractions of CP homogenates derived from Abx- and SCFA-ASO animals.

FIGS. 9A-9H show that SCFAs promote αSyn-stimulated microglia activation and motor dysfunction. Animals were tested at 12-13 weeks of age. N=6-12, error bars represent the mean and standard error from 3 trials per animal, and compiled from 2 independent cohorts or 20-60 microglia per region analyzed. Data are plotted with controls from FIGS. 7A-7I for clarity. *$p≤0.05$; $p≤0.01$; *$p≤0.001$; ****$p≤0.0001$. Abbreviations: SPF, specific-pathogen-free; GF, germ-free; SCFA, short-chain fatty acid-treated; WT, wild-type; ASO, Thy1-α-synuclein genotype. See also FIGS. 8A-8O, 10A-10M, and 11A-11H. FIGS. 9A and 9B show that within affected brain regions (i.e., CP and SN), microglia in SCFA-administered animals displayed morphology indicative of increased activation compared to untreated mice, and similar to cells from Ex-GF and SPF mice. Abx-treated animals, however, displayed microglia morphology similar to GF animals. FIG. 9A shows representative 3D reconstructions of Iba1-stained microglia residing in the caudoputamen (CP) of wild-type or ASO SCFA-treated animals. FIG. 9B shows the diameters of microglia residing in the CP or substantia nigra (SN). FIGS. 9C-9F show that SCFA-ASO mice displayed significantly impaired performance in several motor tasks compared to untreated GF-ASO animals, including impairment in beam traversal, pole descent, and hindlimb reflex (compare GF-ASO to SCFA-ASO mice). FIG. 9C shows time to traverse beam apparatus. FIG. 9D shows time to descend pole. FIG. 9E shows time to remove nasal adhesive. FIG. 9F shows hindlimb clasping reflex score. FIGS. 9G and 9H show that GI deficits were also observed in the SCFA-treated transgenic animals. FIG. 9G shows time course of fecal output in a novel environment over 15 min. FIG. 9H shows total fecal pellets produced in 15 min.

FIGS. 10A-10G show that SCFAs either singly or in a mixture, over a range of concentrations, did not expedite the aggregation of human αSyn in vitro. FIGS. 10A-10C show that αSyn aggregation kinetics, as measured by ThT fluorescence in the presence of the indicated concentrations of (FIG. 10A) sodium acetate, (FIG. 10B) sodium propionate, or (FIG. 10C) sodium butyrate. FIGS. 10D and 10E show αSyn aggregation kinetics, as measured by ThT fluorescence in the presence of independent mixtures of SCFAs.

FIG. 10D: SCFA Mix 1—29.6 mM acetate, 11 mM propionate, and 18.5 mM butyrate; SCFA Mix 2×88.8 mM acetate, 33 mM propionate, and 55.5 mM butyrate; FIG. 10E: SCFA Mix 3×0.4 mM acetate, 0.15 mM propionate, and 0.24 mM butyrate; SCFA Mix 4—0.8 mM acetate, 0.3 mM propionate, and 0.47 mM butyrate; SCFA Mix 5×2.0 mM acetate, 0.74 mM propionate, and 1.18 mM butyrate. FIGS. 10F and 10G show time to half-max fluorescence intensity for individual SCFA treatments or SCFA mixtures respectively. N=3, bars represent the mean and standard error. FIGS. 10H and 10I show that SCFAs either singly or in a mixture, over a range of concentrations, did not alter the overall structure of αSyn amyloid fibrils. FIGS. 10H and 10I show representative atomic force microscopy of the final product from the above αSyn aggregation assays in the absence of SCFA or presence of SCFA Mix 1 respectively. FIGS. 10J-10M show that orral treatment of GF animals with heat-killed bacteria did not induce motor deficits, suggesting that bacteria need to be metabolically active. FIG. 10J shows time to cross beam. FIG. 10K shows time to descend pole. FIG. 10L shows time to remove nasal adhesive. FIG. 10M shows Hindlimb reflex scores.

FIGS. 11A-11H show minocycline reduces SCFA-induced αSyn motor deficits and pathology (related to FIGS. 9A-9H). Animals were tested at 12-13 weeks of age. N=6-12, error bars represent the mean and standard error from 3 trials per animal. Data were compiled from 2 independent cohorts. $0.05<p<0.1$; $*p\leq0.05$; $p\leq0.01$; $*p\leq0.001$; $**p\leq0.0001$. Abbreviations: SPF=specific pathogen free; GF=germ-free; WT=wild-type, ASO=Thy1-α-synuclein genotype. FIGS. 11A-11H show that oral treatment of SCFA-fed animals with the anti-inflammatory compound minocycline was sufficient to reduce TNF-a production, reduce αSyn aggregation, and improve motor function, without altering transgene expression. FIG. 11A shows ELISA analysis for TNFa present in the caudoputamen (CP) and inferior midbrain (Mid). FIG. 11B shows dot blot images of CP, inferior midbrain (Mid) homogenates for aggregate-specific αSyn. FIG. 11C shows densitometry quantification of dot blots from the CP and inferior midbrain (Mid). FIG. 11D shows qPCR analysis for human snca expression in total brain homogenate. FIG. 11E shows time to traverse beam apparatus. FIG. 11F shows time to descend pole. FIG. 11G shows time to remove nasal adhesive. FIG. 11H** shows Hindlimb clasping reflex score.

FIGS. 12A and 12B show that recipient animal groups were most similar to their respective human donor's profile in unweighted UniFrac based on PCoA. FIG. 12A shows unweighted UniFrac Principle Coordinate Analysis of microbial communities of human donors (large circles) and recipient mice (small circles). Each donor and recipient sample are matched by shading. FIG. 12B shows unweighted and weighted UniFrac analysis of microbial communities in recipient animals based on donor identity. FIGS. 12C and 12D show humanized mouse groups from PD donors were significantly more similar to each other than to communities transplanted from healthy do-nors, with this trend persisting when stratified by genetic background. There were significant differences between the healthy and PD donors in the ASO background compared to WT recipients, suggesting genotype effects on microbial community configuration. FIG. 12C shows unweighted and weighted UniFrac analysis of microbial communities in recipient animals based on mouse genotype. FIG. 12D shows comparison of unweighted and weighted UniFrac analysis of microbial communities in recipient animals. FIG. 12E** shows that a number of genera that were altered in animals colonized with microbiota derived from PD donors, compared to healthy controls, were identified. Taxa-level analysis of individual genera altered between PD and healthy donors as a function of recipient mouse genotype. Left column indicates percentage with significant differences observed; right column indicates fold change between PD and healthy donors. "*" indicates non-statistically significant differences.

FIG. 13A shows Bray-Curtis distance comparisons between humanized groups. FIGS. 13B and 13C show Bray-Curtis mean distance comparisons between identical versus different donors, or wild-type (WT) versus Thy1-α-synuclein (ASO) genotypes, respectively. FIG. 13D shows PICRUSt analysis for specific KEGGfamilies involved inSCFA production, light circles=healthy control derived microbes, dark circles=PD derived microbes. FIG. 13E shows fecal concentrations and relative abundances of acetate, propionate, and butyrate from humanized animals, normalized to soluble chemical oxygen demans. Compiled from 6 independent donor pairs, HC=healthy controls; PD=Parkinson's disease.

FIGS. 14A-14G show microbiota from PD patients induces increased αSyn-mediated motor deficits. Animals were tested at 12-13 weeks of age. n=3-6, error bars represent the mean and standard error from 3 trials per animal. $^{\#}0.05<p<0.1$; $*p\leq0.05$; $p\leq0.01$; $*p\leq0.001$; $**p\leq0.0001$. Abbreviations: HC, germ-free mice colonized with fecal microbes from healthy controls; PD, germ-free mice colonized with fecal microbes from Parkinson's disease patients; WT, wild-type; ASO, Thy1-α-synuclein genotype. See also FIGS. 15A-15G and Table 2. FIGS. 14A-14F show consistent among four of the six pairs (pairs #1, 3, 4, and 5), microbiota derived from individuals with PD promoted increased αSyn-mediated motor dysfunction. FIGS. 14A-14F show time to cross a beam, time to descend the pole, time to remove nasal adhesive, and hindlimb clasping reflex scores of mice humanized with microbiota from either PD patients or matched healthy controls. FIG. 14G** shows compilation of performance data from all groups revealed that microbiota from PD patients induced increased motor impairment in ASO animals compared to microbes from healthy controls in three of four tests used in this study. Compilation of all independent cohorts in each motor task: beam traversal, pole descent, adhesive removal, and hindlimb clasping reflex score, grouped by health status of fecal donor.

FIGS. 15A-15G show body weight and fecal output of humanized animals (related to FIGS. 14A-14G). Animals were tested at 12-13 weeks of age. N=3-6, error bars represent the mean and standard error from 3 trials per animal. $0.05<p<0.1$; $*p\leq0.05$; $**p\leq0.01$. Abbreviations: HC=germ-free mice colonized with fecal microbes from healthy controls, PD=germ-free mice colonized with fecal microbes from Parkinson's disease patients, WT=wild-type, ASO=Thy1-α-synuclein genotype. FIGS. 15A-15F show recipient animals displayed little alteration to weight and GI function as measured by fecal output. Body weight and fecal output following 15 min in novel environment for each PD and HC humanized pair. (FIG. 15A) Pair #1, (FIG. 15B) Pair #2, (FIG. 15C) Pair #3, (FIG. 15D) Pair #4, (FIG. 15E) Pair #5, (FIG. 15F) Pair #6. FIG. 15G shows Principle Component Analysis of compiled motor function between humanized animals. FIG. 15G depicts all motor function by PCoA displayed striking global differences between animals colonized with microbiota from PD donors, compared to those colonized with gut bacteria derived from healthy individuals.

DETAILED DESCRIPTION

Figure 1:
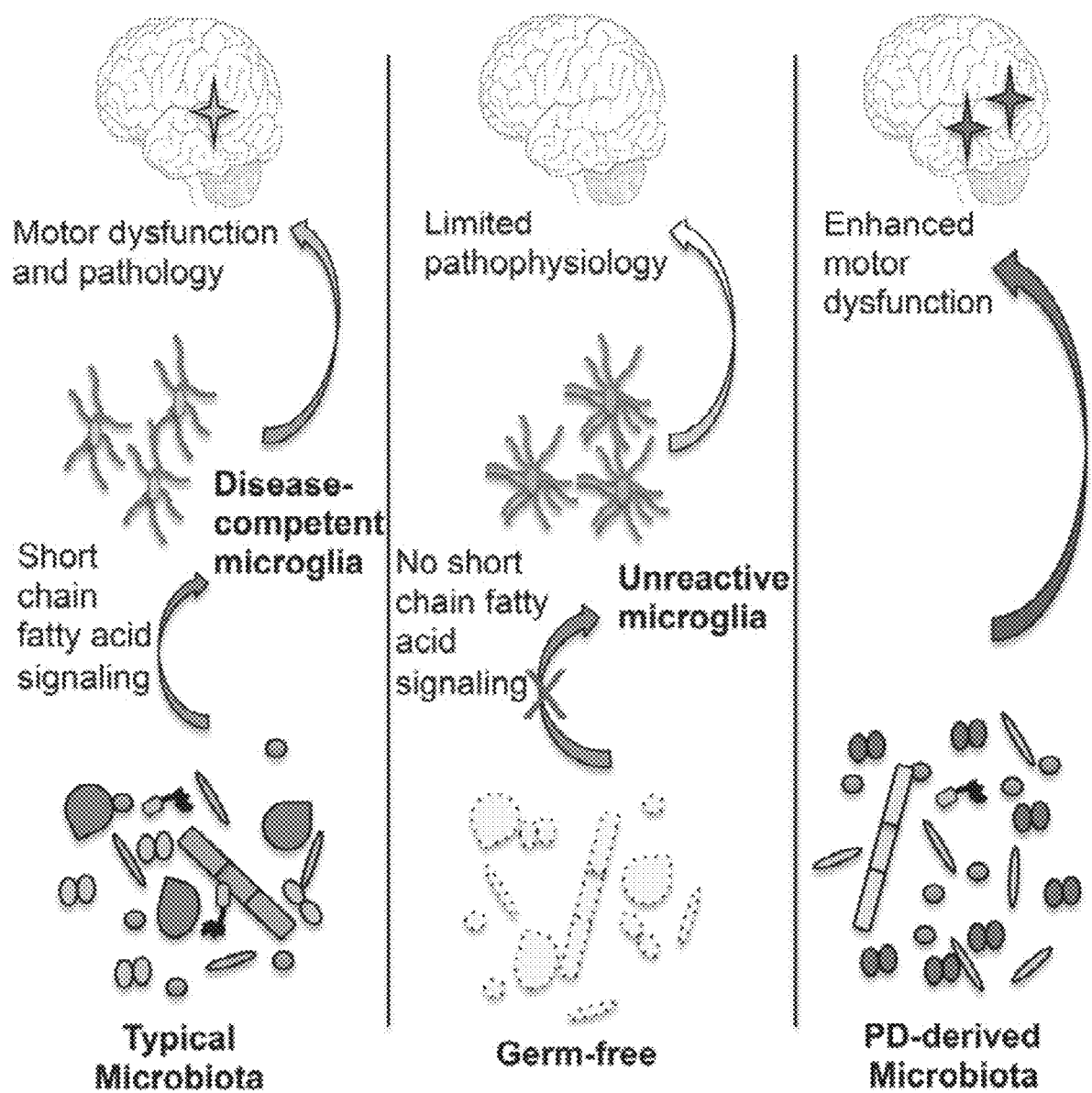
FIG. 1 is a schematic illustration showing that signals from gut microbes are required for the neuroinflammatory responses as well as hallmark gastrointestinal and α-synuclein-dependent motor deficits in a model of Parkinson's disease (PD). Gut microbes promote α-synuclein-mediated motor deficits and brain pathology, and depletion of gut bacteria reduces microglia activation. Short-chain fatty acid-treated animals (SCFAs) modulate microglia and enhance PD pathophysiology, and human gut microbiota from PD patients induce enhanced motor dysfunction in mice

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, NY 1989). For purposes of the present disclosure, the following terms are defined below.

As used herein, the term "subject" is an animal, such as a vertebrate, preferably a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is mouse or rat. In some embodiments, the subject is human.

As used herein, the term "treatment" refers to an intervention (e.g., a clinical intervention) made in response to a disease, disorder or physiological condition manifested by a patient, particularly a patient suffering from a neurodegenerative disease, for example Parkinson's diseases. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments the treatment may reduce, alleviate, or eradicate the symptom(s) of the disease(s). As used herein, the term "prevention" refers to any activity that reduces the burden of the individual later expressing those parkinsonian symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The pharmaceutically acceptable or appropriate carrier may include other compounds known to be beneficial to an impaired situation of the GI tract, (e.g., antioxidants, such as Vitamin C, Vitamin E, Selenium or Zinc); or a food composition. The food composition can be, but is not limited to, milk, yoghurt, curd, cheese, fermented milks, milk based fermented products, ice-creams, fermented cereal based products, milk based powders, infant formulae, tablets, liquid bacterial suspensions, dried oral supplement, or wet oral supplement.

A therapeutic agent or a protective agent may comprise a "drug." As used herein, a "drug" refers to a therapeutic agent or a diagnostic agent and includes any substance, other than food, used in the prevention, diagnosis, alleviation, treatment, or cure of a disease. Stedman's Medical Dictionary, 25th Edition (1990). The drug can include any substance disclosed in at least one of: The Merck Index, 12th Edition (1996); Pei-Show Juo, Concise Dictionary of Biomedicine and Molecular Biology, (1996); U.S. Pharmacopeia Dictionary, 2000 Edition; and Physician's Desk Reference, 2001 Edition. In some embodiments, the therapeutic agent is one of the embodiments of the compositions described herein. In some embodiments, the drug used in the therapeutic system is placed on, embedded, encapsulated or otherwise incorporated into a delivery matrix.

As used herein, the term "nutraceutical" refers to a food stuff (as a fortified food or a dietary supplement) that provides health benefits. Nutraceutical foods are not subject to the same testing and regulations as pharmaceutical drugs.

As used herein, the term "probiotic" refers to live microorganisms, which, when administered in adequate amounts, confer a health benefit on the host. The probiotics may be available in foods and dietary supplements (for example, but not limited to capsules, tablets, and powders). Non-limiting examples of foods containing probiotic include dairy products such as yogurt, fermented and unfermented milk, smoothies, butter, cream, hummus, kombucha, salad dressing, miso, tempeh, nutrition bars, and some juices and soy beverages.

As used herein, the term "metabolite" refers to any molecule involved in metabolism. Metabolites can be products, substrates, or intermediates in metabolic processes. For example, the metabolite can be a primary metabolite, a secondary metabolite, an organic metabolite, or an inorganic metabolite. Metabolites include, without limitation, fatty acids, amino acids, peptides, acylcarnitines, monosaccharides, oligosaccharides, lipids and phospholipids, prostaglandins, hydroxyeicosatetraenoic acids, hydroxyoctadecadienoic acids, steroids, bile acids, glycolipids, and phospholipids. In some embodiments, the metabolite is a microbial metabolite which is a metabolite produced by a microbe to, for example, regulate its own growth and development, to encourage beneficial interaction with other organisms, and to suppress organisms that are harmful to it. The microbial metabolites can be, for example, small molecular weight compounds (<2,500 Da). In some embodiments, the metabolite is an analogue of a microbial metabolite. In some embodiments, the microbial metabolites and analogues thereof include short-chain fatty acids (SCFAs), medium-chain fatty acids, and long-chain fatty acids; and salts and esters of the short-, medium- and long-fatty acids. Non-limiting examples of fatty acids include SCFAs acetate, propionate, and butyrate.

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or $F(ab')_2$, and Fv). For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, Conn., 1994, page 71 and Chapter 6.

Neurodegenerative Disorders

Neurological dysfunction is the basis of numerous human diseases. Behavioral, psychiatric, and neurodegenerative disorders often display hallmark neuropathologies within the central nervous system (CNS). One neuropathology, amyloidosis, results from aberrant aggregation of specific neuronal proteins that disrupt many cellular functions. Affected tissues often contain insoluble aggregates of proteins that display altered conformations, a feature believed to contribute to an estimated 50 distinct human diseases. Neurodegenerative amyloid disorders, including Alzheimer's, Huntington's, and Parkinson's diseases (PD), are associated with amyloid proteins. PD is the second most common neurodegenerative disease in the United States, affecting an estimated 1 million people and 1% of the US population over 60 years of age. Worldwide, about 3 million patients and caregivers suffer from the often-debilitating symptoms of PD, which involve motor deficits including tremors, muscle rigidity, bradykinesia, and impaired gait. It is a multifactorial disorder that has a strong environmental component, as less than 10% of cases are hereditary. Aggregation of α-synuclein (αSyn) is thought to be pathogenic in a family of diseases termed synucleinopathies, which includes PD, multiple system atrophy, and Lewy body disease. αSyn aggregation is a stepwise process, leading to oligomeric species and intransient fibrils that accumulate within neurons. Dopaminergic neurons of the substantia nigra pars compacta (SNpc) appear particularly vulnerable to effects of αSyn aggregates. Dopamine modulators are a first-line therapeutic in PD; however, treatments can carry serious side effects and often lose effectiveness. Discovery of safe and effective therapeutics are needed to address the increasing burden of PD in an ever-aging population.

Peripheral influences have been implicated in the onset and/or progression of diseases that impact the brain (Dinan and Cryan, 2015). Bidirectional communication between the gut and the brain in anxiety, depression, nociception, and autism spectrum disorder (ASD) has been suggested (Mayer et al., 2014; Schroeder and Backhed, 2016; Sharon et al., 2016). Gastrointestinal (GI) physiology and motility are influenced by signals arising both locally within the gut and from the CNS. Neurotransmitters, immune signaling, hormones, and neuropeptides produced within the gut may, in turn, impact the brain (Selkrig et al., 2014; Wall et al., 2014).

The human body is permanently colonized by microbes on virtually all environmentally exposed surfaces, the majority of which reside within the GI tract. The microbiota can have profound impact on neurodevelopment and the CNS. Germ-free (GF) mice and antibiotic-treated specific-pathogen-free (SPF) mice are altered in hippocampal neurogenesis, resulting in impaired spatial and object recognition. The microbiota regulates expression of the 5-hydroxytryptamine receptor (5-HT1A), brain-derived neurotropic factor (BDNF), and NMDA receptor subunit 2 (NR2A). GF mice have altered cortical myelination and impaired blood-brain barrier function. Additionally, the microbiota promotes enteric and circulating serotonin production in mice and affects anxiety, hyperactivity, and cognition. Fecal and mucosa-associated gut microbes are different between individuals with PD and healthy controls.

Gut bacteria can control the differentiation and function of immune cells in the intestine, periphery, and brain. Subjects with PD exhibit intestinal inflammation and GI abnormalities such as constipation often precede motor defects by many years. Braak's hypothesis posits that aberrant αSyn accumulation initiates in the gut and propagates via the vagus nerve to the brain in a prion-like fashion. This notion is supported by pathophysiologic evidence: αSyn inclusions appear early in the enteric nervous system (ENS) and the glossopharyngeal and vagal nerves, and vagotomized individuals are at reduced risk for PD. Further, injection of αSyn fibrils into the gut tissue of healthy rodents is sufficient to induce pathology within the vagus nerve and brainstem.

Treatment of Neurodegenerative Disorders

As disclosed herein, adjusting the composition of gut microbiota in a subject in need, for example by reducing/depleting PD-enhancing microbes in the gut microbiota of the subject, introducing a healthy microbiota, or both, can provide benefit(s) in the delay progression of PD in subjects.

Disclosed herein include methods for treating a neurodegenerative disorder, methods for delaying or reducing the likelihood of onset of a neurodegenerative disorder, methods for improving a motor deficit in a subject in need (e.g., a patient having a neurodegenerative disorder). The methods, in some embodiments, comprise adjusting the composition of gut microbiota in the subject. The methods, in some embodiments, further improve one or more physical impairments in the subject. The methods can, for example, improves one or more GI functions of the subject, relieves constipation of the subject. Non-limiting examples of the motor deficits include tremors, muscle rigidity, bradykinesia, impaired gait, and any combination thereof. In some embodiments, the neurodegenerative disease is a synucleinopathy which includes but not limited to a primary or idiopathic parkinsonism, secondary or acquired parkinsonism, hereditary parkinsonism, Parkinson plus syndromes or multiple system degeneration, and any combination thereof.

The methods, in some embodiments, comprise identifying a subject in need, wherein the subject in need is a subject has a abnormal level of aggregation of α-synuclein (αSyn), for example abnormally high level of αSyn aggregation. The methods, in some embodiments, comprise measuring the rate and/or level of αSyn aggregation in the subject (e.g., in the brain of the subject), measuring the clearance rate and/or level of insoluble αSyn protein aggregate in the subject (e.g., in the brain of the subject), or a combination thereof. Measuring the rate and/or level of αSyn aggregation in the subject (e.g., in the brain of the subject), measuring the clearance rate and/or level of insoluble αSyn protein aggregate in the subject (e.g., in the brain of the subject), or a combination thereof can be performed at various time point, for example before, during, and/or after adjusting the composition of gut microbiota of the subject.

Also provided herein are methods for reducing microglia activation in a subject in need, methods for reducing α-synuclein (αSyn) aggregates in a subject in need, and methods for reducing neuroinflammation in a subject in need. The subject in need, in some embodiments, suffers from a neurodegenerative disease, for example synucleinopathy (e.g., Parkinson's disease, dementia with Lewy body disease, multiple system atrophy, or any combination thereof). In some embodiments, the subject suffers from PD. The methods, in some embodiments, comprise adjusting the composition of gut microbiota in the subject. The methods can, for example, promote clearance (e.g., clearance rate, amount of clearance, or both) of insoluble αSyn protein aggregates, reduce aggregation (e.g., aggregation rate, amount of aggregation, or both) of αSyn protein, or both. The methods, in some embodiments, comprise measuring the rate and/or level of αSyn aggregation in the subject (e.g., in the brain of the subject), measuring the clearance rate and/or level of insoluble αSyn protein aggregate in the subject (e.g., in the brain of the subject), or a combination thereof. Measuring the rate and/or level of αSyn aggregation in the subject (e.g., in the brain of the subject), measuring the clearance rate and/or level of insoluble αSyn protein aggregate in the subject (e.g., in the brain of the subject), or a combination thereof can be performed at various time point, for example before, during, and/or after adjusting the composition of gut microbiota of the subject.

The subject in need can be a subject suffering from or at a risk of developing a neurodegenerative disorder, for example a neurodegenerative amyloid disorder, including but is not limited to, Alzheimer's disease, Huntinton's disease, Parkinson's disease, or any combination thereof. In some embodiments, the subject in need is a subject suffering from or at a risk of developing synucleinopathy, for example, Parkinson's disease, dementia with Lewy body disease, multiple system atrophy, or any combination thereof. In some embodiments, the subject in need is a subject suffering from or at a risk of developing Parkinson's disease. Non-limiting examples of neurodegenerative disorders include a primary or idiopathic parkinsonism, secondary or acquired parkinsonism, hereditary parkinsonism, Parkinson plus syndromes or multiple system degeneration, and any combination thereof.

As described herein, in some embodiments of the methods disclosed herein, after adjusting the composition of gut microbiota in the subject, the composition of the gut microbiota in the subject is restored to a normal level. As used herein in, a "normal level" of the composition of the gut microbiota refers to a level of the composition of the gut microbiota in non-PD subjects (e.g., healthy subjects). One of skill in the art will appreciate that variability in the composition of gut microbiota may exist between non-PD (e.g., healthy) individuals, and a normal level can be established as a representative of the composition of gut microbiota in a non-PD population, or a population of healthy subjects, for the comparison. Various criteria can be used to determine the inclusion and/or exclusion of a particular subject in the reference population, including but not limited to age of the subject (e.g. the reference subject can be within the same age group as the subject in need of treatment) and gender of the subject (e.g. the reference subject can be the same gender as the subject in need of treatment).

As described herein, adjusting the composition of the gut microbiota in the subject can be achieved by various methods, including but not limited to, fecal transplantation, microbiota conventionalization, microbial colonization, reconstitution of gut microbiota, probiotic treatment, antibiotic treatment, or a combination thereof.

In some embodiments, adjusting the composition of the gut microbiota in the subject comprises administering one or more antibiotics to the subject. At least one of the one or more antibiotics can be, for example, ampicillin, vancomycin, neomycin, gentamycin, erythromycin, or any combination thereof In some embodiments, the antibiotic treatment does not comprise administering rifampicin and/or minocycline to the subject. Adjusting the composition of the gut microbiota in the subject can also be achieved, for example, by administering to the subject an inhibitor of PD-enhancing microbial metabolite. Examples of inhibitors of PD-enhancing microbial metabolites include, but are not limited to, antibodies against one or more PD-enhancing microbial metabolites, antibodies against an intermediate for the in vivo synthesis of one or more PD-enhancing microbial metabolites, antibodies against a substrate for the in vivo synthesis of one or more PD-enhancing microbial metabolites, and inhibitors of one or more enzymes involved in the in vivo synthesis of one or more PD-enhancing microbial metabolites.

As used herein, the term "PD-enhancing microbial metabolites" refer to a microbial metabolite whose level is increased in subjects suffering from PD, or any pathological condition with one or more parkinsonian symptoms as compared to subjects do not suffer from PD or any pathological condition with one or more parkinsonian symptom (e.g., a healthy subjects). For example, the level of the microbial metabolite may be altered in circulation of the subject suffering from PD as compared to non-PD subjects. The level of the microbial metabolite can be altered in, for example, blood, feces, serum, plasma, body fluid (e.g., cerebrospinal fluid, pleural fluid, amniotic fluid, semen, or saliva), and/or urine of the PD subjects. Non-limiting examples of PD-enhancing microbial metabolites comprise one or more fatty acids, salt or ester thereof, or any combination thereof. The fatty acids can be, for example, short-chain fatty acids, medium-chain fatty acids, or long-chain fatty acids. In some embodiments, PD-enhancing microbial metabolites comprise one or more short-chain fatty acids (SCFAs), salt or ester thereof, or any combination thereof. In some embodiments, PD-enhancing microbial metabolites comprise SCFAs acetate, SCFAs propionate, SCFAs butyrate, or any combination thereof.

Adjusting the composition of the gut microbiota in the subject can comprises, for example, enhancing the level of one or more PD-protective bacterial species in the subject. In some embodiment, adjusting the composition of the gut microbiota in the subject comprises administering to the subject a composition comprising one or more PD-protective bacterial species. As used herein, the term "PD-protective bacterial species" refers to a bacterial species whose presence in the gut microbiota of a subject can protect the subject from developing PD or a pathological condition with one or more parkinsonian symptoms, slow down the disease progression in the subject suffering from PD or a pathological condition with one or more parkinsonian symptoms, ameliorate condition of PD or a pathological condition with one or more parkinsonian symptoms, relieving at least one symptoms of PD, or a combination thereof. In some embodiments, the PD-protective bacterial species only present in non-PD subjects (e.g., the gut of the subjects), but not in subjects suffering from PD or a pathological condition with one or more parkinsonian symptoms. In some embodiments, the PD-protective bacterial species present in a significantly lower level (e.g., no more than 50%, no more than 25%, no more than 10%, or no more than 5% or less) in subjects (e.g., gut of the subjects) suffering from PD or a pathological condition with one or more parkinsonian symptoms as compared to non-PD subjects (e.g., healthy subjects). Non-limiting examples of PD-protective bacterial species include species belong to Lachnospiraceae, Rikenellaceae, Peptostreptococcaceae, Clostridiaceae, *Enterococcus, Clostridium, Bacteroides*, or *Butyricicoccus* sp. family. In some embodiments, the composition is a probiotic composition, a nutraceutical composition, a pharmaceutical composition, or any combination thereof.

In some embodiments, adjusting the composition of the gut microbiota in the subject comprises reducing the level of one or more PD-enhancing bacterial species in the subject. As used herein, the term "PD-enhancing bacterial species" refers to a bacterial species whose presence (alone or in combination with one or more additional bacterial species) in the gut microbiota of a subject can increase the likelihood for the subject to develop PD or a pathological condition with one or more parkinsonian symptoms, expedite onset of PD or a pathological condition with one or more parkinsonian symptoms, increase severity of condition of PD or a pathological condition with one or more parkinsonian symptoms, worsen at least one symptoms of PD, or a combination thereof. In some embodiments, the PD-enhancing bacterial species only present in subjects (e.g., the gut of the subjects) with PD or a pathological condition with one or more parkinsonian symptoms, but not in non-PD subjects (e.g., healthy subjects). In some embodiments, the PD-enhancing bacterial species present in a significantly lower level (e.g., no more than 50%, no more than 25%, no more than 10%, or no more than 5% or less) in non-PD subjects (e.g., gut of the subjects) than in subjects suffering from PD or a pathological condition with one or more parkinsonian symptoms. In some embodiments, PD-enhancing bacterial species are bacterial species belonging to *Proteus* sp., *Bilophila* sp., *Roseburia* sp., *Pseudoramibacter Eubacterium*, or Veillonellaceae family. In some embodiments, the PD-enhancing bacterial species is a SCFA-producing bacterium, for example a SCFA-producing bacterium that belongs to KEGG family K00929, K01034 or K01035.

In some embodiments, adjusting the composition of the gut microbiota in the subject comprises introducing gut microbiota from a healthy subject to the subject being treated.

Some embodiments provide methods for treating a neurodegenerative disorder in a subject, comprising one or more of: administering an antibiotic to the subject; and administering to the subject an inhibitor of PD-enhancing microbial metabolite. Some embodiments provide methods for delaying or reducing the likelihood of onset of a neurodegenerative disorder in a subject, comprising one or more of administering an antibiotic to the subject; and administering to the subject an inhibitor of PD-enhancing microbial metabolite. Some embodiments provide methods of improving a parkinsonian symptom in a subject in need, comprising one or more of: administering an antibiotic to the subject; administering an anti-inflammatory agent to the subject; and administering to the subject an inhibitor of one or more PD-enhancing microbial metabolites. The antibiotic may not be rifampicin or minocycline. The neurodegenerative disorder can be, for example, a neurodegenerative amyloid disorder including, or not limited to, Alzheimer's disease, Huntington's disease, Parkinson's disease, or any combination thereof. In some embodiments, the neurodegenerative disorder is a synucleinopathy, for example Parkinson's disease, dementia with Lewy body disease, multiple system atrophy, or any combination thereof.

As described herein, the anti-inflammatory agent can be, in some embodiments, a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In some embodiments, the anti-inflammatory agent is a prohormone that modulates inflammatory processes, including but not limited to, prohormone convertase 1, proopiomelanocortin, prohormone B-type natriuretic peptide, SMR1 prohormone, and the like. In some embodiments, the anti-inflammatory agent is an enzyme having anti-inflammatory effects, including but not limited to, bromelain, papain, serrapeptidase, and proteolytic enzymes such as pancreatin (a mixture of tyrpsin, amylase and lipase). In some embodiments, the anti-inflammatory agent is a peptide with anti-inflammatory effects, including but not limited to, an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. In some embodiments, the anti-inflammatory peptide is cortistatin, a cyclic neuropeptide related to somatostatin, or peptides that correspond to an N-terminal fragment of SV-IV protein, a conserved region of E-, L-, and P-selectins, or the like. Other non-limiting examples of anti-inflammatory agent include collagen hydrolysates and milk micronutrient concentrates (e.g., MicroLactin.RTM. available from Stolle Milk Biologics, Inc., Cincinnati, Ohio), milk protein hydrolysates, casein hydrolysates, whey protein hydrolysates, and plant protein hydrolysates. In some embodiments, the anti-inflammatory agent is a plant extract having anti-inflammatory properties, including but not limited to extracts of blueberries, boswella, black catechu and Chinese skullcap, celery seed, chamomile, cherries, devils claw, eucalyptus, evening primrose, ginger, hawthorne berries, horsetail, Kalopanax pictus bark, licorice root, tumeric, white wallow, willow bark, and yucca.

In some embodiments, the anti-inflammatory agent and the antibiotic is not minocycline. Non-limiting examples of parkinsonian symptoms include an impaired motor function, enhanced αSyn aggregation, abnormal microglia activation, tremor, bradykinesia, muscle rigidity, impaired posture and balance, loss of automatic movements, speech impairment, writing impairment, and any combination thereof.

The inhibitor of PD-enhancing microbial metabolite can be, for example, an antibody against one or more PD-enhancing microbial metabolites, an antibody against an intermediate for the in vivo synthesis of one or more PD-enhancing microbial metabolites, an antibody against a substrate for the in vivo synthesis of one or more PD-enhancing microbial metabolites; or an inhibitor of an enzyme involved in the in vivo synthesis of one or more PD-enhancing microbial metabolites.

In the methods described herein, adjusting composition of gut microbiota in the subject, and/or administering to the subject an inhibitor of PD-enhancing microbial can be performed alone or in combination of one or more other therapies, for example antibiotic and anti-inflammatory therapies; or be performed alone to achieve therapeutic efficacy. For example, in some embodiments of the methods disclosed herein, the subject or the subject in need is not receiving an antibiotic and/or anti-inflammatory treatment. In some embodiments, the methods do not comprise administering the subject or the subject in need any antibiotics and/or anti-inflammatory agents. In some embodiments, the subject or the subject in need is not being treated with rifampicin and/or minocycline. In some embodiments, the subject or the subject in need did not receive any antibiotic treatment and/or treatment with anti-inflammatory agent at least 1 hour, at least 6 hours, at least 12 hours, at least 18 hours, at least 1 day, at least 2 days, at least 3 days, at least 5 days, at least 10 days, or at least 20 days before being adjusted of gut microbiota composition or other treatment (e.g., being administered with one or more inhibitors of PD-enhancing microbial metabolite). In some embodiments, the subject or the subject in need does not receive any antibiotic treatment and/or treatment with anti-inflammatory agent at least 1 hour, at least 6 hours, at least 12 hours, at least 18 hours, at least 1 day, at least 2 days, at least 3 days, at least 5 days, at least 10 days, or at least 20 days after being adjusted of gut microbiota composition or other treatment (e.g., being administered with one or more inhibitors of PD-enhancing microbial metabolite).

In some embodiments of the methods disclosed herein, the methods further comprise determining the presence and/or level of one or more PD-associated bacterial species in the subject to identify a subject in need of the treatment.

Diagnosis of PD

As disclosed herein, identification of specific PD-associated gut microbes in subjects can provide a diagnostic for PD before the onset of severe motor symptoms and/or as a marker for the severity of disease progress.

Methods of diagnosing parkinsonism in a subject are provided. In some embodiments, the methods comprise determining the presence and/or level of one or more PD-associated bacterial species in the subject, whereby the presence and/or abnormal level of the one or more PD-associated bacterial species indicates that the subject has a risk of developing, or is suffering from a symptom of parkinsonism. In some embodiments, the presence and/or level of one or more PD-associated bacterial species is determined in the gut of the subject.

As used herein, the term "PD-associated bacterial species" is a bacterial species whose level is altered in the gut microbiota of a subject suffering from PD or a pathological condition with one or more parkinsonian symptoms compared to non-PD subjects or subjects having no pathological condition with one or more parkinsonian symptoms (e.g., healthy subjects). In some embodiments, the level of the PD-associated bacterial species" is increased in the gut microbiota of a subject suffering from PD or a pathological condition with one or more parkinsonian symptoms compared to non-PD subjects or subjects having no pathological condition with one or more parkinsonian symptoms (e.g., healthy subjects). In some embodiments, the level of the PD-associated bacterial species" is decreased in the gut microbiota of a subject suffering from PD or a pathological condition with one or more parkinsonian symptoms compared to non-PD subjects or subjects having no pathological condition with one or more parkinsonian symptoms (e.g., healthy subjects). In some embodiments, the PD-associated bacterial species only present in subjects (e.g., the gut of the subjects) with PD or a pathological condition with one or more parkinsonian symptoms, but not in non-PD subjects (e.g., healthy subjects). In some embodiments, the PD-associated bacterial species present in a significantly lower level (e.g., no more than 50%, no more than 25%, or no more than 10%) in non-PD subjects (e.g., gut of the subjects) than in subjects suffering from PD or a pathological condition with one or more parkinsonian symptoms. In some embodiments, PD-associated bacterial species are bacterial species belonging to *Proteus* sp., *Bilophila* sp., *Roseburia* sp., *Pseudoramibacter Eubacterium*, or Veillonellaceae family. In some embodiments, the PD-associated bacterial species is a SCFA-producing bacterium, for example a SCFA-producing bacterium that belongs to KEGG family K00929, K01034 or K01035.

The presence and/or abnormal level of the one or more PD-associated bacterial species can indicate that the subject has a risk of developing parkinsonism or that the subject is suffering from parkinsonism. The parkinsonism can be, for example, a primary or idiopathic parkinsonism, secondary or acquired parkinsonism, hereditary parkinsonism, Parkinson plus syndromes or multiple system degeneration, or any combination thereof. In some embodiments, the parkinsonism is Parkinson's disease. In some embodiments, the subject is an adult.

Compositions

Disclosed herein include compositions comprising one or more PD-protective bacterial species. Non-limiting examples of PD-protective bacterial species include bacterial species that belongs to Lachnospiraceae, Rikenellaceae, Peptostreptococcaceae, Clostridiaceae, *Enterococcus, Clostridium, Bacteroides,* or *Butyricicoccus* sp. family. In some embodiments, the composition does not comprise PD-enhancing bacterial species. For example, the composition does not comprise, in some embodiments, bacterial species belong to at least one of *Proteus* sp., *Bilophila* sp., *Roseburia* sp., *Pseudoramibacter Eubacterium*, and Veillonellaceae family. In some embodiments, the composition does not comprises bacterial species belong to *Proteus* sp., *Bilophila* sp., *Roseburia* sp., *Pseudoramibacter Eubacterium*, and Veillonellaceae family.

The type of the composition can vary, for example it can be a probiotic composition, a nutraceutical composition, a pharmaceutical composition, or any combination thereof. In some embodiments, the composition is a food, a drink or a food supplement. In some embodiments, the composition is a pharmaceutical composition comprising one or more pharmaceutically acceptable carriers. In some embodiments, the pharmaceutical composition comprises an acid suppressant, an antacid, an $H_2$ antagonist, a proton pump inhibitor, or a combination thereof. The composition can be in various forms, for example, the composition can be in a lyophilised, pulverized, or powdered formulation; in a suspension (for example, a suspension in which the bacteria are suspended); a liquid culture, or is lyophilised, pulverized, or powdered; or as a pharmaceutical composition dissolved in, for example, saline.

The composition can be in the form of capsules, tablets, slush, or powders, or a combination thereof. The composition can comprise, for example, dairy products such as yogurt, fermented and unfermented milk, smoothies, butter, cream, hummus, kombucha, salad dressing, miso, tempeh, nutrition bars, and some juices and soy beverages. In some embodiments, the composition is formulated as an enteric coated capsule, an enteric coated micro capsule, a powder suitable for reconstitution, a nasoduodenal infusion, or for delivery in the form of an enema or a colonoscopic infusion; or as a pharmaceutical composition added to: a food, a food additive, a dairy-based product, a soy-based product or a derivative thereof, a jelly, or a yogurt.

Also disclosed herein include pharmaceutical compositions comprising an inhibitor of a PD-enhancing microbial metabolite. The PD-enhancing microbial metabolite can be, for example, a fatty acid, or a salt or ester thereof. In some embodiments, the PD-enhancing microbial metabolite is a short-chain fatty acid (SCFA), a medium-chain fatty acid, a long-chain fatty acid, a salt or ester of a short-chain fatty acid, a salt or ester of a medium-chain fatty acid, or a salt or ester of a long-chain fatty acid. The inhibitor can be, for example, an antibody against the PD-enhancing microbial metabolite, an antibody against an intermediate for the in vivo synthesis of the PD-enhancing microbial metabolite, an antibody against a substrate for the in vivo synthesis of the PD-enhancing microbial metabolite, or an inhibitor of an enzyme involved in the in vivo synthesis of the PD-enhancing microbial metabolite. The pharmaceutical composition can comprise, for examples, one or more pharmaceutically acceptable excipients. The pharmaceutical composition can be used for the treatment of various disorders/diseases, including but not limited to, neurodegenerative disorder (such as Parkinson's disease).

Also provided are pharmaceutically acceptable prodrugs of the pharmaceutical compositions, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the agent). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in Bundgaard, Design of Prodrugs (Elsevier Press, 1985).

Also provided are pharmaceutically active metabolites of the pharmaceutical compositions, and uses of such metabolites in the methods of the invention. A "pharmaceutically active metabolite" means a pharmacologically active product of metabolism in the body of a compound or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any suitable formulation of the compounds described herein can be prepared. See, generally, Remington's Pharmaceutical Sciences, (2000) Hoover, J. E. editor, 20th edition, Lippincott Williams and Wilkins Publishing Company, Easton, Pa., pages 780-857. A formulation is selected to be suitable for an appropriate route of administration. Some routes of administration are oral, parenteral, by inhalation, topical, rectal, nasal, buccal, vaginal, via an implanted reservoir, or other drug administration methods. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. One of skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The pharmaceutical compositions as described herein can be soluble in organic solvents such as chloroform, dichloromethane, ethyl acetate, ethanol, methanol, isopropanol, acetonitrile, glycerol, N,N-dimethylformamide, N,N-dimethylacetamide, dimethylsulfoxide, or any combination thereof. In some embodiments, formulations are prepared by mixing an agent with a pharmaceutically acceptable carrier. In some embodiments, the formulation can be prepared using a method comprising: a) dissolving a described agent in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. The carbohydrate can comprise, for example, dextrose. The pharmaceutical compositions obtained using the present methods are stable and useful for animal and clinical applications.

Non-limiting examples of water-soluble organic solvents for use in the present methods include, but are not limited to, polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Non-limiting examples of water soluble non-ionic surfactants for use in the present methods include, but are not limited to, CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Non-limiting examples of water-soluble lipids for use in the present methods include, but are not limited to, vegetable oils, triglycerides, plant oils, or a combination thereof. Examples of lipid oils include, but are not limited to, castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Non-limiting examples of fatty acids and fatty acid esters for use in the present methods include, but are not limited to, oleic acid, monoglycerides, diglycerides, a mono- or di-fatty acid ester of PEG, or a combination thereof.

Non-limiting examples of cyclodextrins for use in the present methods include, but are not limited to, alpha-cyclodextrin, beta-cyclodextrin, hydroxypropyl-beta-cyclodextrin, or sulfobutyl ether-beta-cyclodextrin.

Non-limiting examples of phospholipids for use in the present methods include, but are not limited to, soy phosphatidylcholine, or distearoyl phosphatidylglycerol, and hydrogenated forms thereof, or a combination thereof.

One of skill in the art may modify the formulations within the teachings of the specification to provide numerous formulations for a particular route of administration. For example, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

The pharmaceutical compositions disclosed herein may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution, and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-8 described below.

TABLE 1

Reagents and Resources.

| REAGENT or RESOURCE | SOURCE | IDENTIFIER |
|---|---|---|
| Antibodies | | |
| Anti-aggregated/fibril alpha-synuclein; MJFR-14-6-4-2 | Abcam | Cat# ab209538 |
| Anti-phospho Ser129 alpha-synuclein | BioLegend | Cat# 825701, RRID: AB 2564891 |
| Anti-Iba1 | Wako | Cat# 019-19741, RRID: AB 839504 |
| Anti-mouse IgG-Alexafluor 488 | Life Technologies | Cat# A-11001, RRID: AB 2534069 |
| Anti-rabbit IgG-Alexafluor 546 | Life Technologies | Cat# A-11010, RRID: AB 2534077 |
| Neurotrace 435/455 Blue | Life Technologies | Cat# N-21479 |
| Anti-alpha-synuclein | BD | Cat# 610787, RRID: AB 398108 |
| Anti-mouse IgG-HRP | Cell Signaling Technology | Cat# 7076S |
| Anti-rabbit IgG-HRP | Cell Signaling Technology | Cat# 7074S |
| Chemicals, Peptides, and Recombinant Proteins | | |
| Minocycline | Arcos/Fisher Scientific | Cat# AC455330010 |
| Ampicillin | Sigma Aldrich | Cat# A0166 |
| Vancomycin | Sagent Pharmaceuticals | Cat# 157-99 |
| Neomycin | Fisher Scientific | Cat# BP26695 |
| Gentamicin | Sigma Aldrich | Cat# G1264 |
| Erythromycin | Sigma Aldrich | Cat# E5389 |
| Sodium acetate | Sigma Aldrich | Cat# S5636 |
| Sodium propionate | Sigma Aldrich | Cat# P5436 |
| Sodium butyrate | Sigma Aldrich | Cat# 19364 |
| Purified alpha synuclein | Abcam | Cat# ab51188 |
| Thioflavin T | Sigma Aldrich | Cat# T3516 |
| Critical Commercial Assays | | |
| Alpha-synuclein ELISA | ThermoFisher | Cat# KHB0061 |
| iScript cDNA Synthesis kit | Biorad | Cat# 170-8890 |
| SyberGreen qPCR Master Mix | Applied Biosystems | Cat# 4309155 |
| IL-6 ELISA | eBioscience | Cat# 88-7324 |
| TNF ELISA | eBioscience | Cat# 88-7064 |
| MoBio Power Soil Kit | MoBio Laboratories | Cat# 12888-50 |
| Deposited Data | | |
| 16 s RNA sequences | QIITA; https://qiita.ucsd.edu/ | 10483 |
| 16 s RNA sequences | EMBL, ENA; http://www.ebi.ac.uk/ena | ERP019564 |
| Experimental Models: Organisms/Strains | | |
| Mouse: Thy 1-alpha synuclein | Marie Francoise-Chesselet, University of California, Los Angeles | N/A |
| Mouse: BDF1 | Generated from B6 x DBA | N/A |
| Mouse: C57BL/6 | Charles River | Strain: 027 |
| Mouse: DBA/2 | Charles River | Strain: 026 |
| Bacteria: Escherichia coli K12 MC4100 | Matt Chapman, University of Michigan | N/A |
| Sequence-Based Reagents | | |
| Primers: hu-snca-<br>Fwd: 5'-TTGCAGCAGCCACTGGCTTTG-3' (SEQ ID NO: 1)<br>and Rev: 5'-GGATCCACAGGCATATCTTCCAGAA-3' (SEQ ID NO: 2) | PrimerBank | N/A |
| Primers: tnfa-<br>Fwd: 5'-CCCTCACACTCAGATCATCTTCT-3' (SEQ ID NO: 3)<br>and Rev: 5'-GCTACGACGTGGGCTACAG-3' (SEQ ID NO: 4) | PrimerBank | N/A |
| Primers: il6-<br>Fwd: 5'-TAGTCCTTCCTACCCCAATTTCC-3' (SEQ ID NO: 5)<br>and Rev: 5'-TTGGTCCTTAGCCACTCCTTC-3' (SEQ ID NO: 6) | PrimerBank | N/A |

TABLE 1-continued

Reagents and Resources.

| REAGENT or RESOURCE | SOURCE | IDENTIFIER |
|---|---|---|
| Primers: ddit4-<br>Fwd: 5'-CAAGGCAAGAGCTGCCATAG-3' (SEQ ID NO: 7)<br>and Rev: 5'-CCGGTACTTAGCGTCAGGG-3' (SEQ ID NO: 8) | PrimerBank | N/A |
| Primers: bdnf-<br>Fwd: 5'-TCATACTTCGGTTGCATGAAGG-3' (SEQ ID NO: 9)<br>and Rev: 5'-AGACCTCTCGAACCTGCCC-3' (SEQ ID NO: 10) | PrimerBank | N/A |
| Primers: gapdh-<br>Fwd: 5'-CATGGCCTTCCGTGTTCCTA-3' (SEQ ID NO: 11)<br>and Rev: 5'-CCTGCTTCACCACCTTCTTGAT-3' (SEQ ID NO: 12) | PrimerBank | N/A |

Software and Algorithms

| | | |
|---|---|---|
| ImageJ | National Institutes of Health | https://imagej.nih.gov/ij/ |
| Imaris | Bitplane | http://www.bitplane.com/imaris/imaris |
| SortMeRNA 2.0 | Kopylova et al. (2012) | http://bioinfo.lifl.fr/RNA/sortmerna/ |
| Greengenes | Lawrence Berkeley National Labs | http://greengenes.lbl.gov/cgi-bin/nph-index.cgi |
| QIIME 1.9 | Rob Knight laboratory, UCSD and Greg Caporaso laboratory, Northern Arizona University | http://qiime.org/ |
| Seaborn 0.70 | Michael Waskom, Stanford University | http://seaborn.pydata.org/ |

Mice

Female BDF1 background, Thy1-αSyn animals heterozygous for the Thy1-α-synuclein transgene on the X chromosome were bred with wild-type male BDF1 mice to generate the male ASO and WT littermates used in the study. Male BDF1 were bred by crossing female C57BL/6 with DBA/2 males (Charles River, Hollister, CA). Breeding pairs were replenished every 6 months with transgenic females and newly generated BDF1 males. Germ-free (GF) Thy1-αSyn breeding pairs were generated via caesarian section and males newly generated every 6 months. Following surgical removal of the uterus and delivery of pups, microbiologically-sterile animals were fostered by GF Swiss-Webster dams. SPF, antibiotic-treated, and ex-GF animals were housed in autoclaved, ventilated, microisolator caging. GF and SCFA-treated animals were housed in open-top caging within flexible film isolators and maintained microbiologically sterile. Microbial sterility was confirmed on a bi-weekly basis.

16s rRNA PCR from fecal-derived DNA and plating of fecal pellets on Brucella blood agar media under anaerobic conditions and tryptic soy blood agar under aerobic conditions. All animals, irrespective of colonization status, received autoclaved food (LabDiet Laboratory Autoclavable Diet 5010, St Louis, MO) and water ad libitum, were maintained on the same 12 hour light-dark cycle, and housed in the same facility. Antibiotic-treated animals were provided ampicillin (1 g/L; Sigma Aldrich, St. Louis, MO), vancomycin (0.5 g/L; Sagent Pharmaceuticals, Schaumburg, IL), neomycin (0.5 g/L; Fisher Scientific), gentamycin (100 mg/L; Sigma Aldrich), and erythromycin (10 mg/L; Sigma Aldrich) in drinking water beginning at 5-6 weeks of age through 12-13 weeks of age. Ex-GF animals were generated by colonizing 5-6 week old GF animals with cecal contents from 3 wild-type BDF1 males resuspended in sodium bicarbonate buffer prior to oral gavage. SCFA treated animals were provided with drinking containing sodium acetate (67.5 mM; Sigma Aldrich), sodium propionate (25 mM; Sigma Aldrich), and sodium butyrate (40 mM; Sigma Aldrich) beginning at 5-6 weeks of age until 12-13 weeks of age. Minocycline (Arcos Organics) treatment was provided in drinking water ad libitum at 2 g/L, concurrently with SCFAs from 5-6 weeks of age until 12-13 weeks. GF animals treated with heat-killed bacteria were provided ~$5 \times 10^8$ cfu/mL of lysogeny broth (LB) grown *Escherichia coli* MC4100 (from Matthew Chapman, U. of Michigan), washed twice in phosphate buffered saline and boiled for 45 minutes, in drinking water ad libitum.

Human Donor and Criteria

Human donors were selected from patients seen at the Movement Disorder Clinic at Rush University. PD was diagnosed according to the UK Brain Bank Criteria. Exclusion criteria for PD subjects: atypical or secondary Parkinsonism; the use of probiotics or antibiotics within three months prior to sample collection; use of NSAIDs; primary gastrointestinal pathology; history of chronic GI illness (including IBD and celiac disease); unstable medical, neurological, or psychiatric illness; low platelet count (<80 k); uncorrectable prolonged PT 9>15 sec); or history of bleeding that precludes biopsies. All patients had normal mucosa in their rectum and sigmoid by sigmoidoscopy and by H&E histology. Healthy controls were matched as closely as possible to PD patients. Inclusion criteria for healthy subjects: normal physical exam and blood work; no digestive complaints, symptoms, or history of disease; no neurodegenerative disease; no probiotic, antibiotic, NSAIDs, or prescription medication use at least three months prior to sample collection.

Motor Function and Gastrointestinal Testing

Excluding humanized animals, all motor function assessment was performed in the identical, genotobiotic animal facility. Humanized animals were tested within a laminar-flow biosafety cabinet in the same facility. Motor function for all animals was tested between hours 7 and 9 of the light-phase. All tests were performed similarly to studies described in Fleming et al., 2004, Early and progressive sensorimotor anomalies in mice overexpressing wild-type human alpha-synuclein. *J. Neurosci.* 24, 9434-9440, the content of which is incorporated herein in its entirety). Beam traversal was performed first, before allowing animals to rest for ~1 hr and testing on pole descent. The following day, adhesive removal and hindlimb scoring was performed. Fecal output was performed within 3 days and immediately prior to tissue collection.

Beam Traversal

A 1 m plexiglass beam (Stark's Plastics, Forest Park, OH) was constructed of four segments of 0.25 m in length. Each segment was of thinner widths 3.5 cm, 2.5 cm, 1.5 cm, and 0.5 cm, with 1 cm overhangs placed 1 cm below the surface of the beam. The widest segment acted as a loading platform for the animals and the narrowest end placed into home cage. Animals had two days of training to traverse the length of the beam before testing. On the first day of training, animals received 1 trial with the home cage positioned close to the loading platform and guided the animals forward along the narrowing beam. Animals received two more trials with limited or no assistance to encourage forward movement and stability on the beam. On the second day of training, animals had three trials to traverse the beam and generally did not require assistance in forward movement. On the third day, animals were timed over three trials to traverse from the loading platform and to the home cage. Timing began when the animals placed their forelimbs onto the 2.5 cm segment and ended when one forelimb reached the home cage.

Pole Descent

A 0.5 m long pole, 1 cm in diameter, wrapped with non-adhesive shelf liner to facilitate the animals grip, was placed into the home cage. Animals received two days of training to descend from the top of the pole and into the home cage. On day one of training, animals received 3 trials. The first trial, animals were placed head-down ⅓ the distance above the floor, the second trial from ⅔ the distance, and the third trial animals were placed at the top. On the second day of training, animals were given 3 trials to descend, head-down, from the top of the pole. On the test day, animals were placed head-down on the top of the pole and timed to descend back into the home cage. Timing began when the experimenter released the animal and ended when one hindlimb reached the home cage base.

Adhesive Removal

¼" round adhesive labels (Avery, Glendale, CA) were placed on the nasal bridge between the nostrils and forehead. Animals were placed into their home cage (with cage mates removed) and timed to completely remove the sticker. Animals were recorded over three trials.

Hindlimb Clasping Reflex Scoring

Animals were gently lifted upward by the mid-section of the tail and observed over ~5-10 s similar to what was described in Zhang et al., 2014, Motor impairments, striatal degeneration, and altered dopamine-glutamate interplay in mice lacking PSD-95. J. Neurogenet. 28, 98-111 (the content of Zhang et al. is incorporated herein in its entirety). Animals were assigned a score of 0, 1, 2, 3 based on the extent to which the hindlimbs clasped inward. 0, indicating no clasping, was given to animals that freely moved both their limbs and extended them outward. A score of 1 was assigned to animals which clasped one hindlimb inward for the duration of the restraint or if both legs exhibited partial inward clasping. A score of 2 was given if both legs clasped inward for the majority of the observation, but still exhibited some flexibility. A score of 3 was assigned if animals displayed complete paralysis of hindlimbs that immediately clasped inward and exhibited no signs of flexibility.

Inverted Grid

Animals were placed in the center of a 30 cm by 30 cm screen with 1 cm wide mesh. The screen was inverted head-over-tail and placed on supports ~40 cm above an open cage with deep bedding. Animals were timed until they released their grip or remained for 60 s.

Fecal Output

Animals were removed from their home cages and placed into a 12 cm×25 cm translucent cylinder. Fecal pellets were counted every 5 min, cumulative over 15 min. Principal component analysis of all motor function was performed using MATLAB software (MathWorks) using behavioral data collected from subjects that performed at least 3 tasks. Data was centered and standardized (s=1) prior to running the pca function. Only PC1 and PC2, which accounted for 70.5% of the variance, were plotted using the corresponding factor loadings for each individual subject.

Immunostaining and Microglia Reconstructions

Animals were sedated with pentobarbital and well-perfused with phosphate-buffered saline, brains were dissected and hemispheres fixed in 4% (w/v) paraformaldehyde. 50 mm sagittal sections were generated via vibratome. Free-floating sections were stained with anti-aggregated/fibril αSyn MJFR1 (1:1000; rabbit; AbCam, Cambridge UK), anti-phosphoSer129 αSyn (1:1000; mouse; Biolegend, San Diego, CA), and Neurotrace (Life Technologies, Carlsbad, CA), or with anti-Iba1 (1:1000; rabbit; Wako, Richmond, VA) and subsequently stained with anti-mouse IgG-AF488 and anti-rabbit IgG-AF546 (1:1000; Life Technologies). Sections were mounted with ProFade Diamond (Life Technologies), and imaged with a 10× objective on a Zeiss LSM800 confocal microscope. 2-3 fields per region per animal were imaged and compiled in ImageJ software for analysis. For microglia reconstructions, z stacks were imaged at 1 mm steps and subsequently analyzed using Imaris software, as described in Erny et al., 2015, Host microbiota constantly control maturation and function of microglia in the CNS. Nat. Neurosci. 18, 965-977 (the content of Erny et al. is incorporated herein in its entirety).

Semi-automated reconstruction of microglia cell bodies and processes were performed, whereby the experimenter designates individual cell bodies and the software quantifies diameter, dendrite length, and branch points from each given cell body. 20-60 cells per region per animal were analyzed.

CD11b Enrichment and qPCR Analysis

Perfused whole brains were homogenized in PBS via passage through a 100 mm mesh filter, myelin debris were removed using magnetic separation with Myelin Removal Beads (Miltenyi Biotec, San Diego CA), according to manufacturer's instructions. CD11b enrichment was performed similarly, with magnetic enrichment by Microglia Microbeads (Miltenyi Biotec, San Diego, CA), according to manufacturer's instructions. Generally, greater than 90% of cells enriched stained positive for CD11b by immunofluorescence microscopy. For RNA analysis, dissected tissue (frontal cortex, caudoputamen, inferior midbrain, and cerebellum) or CD11b-enriched cell pellets, were lysed in Trizol for Direct-Zol RNA extraction (Zymo Research, Irvine, CA). cDNA was generated via iScript cDNASynthesis kit (BioRad, Hercules, CA). qRT-PCR was performed with SybrGreen master mix (Applied Biosystems, Foster City, CA) on an AB 7900ht instrument using primers derived from PrimerBank for the indicated target genes and quantified as DDCT, relative to gapdh (Primers listed in Table 1 above).

Cytokine and αSyn ELISAs and Western Blots

Tissue homogenates were prepared in RIPA buffer containing protease inhibitor cocktail (ThermoFisher, Pittsburgh, PA) and diluted into PBS. TNF-a and IL-6 ELISAs (eBioscience, San Diego, CA) and αSyn ELISAs (ThermoFisher) were performed according to manufacturer's instructions. For dot blot quantification of αSyn fibrils, 1 mg of tissue homogenate from the specified region was spotted in 1 mL volume aloquats onto 0.45 mm nitrocellulose membranes. For Triton X-soluble versus insoluble fraction western blots, brain hemispheres were homogenized in RIPA buffer containing 1% Triton X-100, centrifuged at 15 k×g for 60 min at 4o C to precipitate insoluble proteins from the Triton soluble supernatant. The insoluble fraction was solubilized in 10% sodium dodecyl sulfate, as previously described in Klucken et al. (2006, Clinical and biochemical correlates of insoluble alpha-synuclein in dementia with Lewy bodies. Acta Neuropathol. 111, 101-108, the content of which is incorporated herein in its entirety). 5 mg of each fraction was separated by 4%-20% SDS-PAGE (ThermoFisher), blotted onto PVDF membranes. All membranes were blocked with 5% dry skim milk in Tris-buffered saline with 0.1% Tween-20. Anti-aggregated αSyn antibody (1:2000; rabbit; Abcam) or anti-αSyn (1:1000; mouse; BD) was diluted in skim milk and incubated overnight at 4o C. Membranes were probed with anti-rabbit or anti-mouse IgG HRP (1:1000; Cell Signaling Technology). All blots were detected with the Clarity chemiluminescence substrate (BioRad) on a BioRad GelDoc XR. Densitometry was performed using ImageJ software.

αSyn Aggregation Assays

For in vitro aggregation kinetics, 70 mM αSyn was purified as described in Chorell et al., 2015, Bacterial chaperones CsgE and CsgC differentially modulate human a-synuclein amyloid formation via transient contacts. PLoS ONE 10, e0140194 (the content of Chorell et al. is incorporated herein in its entirety), and incubated in phosphate-buffered saline solution (0.01 M phosphate buffer, 0.0027 M potassium chloride, 0.137M sodium chloride, pH 7.4) in the presence of 12 mM of Thioflavin T (ThT; Sigma Aldrich) and increasing concentrations of SCFA. A nonbinding 96-well plate with half area (Corning #3881) was used for each experiment and a 2 mm diameter glass bead was added to each well to accelerate the aggregation. The ThT fluorescence signal was recorded using a microplate reader (Fluostar OPTIMA Microplate reader, BMG Labtech) with the excitation filter of 440±10 nm and an emission filter of 490±10 nm under intermittent shaking conditions at 37o C. The kinetic curves were normalized to the fluorescence maxima and the time to reach half-maximum intensity quantified. For atomic force microscopy (AFM) imaging, samples were diluted with ultrapure water to ~3 mM total protein concentration, and 50 mls were pipetted onto freshly cleaved mica and left to dry. The samples were imaged with a Modular scanning probe microscope NTEGRA Prima (NT-MDT) in intermittent contact mode in air using a gold-coated single crystal silicon cantilever (spring constant of ~5.1 N/m) with a resonance frequency of ~150 kHz. AFM images were processed with Gwyddion open source software.

SCFA Extraction and Analysis

Fecal samples were collected from animals at 12 weeks of age. Each fecal pellet was mixed with 1 mL sterile 18 U de-ionized water. The pellet-water mixtures were homogenized by mixing at 3200 rpm for five minutes and centrifuged for 15 min at 13,000 rpm at 4o C. Supernatants were filtered using Acrodisc LC 13 mm sterile syringe filters with 0.2 mm PVDF membranes (Pall Life Sciences). The filtrates were used for high performance liquid chromatography (HPLC) analysis. Short chain fatty acids (SCFAs) were analyzed using HPLC (LC-20AT, Shimadzu) equipped with a carbohydrate column (Aminex HPX-87H column, Biorad) and photodiode array detector (PDA, Shimadzu). The eluent was 5 mM $H_2SO_4$, fed at a flowrate of 0.6 mL/min, and the column temperature was 50o C. The run time was 60 min. Standard curves were generated by diluting 10 mM volatile fatty acid standard solution (acetic acid, butyric acid, formic acid, valeric acid, isovaleric acid, caproic acid, isocaproic acid, and heptanoic acid) to 50 nM to 5000 nM. Concentrations of SCFAs were normalized to soluble chemical oxygen demand. sCOD values of the fecal supernatants were measured with high range (20-1500 mg/L) Hach COD digestion tubes (Hach Company, Loveland) as recommended by the manufacturer. The wavelength used to measure COD with Hach spectrophotometer was 620 nm.

Microbiome Profiling

Fecal pellets were collected at day 7, 14, 21, and 49 post fecal transplant, from animals housed in groups of 1-3 by genotype and donor. Samples were sequenced according to the Earth Microbiome Project protocols as described in Gilbert et al., 2014, The Earth Microbiome project: successes and aspirations. BMC Biol. 12, 69 (the content of Gilbert et al. is incorporated herein in its entirety). Briefly, DNA was extracted using a MoBio Power soil kit (Carlsbad, CA), and the V4 region of the 16S rRNA gene was amplified using barcoded primers described in Walters et al., 2015. Sequencing was performed using an Illumina MiSeq. Operational Taxonomic Units (OTUs) were picked closed reference using SortMeRNA 2.0 (described in Kopylova et al., 2012) against the August 2013 release of Greengenes (described in McDonald et al., 2012) in QIIME 1.9 (described in Caporaso et al., 2010). The table was rarefied to 7500 sequences per sample for alpha and beta diversity calculations. Differential abundance was performed on a table filtered to exclude samples with less than 7500 sequences. Weighted and unweighted UniFrac (described in Lozupone and Knight, 2005) distances were calculated in QIIME 1.9. Principle Coordinate Analysis (PCoA) projections were visualized using Emperor 0.9.4 (described in Vazquez-Baeza et al., 2013). Function was inferred using PICRUSt 1.0 (described in Langille et al., 2013); predicted functional repertoires were compared using Bray Curtis distance. Significance tests were performed using permanova in scikit-bio 0.4.2 and permutative t tests in QIIME 1.9, both with 999 permutations per test. Differential abundance calculations were performed using genus-level taxa and KEGG-based relative abundance of all counts offset by one. Tests were performed using ANCOM (described in Mandal et al., 2015) in scikit-bio 0.4.2 with a one-way ANOVA test with a Bonferroni-corrected alpha of 0.1 as the rejection threshold. Mice colonized with samples from healthy donors or donors with PD were compared in the BDF1 or Thy1-αSyn genetic backgrounds. Significantly different taxa were compared between the groups, and classified as significant in both, significant in the Thy1-αSyn background only, or significant in the BDF1 background. Plots were generated using Seaborn 0.7.0.

Quantification and Statistical Analysis

Microbiome population statistics are described in detail above. Excluding these, datasets were analyzed within GraphPad Prism 6 software. Pairwise comparisons were generated with two-tailed t tests. Comparisons of groups were generated with one-way ANOVA. P values, n values, definition of center and dispersion measurements are indicated in the associated Figure legends for each Figure.

Data and Software Availability 16s sequencing data and metadata are available online through the QIITA website (https://qiita.ucsd.edu/) with the study accession #10483 and the EMBL ENA database (http://www.ebi.ac.uk/ena) with the study accession #ERP019564.

Example 1

Gut Microbes Promote Motor and GI Dysfunction

This example demonstrates that gut microbes promote motor and GI dysfunction using ASO animals harboring a complex microbiota and wild-type animals.

The Thy1-αSyn (alpha-synuclein-overexpressing [ASO]) mouse displays progressive deficits in fine and gross motor function, as well as gut motility defects. Evidence has linked unregulated αSyn expression in humans to a higher risk of PD, providing an epidemiological foundation for the Thy1-αSyn mouse model. Defects in coordinated motor tasks become evident at 12 weeks of age. Motor function was measured via four tests: beam traversal, pole descent, nasal adhesive removal, and hindlimb clasping reflexes, as previously validated in this model (as described in Fleming et al., 2004, Early and progressive sensorimotor anomalies in mice overexpressing wild-type human alpha-synuclein. J. Neurosci. 24, 9434-9440, the content of which is incorporated herein in its entirety).

Figure 2A:
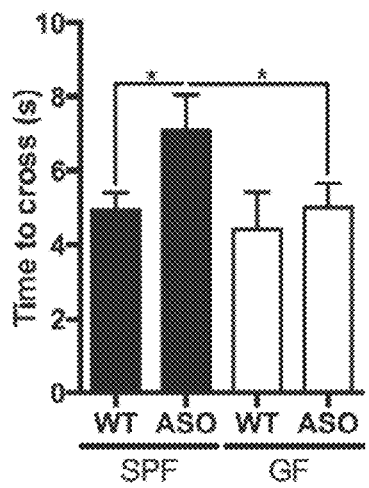
FIGS. 2A-2F show that gut microbes promote motor and gastrointestinal dysfunction. Animals were tested at 12-13 weeks of age. n=4-6, error bars represent the mean and standard error from three trials per animal. Data are representative of two experiments. *$p \le 0.05$; $p \le 0.01$; *$p \le 0.001$; ****$p \le 0.0001$. Abbreviations: SPF, specific-pathogen-free; GF, germ-free; WT, wild-type; ASO, Thy1-α-synuclein genotype.
Figure 2B:
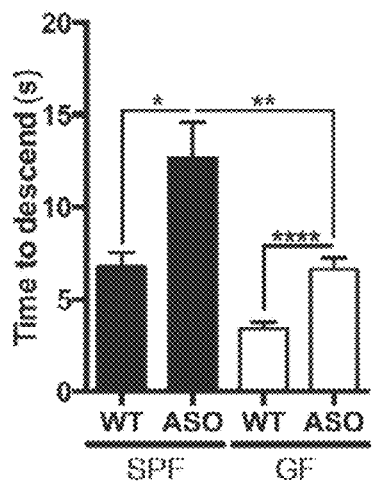
Figure 2E:
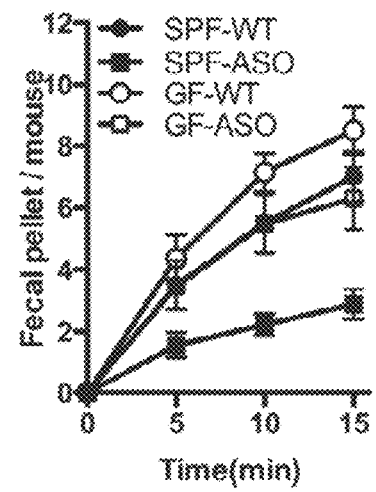
Figure 2C:
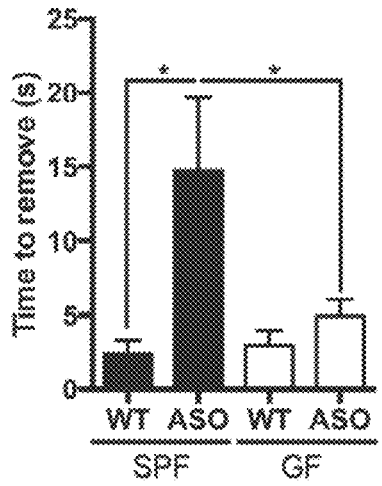
Figure 2D:
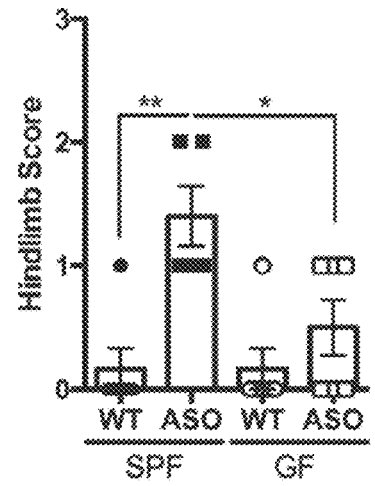
Figure 2F:
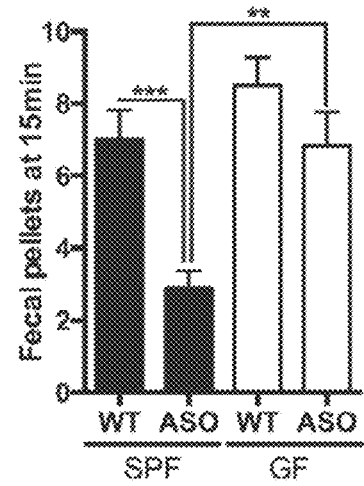

12- to 13-week-old ASO animals harboring a complex microbiota (SPF-ASO) required significantly more time to cross a challenging beam compared to wild-type littermates (SPF-WT) and also exhibited increased time to descend a pole, two measures of gross motor function (FIGS. 2A and 2B). Removal of an adhesive from the nasal bridge, a test of fine motor control, was impaired in SPF-ASO mice compared to SPF-WT mice (FIG. 2C). The hindlimb clasping reflex, a measure of striatal dysfunction, was defective in SPF-ASO mice (FIG. 2D).

Figure 3G:
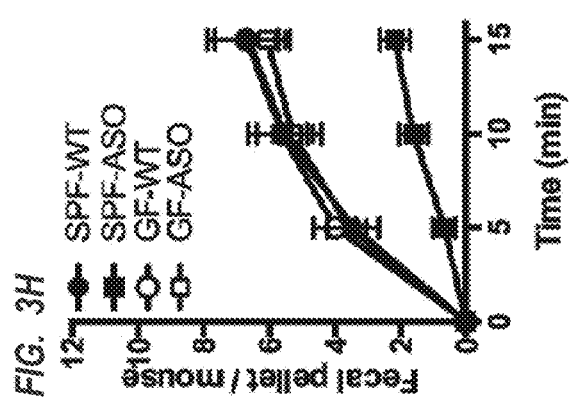
Figure 3I:
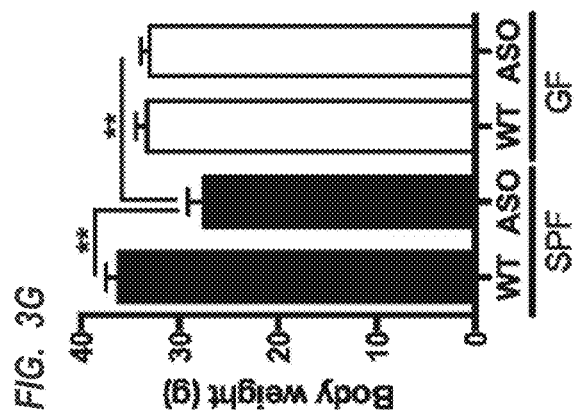
Figure 3H:
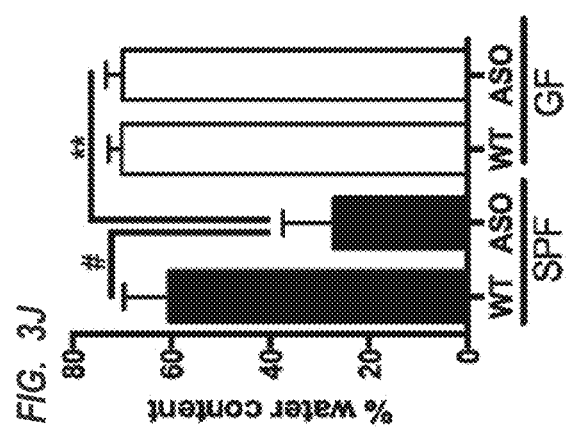

To assess the contribution of gut bacteria, ASO mice (GF-ASO) and wild-type mice (GF-WT) were re-derived under germ-free conditions. Unexpected, 12- to 13-week-old GF-ASO animals exhibit reduced deficits in beam traversal, pole descent, adhesive removal, and hindlimb clasping (FIGS. 2A-2D). In fact, the execution of motor function tasks by GF-ASO mice resembled performance levels of WT animals in many cases. GF-ASO mice did not exhibit differences in weight compared to SPF-ASO animals (FIG. 3A), while both SPF-ASO and GF-ASO animals displayed defects in the inverted grid assay, a measure of limb strength (FIG. 3B). Thus, outcomes in motor tests were not due to weight or physical strength.

At a later age (24-25 weeks old), SPF-ASO animals exhibited a progressive decline in motor function (FIGS. 3C-3G), which was significantly delayed in GF-ASO animals (FIGS. 3C-3G). Consistent differences in motor tasks between GF-WT and SPF-WT animals were not observed, providing evidence for gene-microbiome interactions. As in PD, motor dysfunction in this mouse model co-occurred with decreased GI function and constipation.

Figure 3J:
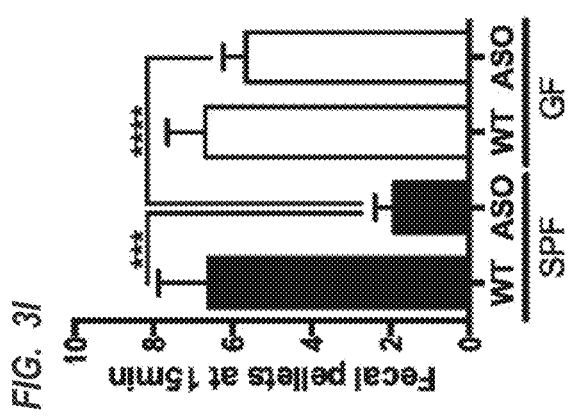
Figure 3K:
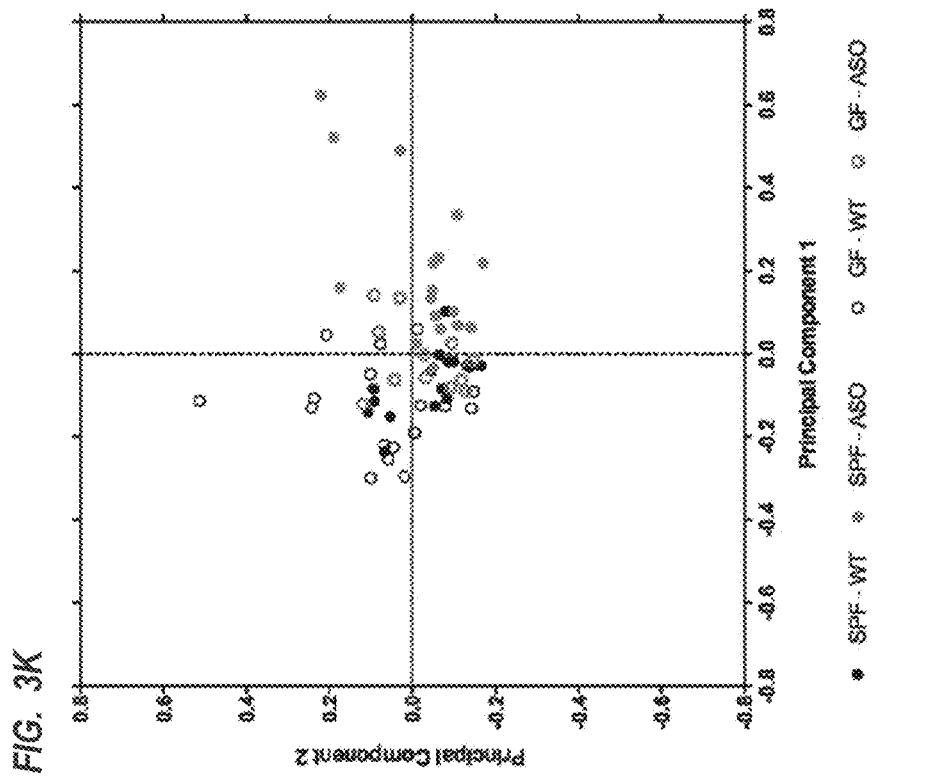

In SPF-ASO animals, a marked decrease in the total output of fecal pellets, at both 12-13 weeks and 24-25 weeks of age, was observed while fecal output was unaltered in GF-ASO animals (FIGS. 2E, 2F, 3H, and 3I). Further, fecal pellets produced by SPF-ASO mice contained reduced water content compared to GF-ASO mice (FIG. 3J), together revealing reduced GI defects in GF animals. Indeed, compilation of all motor phenotypes into a principal-component analysis (PCoA) displayed a striking segregation by the SPF-ASO group, while GF-ASO animals clustered more similarly to WT mice (FIG. 3K).

The data presented in Example 1 demonstrate that the presence of gut microbes promote the hallmark motor and intestinal dysfunction in a preclinical model of PD.

Example 2

The Gut Microbiota is Required for αSyn Pathology

This example demonstrates that αSyn pathology is increased in mice harboring a gut microbiota.

Figure 5G:
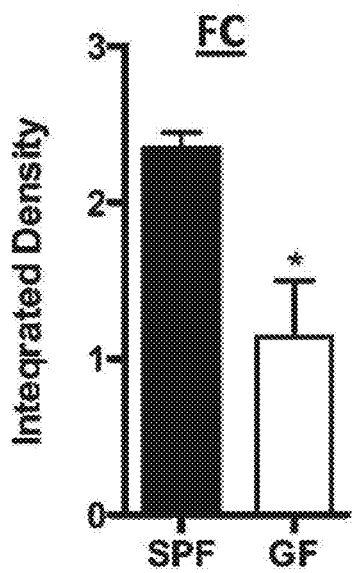
Figure 5H:
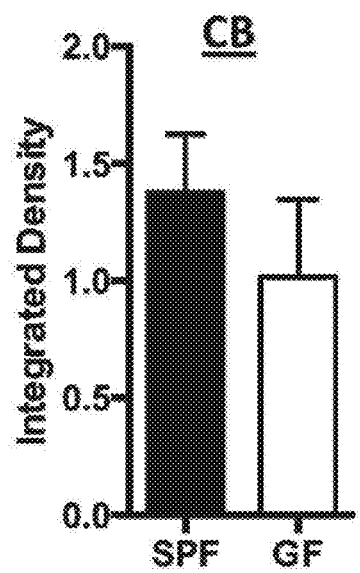

Motor deficits in PD coincide with the aggregation of αSyn. Utilizing an antibody that recognizes only conformation-specific αSyn aggregates and fibrils, immunofluorescence microscopy was performed to visualize αSyn inclusions in the brains of mice. Under SPF conditions, notable aggregation of αSyn in the caudoputamen (CP) and substantia nigra (SN) of ASO animals (FIGS. 4A and 4B), brain regions of the nigrostriatal pathway affected in both mouse models and human PD, was observed. Surprisingly, GF-ASO mice displayed appreciably fewer αSyn aggregates (FIGS. 4A and 4B). To quantify αSyn aggregation, western blots of brain extracts (FIG. 4C) were performed. Significantly less insoluble αSyn in brains of GF-ASO animals was observed (FIGS. 4C-4E). To further confirm these findings, dot blot analysis was performed for aggregated αSyn in the CP and inferior midbrain, where the SN is located. Similarly decreased αSyn aggregation in GF-ASO animals was observed (FIGS. 5A-5C).

Regional specificity of αSyn aggregation was observed: in the frontal cortex (FC), GF-ASO animals harbor fewer αSyn aggregation than SPF animals, while in the cerebellum (CB), nearly equal quantities of αSyn in SPF and GF mice were observed (FIGS. 5D-5H). To ensure that these findings did not reflect differences in transgene expression, levels of αSyn transcript and protein in the inferior midbrain and the CP between SPF- and GF-ASO animals (FIGS. 4F and 4G) were determined to be similar.

Altogether, these data indicate that the microbiota regulates pathways that promote αSyn aggregation and/or prevent the clearance of insoluble protein aggregates.

Example 3

αSyn-Dependent Microglia Activation by the Microbiota

This example demonstrates αSyn-dependent microglia activation by the microbiota.

Figure 6A:
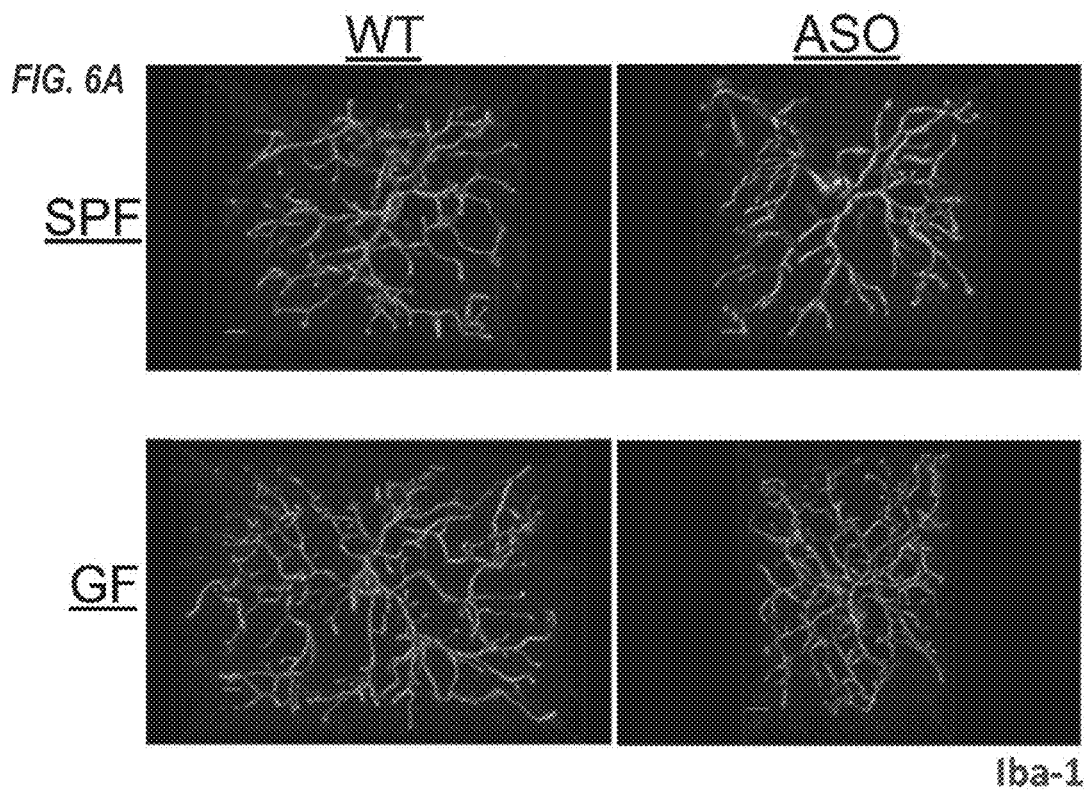
Figure 6B:
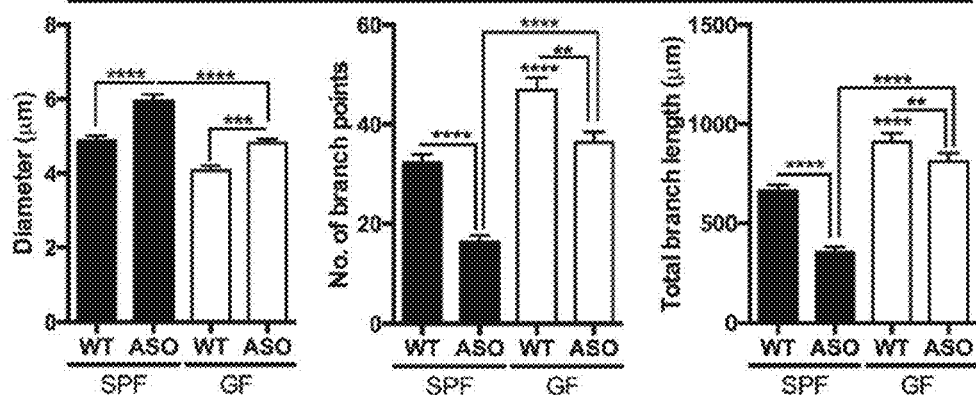
Figure 6C:
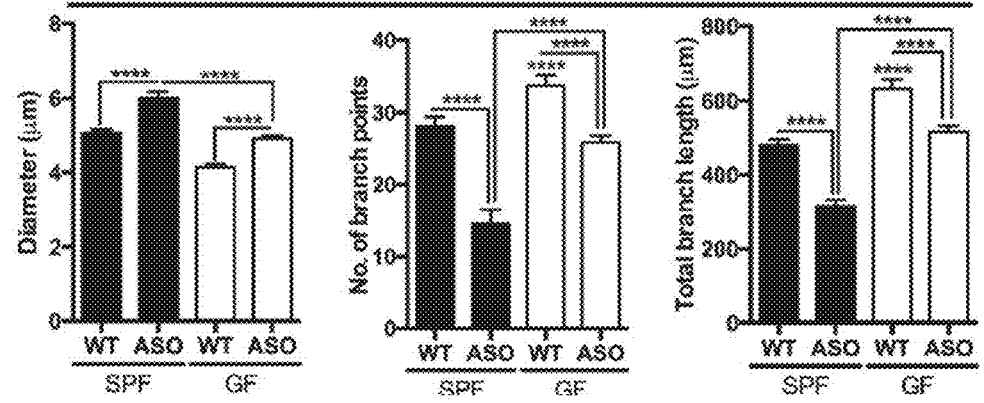

The microbiota modulates immune development in the CNS, and αSyn aggregates activate immune cells, including brain-resident microglia. Microglia undergo significant morphological changes upon activation, transitioning from thin cell bodies with numerous branched extensions to round, amoeboid cells with fewer branches. In situ 3D reconstructions of individual microglia cells from confocal fluorescence microscopy reveals that wild-type GF animals harbor microglia that are distinct from SPF animals. Within the CP and SN, microglia in GF-WT mice displayed increased numbers and total lengths of microglia branches compared to SPF-WT animals (FIGS. 6A-6C). These morphological features are indicative of an arrest in microglia maturation and/or a reduced activation state in GF animals, corroborating a recent report that gut bacteria affect immune cells in the brain.

Extending these observations to a disease model, microglia from SPF-ASO mice displayed significant increases in cell body diameter, along with fewer processes of shorter length compared to GF-ASO mice (FIGS. 6A-6C). Tissue homogenates from the CP and inferior midbrain of SPF-ASO mice contained a marked increase in the pro-inflammatory cytokines tumor necrosis factor-a (TNF-a) and interleukin-6 (IL-6) compared to GF-ASO mice (FIGS. 6D and 6E). Both cytokines are elevated in the brains of PD patients. Gene expression analysis of RNA from enriched CD11b+ cells (primarily microglia) revealed increased Tnfa and Il6 expression in SPF-ASO animals, which was nearly absent in GF animals (FIG. 6F). Neuroprotective Bdnf and the cell cycle marker Ddit4 levels were upregulated in GF animals (FIG. 5I), as observed in previous studies described in, for example, Erny et al., 2015; Matcovitch-Natan et al., 2016. Neuroinflammatory responses were region specific with increased in microglia diameter and TNF-a production in the FC but not the CB (FIGS. 6G and 6H).

Altogether, these findings support the hypothesis that gut microbes promote αSyn-dependent activation of microglia within specific brain regions involved in disease.

Example 4

Postnatal Microbial Signals Modulate αSyn-Dependent Pathophysiology

This example demonstrates postnatal microbial signals modulate αSyn-dependent pathophysiology.

Figure 7A:
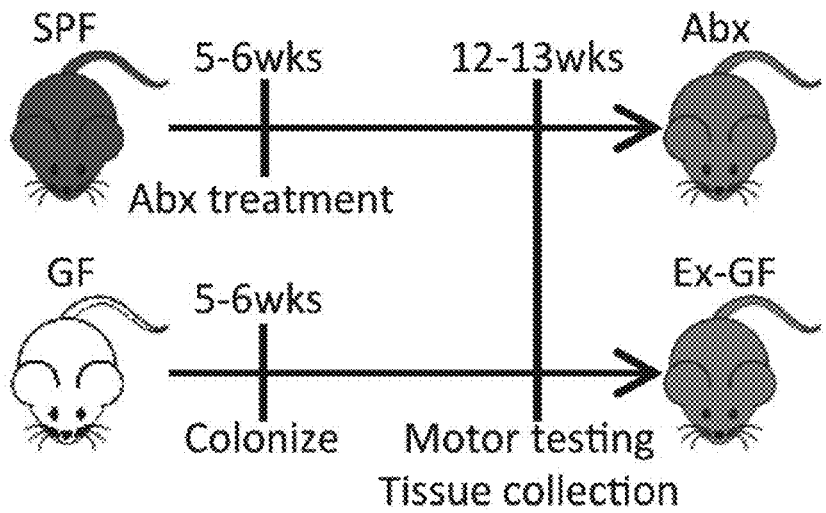
Figure 7B:
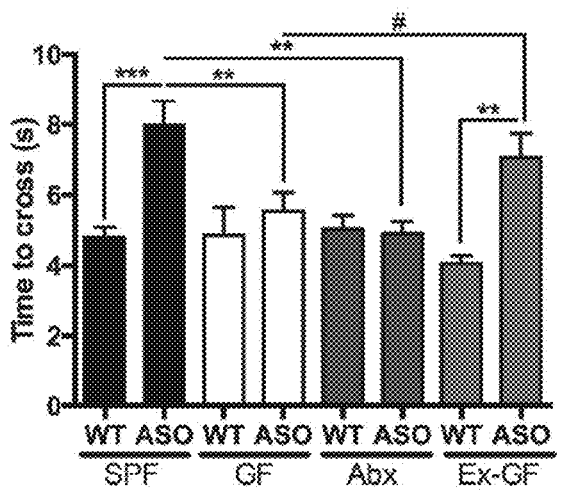
Figure 7C:
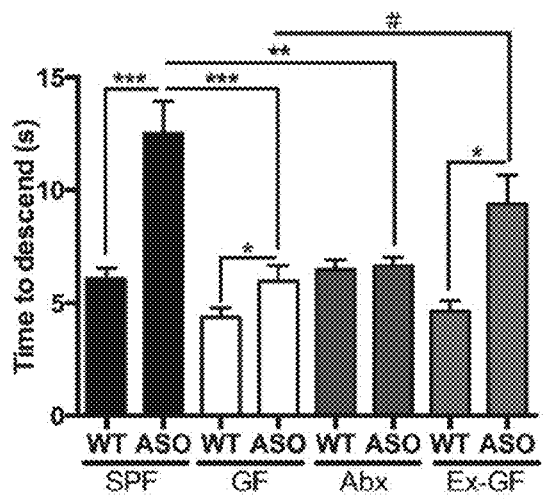
Figure 7D:
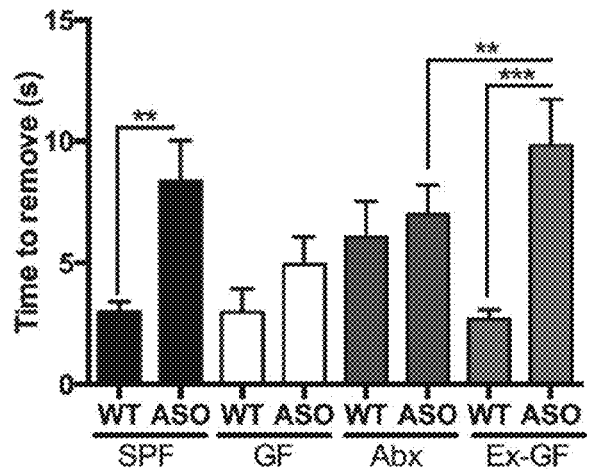
Figure 7E:
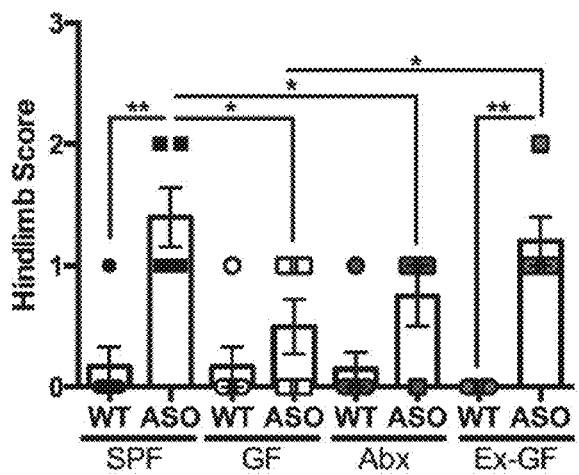

The microbiota influence neurological outcomes during gestation, as well as via active gut-to-brain signaling in adulthood. In order to differentiate between these mechanisms, SPF animals were treated with an antibiotic cocktail to postnatally deplete the microbiota (FIG. 7A). Conversely, groups of 5- to 6-week-old GF mice were colonized with a complex microbiota from SPF-WT animals (FIG. 7A). Remarkably, antibiotic-treated (Abx) animals displayed little αSyn-dependent motor dysfunction, closely resembling mice born under GF conditions (FIGS. 7B-7E). Postnatal colonization of previously GF animals (Ex-GF) recapitulated the genotype effect observed in SPF mice, with mice that overexpressed αSyn displaying significant motor dysfunction (FIGS. 7B-7E).

GI function, as measured by fecal output, was also significantly improved in Abx-treated animals, while Ex-GF mice exhibit an αSyn-dependent decrease in total fecal output (FIGS. 7F and 7G). Furthermore, in the transgenic ASO line, microglia from Ex-GF animals had increased cell body diameters comparable to those in SPF mice (FIGS. 7H and 7I). Abx-ASO animals, however, harbored microglia with diameters similar to GF animals (FIGS. 7H and 7I).

Altogether, these data indicate that while not excluding a role for the microbiota during prenatal neurodevelopment, modulation of microglia activation during adulthood contributes to αSyn-mediated motor dysfunction and neuroinflammation, suggesting active gut-brain signaling by the microbiota.

Example 5

SCFAs are Sufficient to Promote αSyn-Mediated Neuroinflammation

This example demonstrates that SCFAs are sufficient to promote αSyn-mediated neuroinflammation.

Gut bacteria may modulate microglia activation during viral infection through production of microbial metabolites, namely short-chain fatty acids (SCFAs). As shown in FIG. 8A, lower fecal SCFA concentrations were observed in GF and Abx-treated animals, compared to SPF mice. To see whether SCFAs impact neuroimmune responses in a mouse model of PD, GF-ASO and GF-WT animals were treated with a mixture of the SCFAs acetate, propionate, and butyrate (while the animals remained microbiologically sterile) and significantly restored fecal SCFA concentrations (FIG. 8A). Within affected brain regions (i.e., CP and SN), microglia in SCFA-administered animals displayed morphology indicative of increased activation compared to untreated mice, and similar to cells from Ex-GF and SPF mice (FIGS. 9A, 9B, 8B, and 8C; see also FIGS. 6A-6H and 7A-7I). Microglia from GF-ASO mice fed SCFAs (SCFA-ASO) were significantly larger in diameter than those of GF-WT animals treated with SCFAs (SCFA-WT), with a concomitant decrease in the length and total number of branches. Abx-treated animals, however, displayed microglia morphology similar to GF animals (FIGS. 9B, 8B and 8C; see also FIGS. 6A-6H and 7A-7I). Changes in microglia diameter were also observed in the FC, but not the CB, demonstrating region-specific responses (FIGS. 8D and 8E).

Figure 10A:
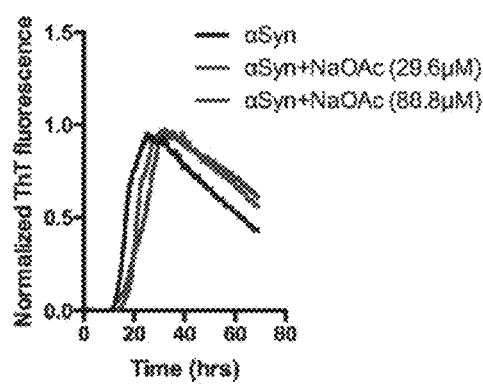
FIGS. 10A-10M show that SCFAs do not directly alter αSyn aggregation (related to FIGS. 9A-9H). Animals were tested at 12-13 weeks of age. N=6-12, error bars represent the mean and standard error from 3 trials per animal. Data were compiled from 2 independent cohorts and plotted with controls from FIGS. 7A-7I for clarity. *$p≤0.05$; $p≤0.01$; *$p≤0.001$; ****$p≤0.0001$. Abbreviations: SPF=specific pathogen free; GF=germ-free; HK=heat-killed bacteria-treated; WT=wild-type, ASO=Thy1-α-synuclein genotype.
Figure 10D:
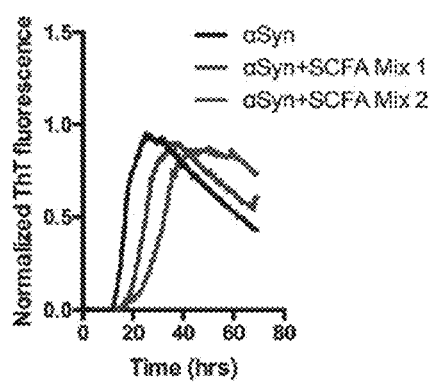
Figure 10B:
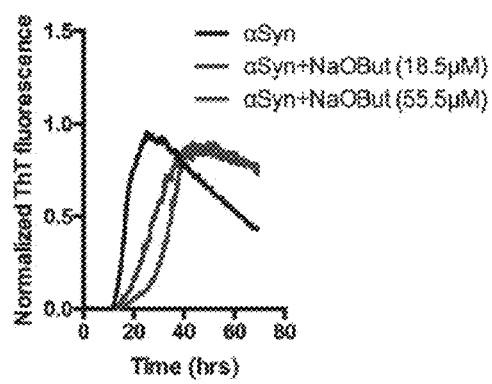
Figure 10E:
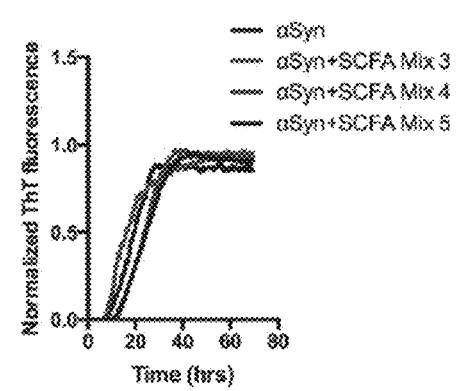
Figure 10C:
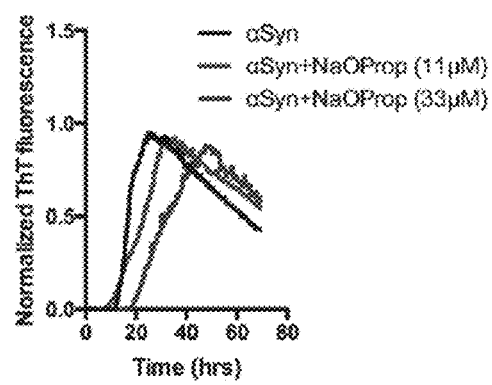
Figure 10F:
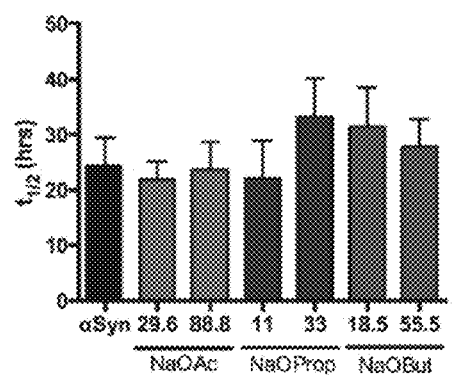
Figure 10G:
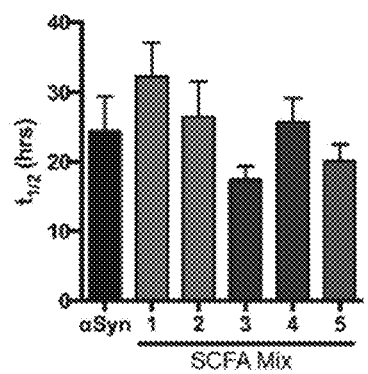
Figure 10H:
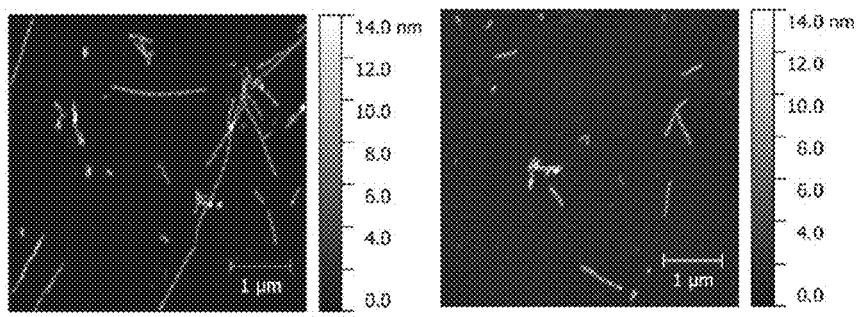
Figure 10I:
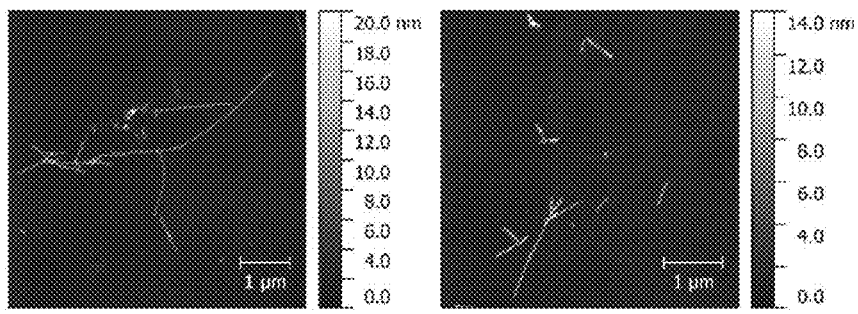
Figure 10J:
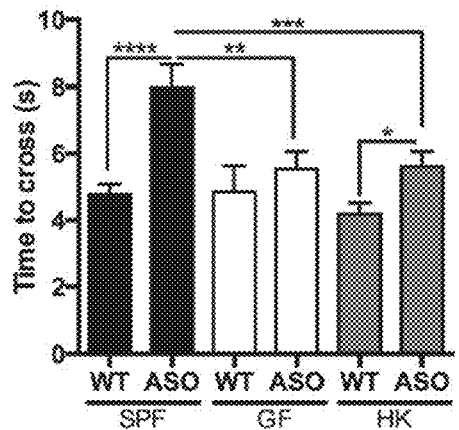
Figure 10K:
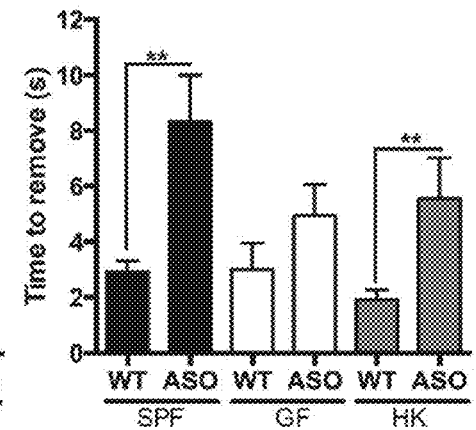
Figure 10L:
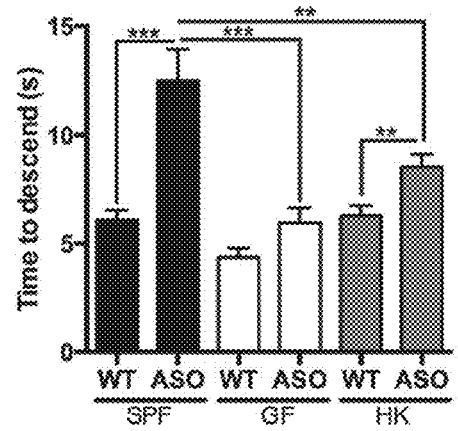
Figure 10M:
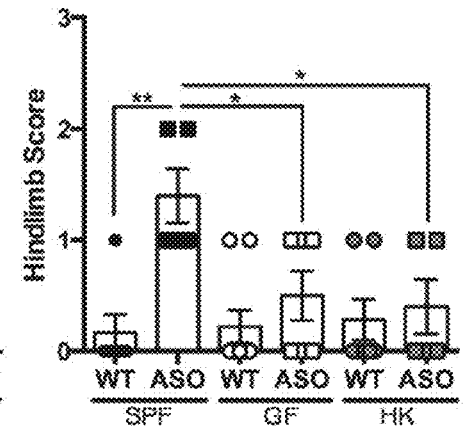
Figure 11A:
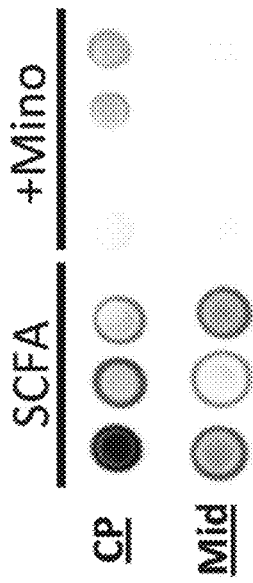
Figure 11B:
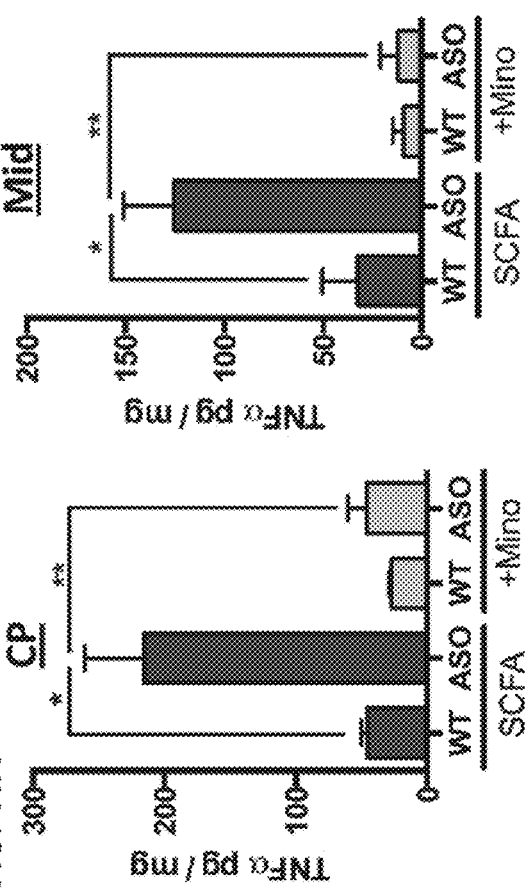
Figure 11C:
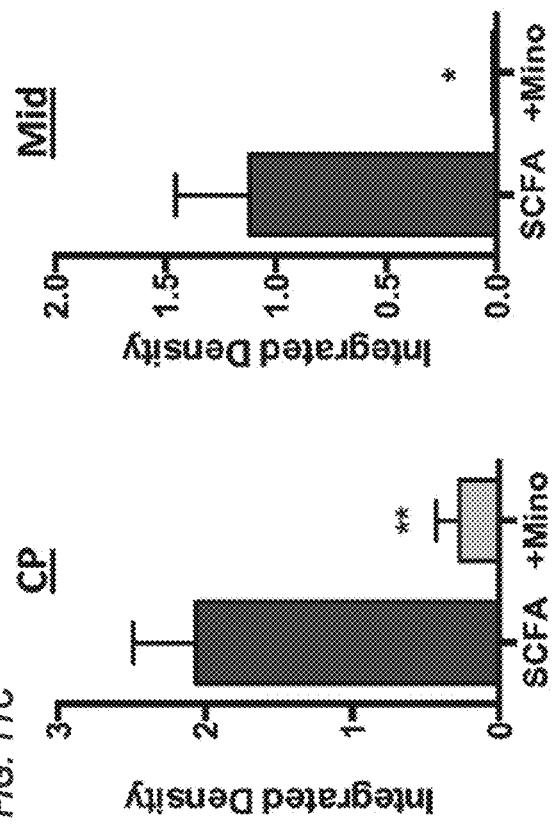

Corresponding to microglia morphology, αSyn aggregated in mice administered SCFAs compared to untreated and Abx-treated mice, and similar to Ex-GF animals (FIGS. 8F-8I). Strikingly, postnatal signaling by microbes was observed to induce increased αSyn aggregation in the CP and SN (FIGS. 8F and 8G), with no observable difference in the FC and CB (FIGS. 8H and 8I), confirmed by quantification and western blot (FIGS. 8J-8O). SCFAs either singly or in a mixture, over a range of concentrations, did not expedite the aggregation of human αSyn in vitro (FIGS. 10A-10G), nor did they alter the overall structure of αSyn amyloid fibrils (FIGS. 10H and 10I).

Altogether, these data indicate that SCFAs accelerate in vivo αSyn aggregation, albeit independently of direct molecular interactions.

Example 6

SCFAs are Sufficient to Promote Motor Deficits

This example demonstrates that SCFAs promote αSyn-stimulated microglia activation and motor dysfunction.

To explore a link between microbial metabolites and motor symptoms in the Thy1-αSyn model, GF animals were treated with the SCFA mixture beginning at 5-6 weeks of age, and motor function was assessed at 12-13 weeks of age. SCFA-ASO mice displayed significantly impaired performance in several motor tasks compared to untreated GF-ASO animals (FIGS. 9C-9F), including impairment in beam traversal, pole descent, and hindlimb reflex (compare GF-ASO to SCFA-ASO mice). All effects by SCFAs were genotype specific to the Thy1-αSyn mice. GI deficits were also observed in the SCFA-treated transgenic animals (FIGS. 9G and 9H). Oral treatment of GF animals with heat-killed bacteria did not induce motor deficits (FIGS. 10J-10M), suggesting that bacteria need to be metabolically active. Additionally, oral treatment of SCFA-fed animals with the anti-inflammatory compound minocycline was sufficient to reduce TNF-a production, reduce αSyn aggregation, and improve motor function, without altering transgene expression (FIGS. 11A-11H).

Altogether, these data indicate that the microbiota actively produce metabolites, such as SCFAs, are required for microglia activation and αSyn aggregation, contributing to motor dysfunction in a preclinical model of PD.

Example 7

Dysbiosis of the PD Microbiome

This example demonstrates dysbiosis of the PD microbiome.

PD patients have been found to display altered microbiomes. In this example, fecal samples from six human subjects diagnosed with PD as well as six matched healthy controls were collected (Table 2) to determine whether human gut microbes affect disease outcomes when transferred into GF mice. To limit confounding effects, only new-onset, treatment-naive PD patients with healthy intestinal histology were chosen, among other relevant inclusion and exclusion criteria (Table 2).

TABLE 2

Demographics of Human Donors, PD and Healthy Controls (related to FIGS. 12A-12E and 14A-14G). Demographic data of fecal donors for each PD and healthy donor pair.

| Pair | ID | Disease Duration | UPDRS | HY stage | Constipation duration | Constipation severity scale | Constipation Before or After PD Diagnosis | Gender | Age | Race | BMI | Medications |
|---|---|---|---|---|---|---|---|---|---|---|---|---|
| 1 | PD1 | 4 | 28 | 2 | 1.5 | 1 | After | Male | 55 | Caucasian | 25.7 | None |
| 1 | HC1 | n/a | n/a | n/a | n/a | n/a | n/a | Male | 57 | Caucasian | 36 | None |
| 2 | PD2 | 1 | 27 | 2 | n/a | n/a | n/a | Male | 66 | Caucasian | 27.3 | Aspirin 81 mg/d |
| 2 | HC2 | n/a | n/a | n/a | n/a | n/a | n/a | Male | 61 | Caucasian | 28.6 | None |
| 3 | PD3 | 2 | 27 | 2 | n/a | n/a | n/a | Male | 57 | Caucasian | 23.7 | Sertraline 150 mg/d; BuproprionXL 300 mg/d |
| 3 | HC3 | n/a | n/a | n/a | n/a | n/a | n/a | Male | 55 | Caucasian | 26.8 | None |
| 4 | PD4 | 2 | 16 | 1 | 5 | 2 | Before | Female | 46 | Caucasian | 26.6 | None |
| 4 | HC4 | n/a | n/a | n/a | n/a | n/a | n/a | Female | 50 | African American | 28.6 | None |
| 5 | PD5 | 8 | 18 | 2 | n/a | n/a | n/a | Male | 49 | Caucasian | 27.5 | None |
| 5 | HC5 | | | | | | | Male | 43 | Caucasian | 29 | None |
| 6 | PD6 | 1 | 15 | 1.5 | 30 | 7 | Before | Female | 56 | Caucasian | 22 | Ranitidine 150 mg/d |
| 6 | HC6 | n/a | n/a | n/a | n/a | n/a | n/a | Female | 57 | Caucasian | 22 | None |

UPDRS = unified Parkinson's disease rating scale;
HY stage = Hoehn and Yahr scale;
BMI = body mass index.

Figure 12B:
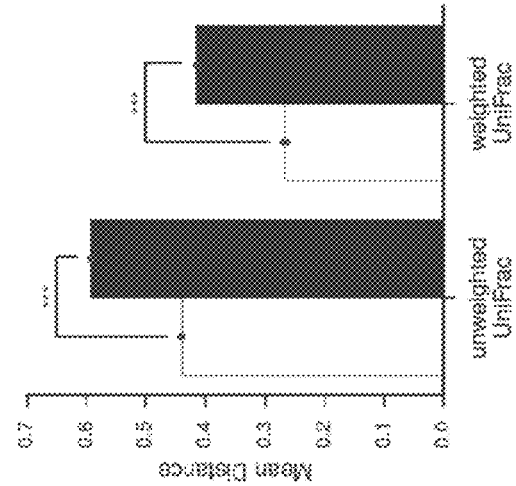
FIG. 12A-12E shows microbiome dysbiosis of PD patient samples after transplant into germ-free mice. n=3-6, over 3 time points post-colonization. Error bars represent the mean and standard error. $*p\leq0.001$, 999 permutations. Abbreviations: HC, germ-free mice colonized with fecal microbes from healthy controls; PD, germ-free mice colonized with fecal microbes from Parkinson's disease patients; WT, wild-type; ASO, Thy1-α-synuclein genotype. See also FIGS. 13A-13E.
Figure 12D:
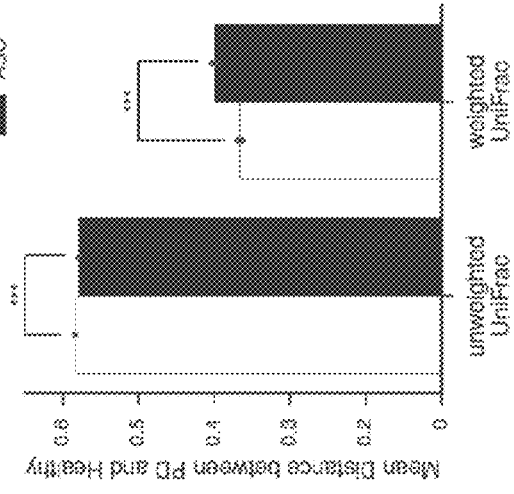
Figure 12A:
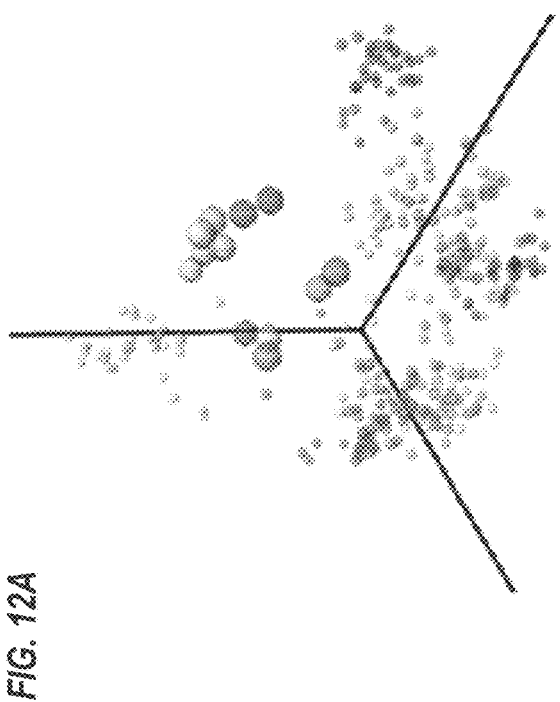
Figure 12C:
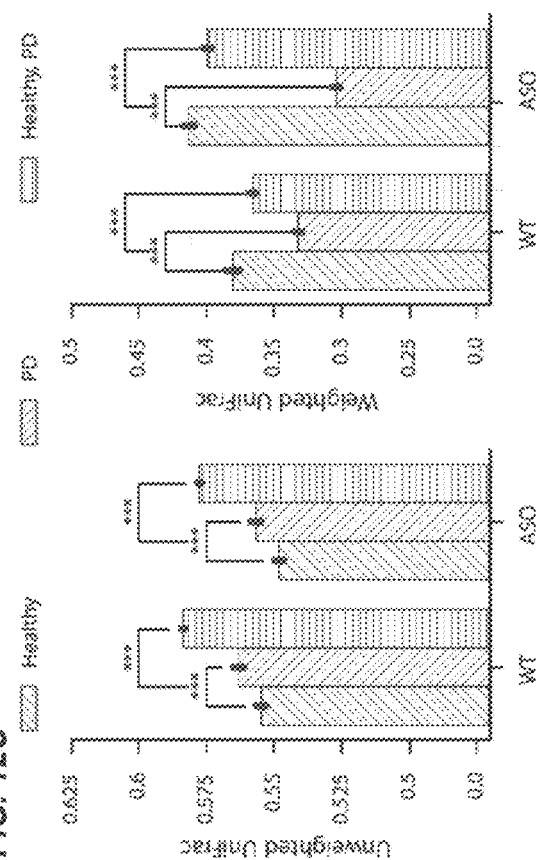
Figure 12E:
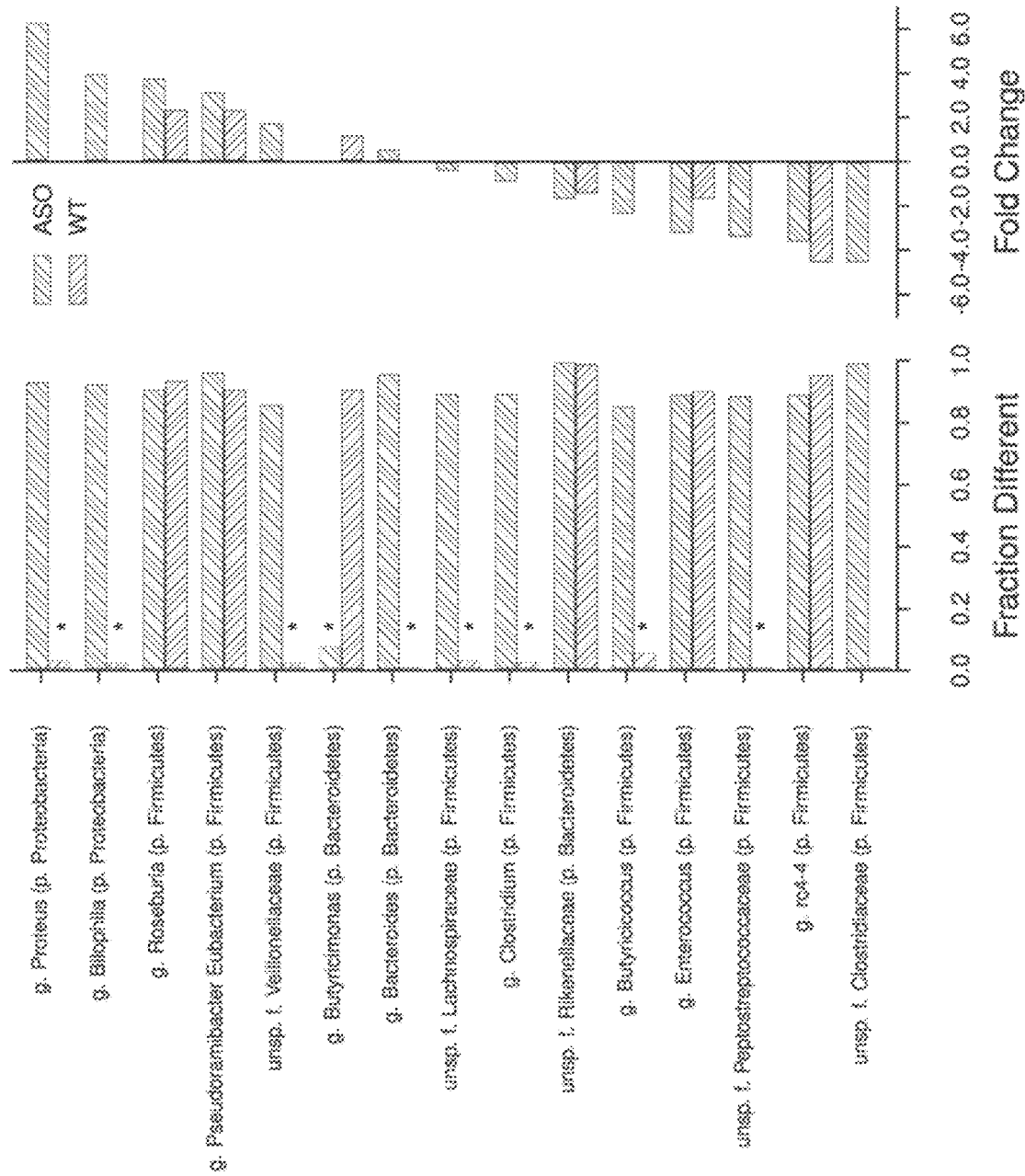

Fecal microbiota from PD patients or controls were transplanted into individual groups of GF recipient animals via oral gavage. Fecal pellets were collected from "humanized" mice, bacterial DNA was extracted, and 16S rRNA sequencing was performed. Sequences were annotated into operational taxonomic units (OTUs), using closed reference picking against the Greengenes database and metagenome function was predicted by PICRUSt. Recipient animal groups were most similar to their respective human donor's profile in unweighted UniFrac (Lozupone and Knight, 2005), based on PCoA (FIGS. 12A and 12B). Strikingly, the disease status of the donor had a strong effect on the microbial communities within recipient mice. Humanized mouse groups from PD donors were significantly more similar to each other than to communities transplanted from healthy donors, with this trend persisting when stratified by genetic background (FIGS. 12C and 12D). Furthermore, there were significant differences between the healthy and PD donors in the ASO background compared to wildtype (WT) recipients, suggesting genotype effects on microbial community configuration (FIGS. 12C and 12D).

Figure 13A:
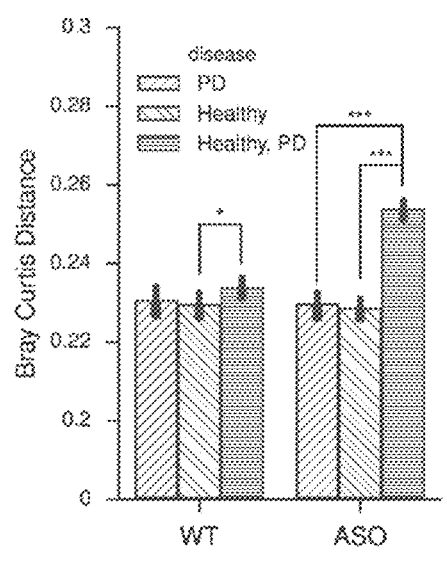
FIGS. 13A-13E show that microbial metabolic pathways were altered in humanized animals (related to FIGS. 12A-12E). N=3-6, over 3 time points post-colonization for KEGG analysis, N=21-24 for SCFA abundances. Error bars represent the mean and standard error. $*p:<; 0.05$; $p:<; 0.01$; $*p:<; 0.001$.
Figure 13B:
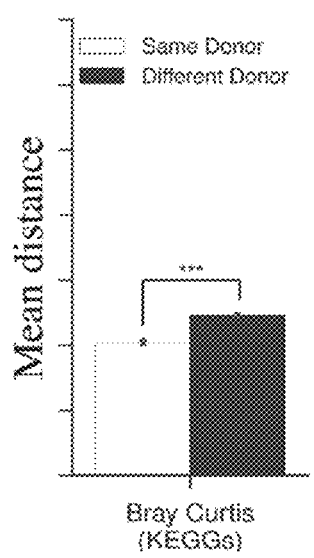
Figure 13C:
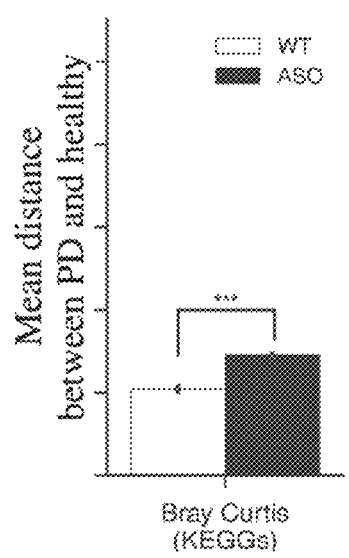
Figure 13:
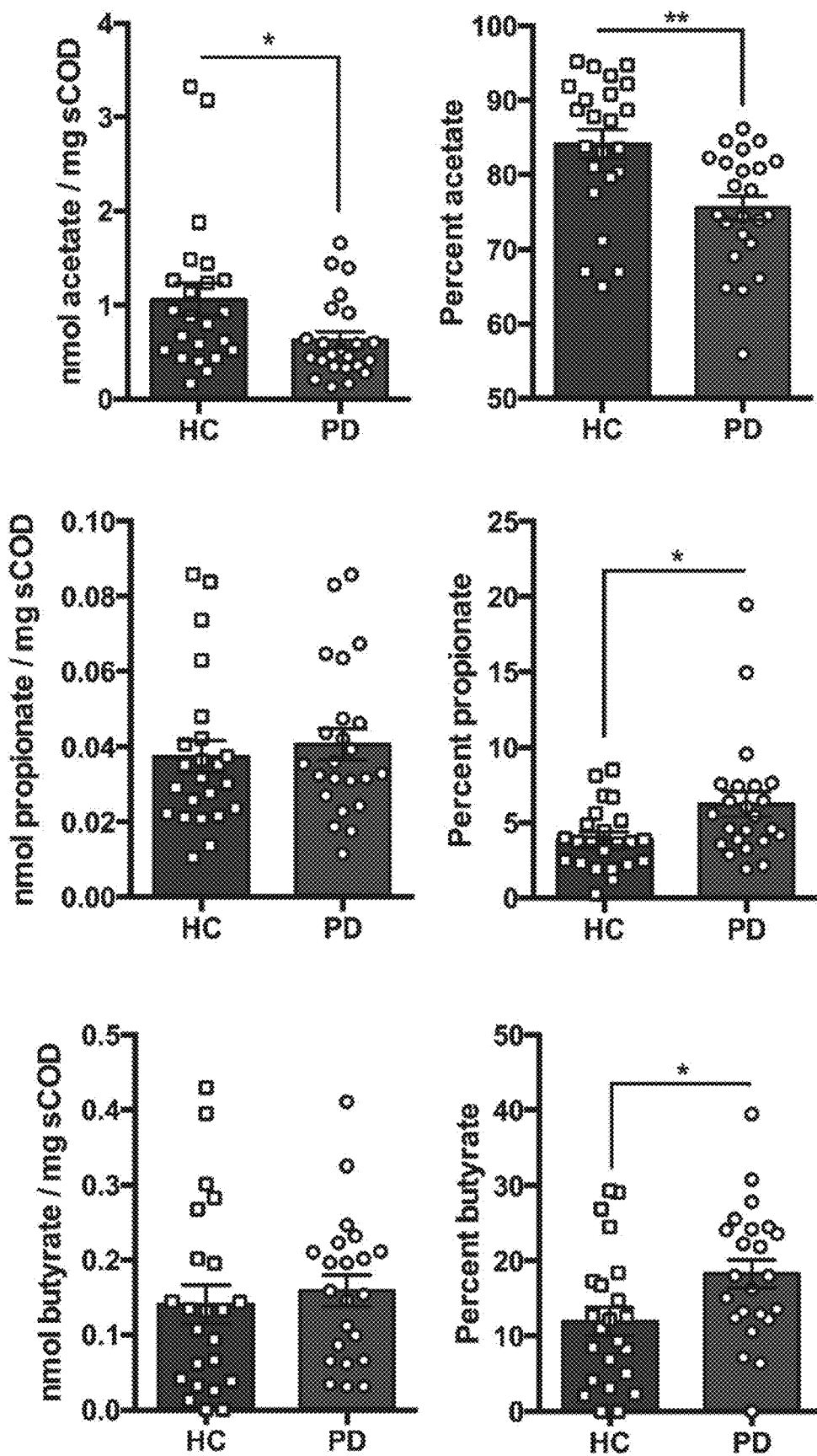

A number of genera that were altered in animals colonized with microbiota derived from PD donors, compared to healthy controls (FIG. 12E), as well as altered KEGG pathways between these groups as indicated by Bray-Curtis distances (FIGS. 13A-13C), were identified. OTUs increased in abundance in mice with PD microbiomes include *Proteus* sp., *Bilophila* sp., and *Roseburia* sp., with a concomitant loss of members of families Lachnospiraceae, Rikenellaceae, and Peptostreptococcaceae, as well as *Butyricicoccus* sp. (FIG. 13E). Interestingly, some taxa were altered only in ASO animals (e.g., *Proteus* sp., *Bilophila* sp., and Lachnospiraceae), while others displayed significant changes independent of mouse genotype (e.g., *Rosburia* sp., Rikenellaceae, and *Enterococcus* sp.) (FIG. 13E). Intriguingly, the abundance of three SCFA-producing KEGG families (K00929, butyrate kinase, and K01034 and K01035, acetate CoA/acetoacetate CoA transferase alpha and beta) were increased in mice that received fecal microbes derived from PD donors (FIG. 13D). Further, animals receiving PD donor-derived microbiota displayed a significantly altered SCFA profile, with a lower concentration of acetate and higher relative abundances of propionate and butyrate, compared to animals colonized with microbes from healthy controls (FIG. 13E).

Altogether, these data indicate that differences in fecal microbial communities between PD patients and controls can be maintained after transfer into mice. Further, αSyn overexpression engenders distinct alterations to the gut microbiome profile after transplantation.

Example 8

PD-Derived Gut Microbiota Promotes Motor Dysfunction

This example demonstrates PD-derived gut microbiota promotes motor dysfunction.

Figures 14C, 14D:
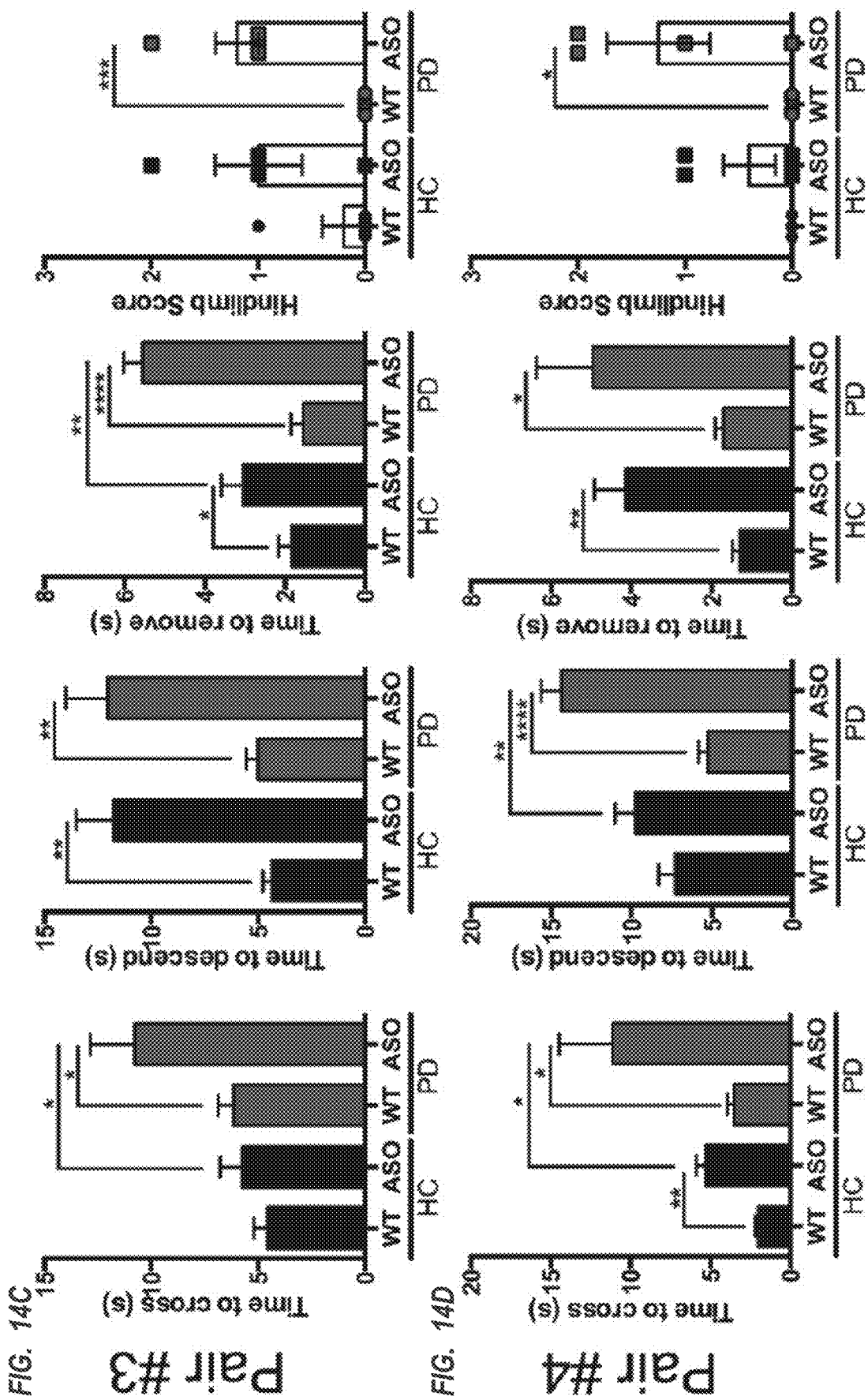
Figure 14G:
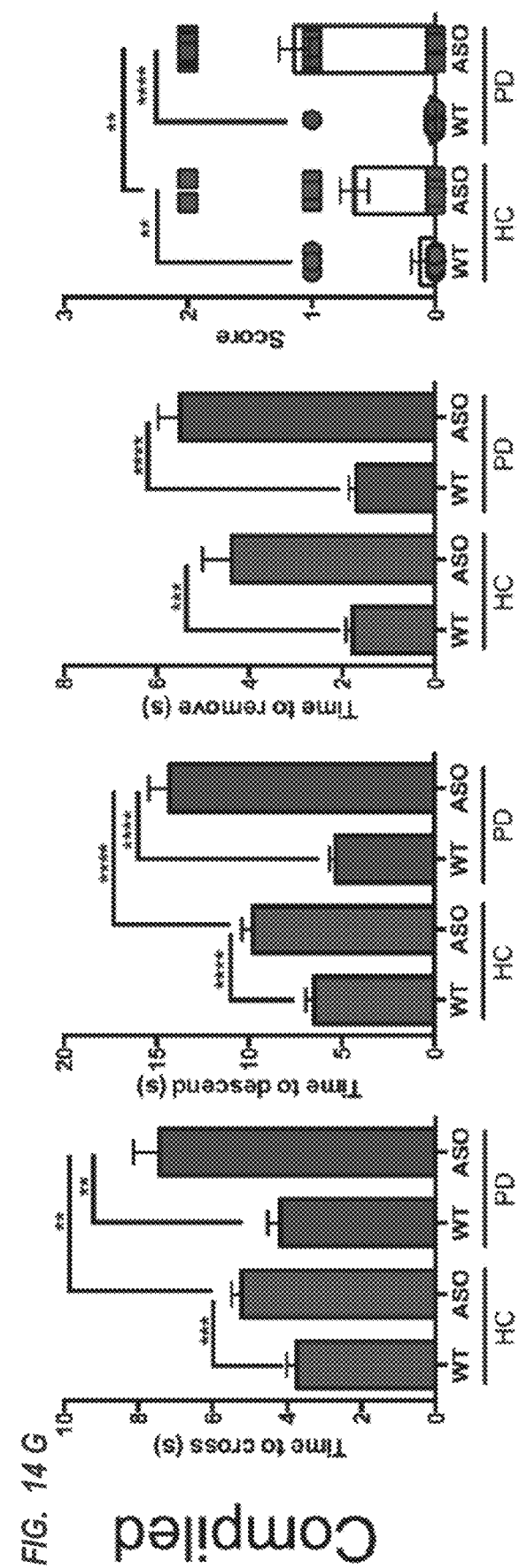

To assess microbiota function, groups of humanized animals from each of the donor pairs were tested for motor function. Consistent among four of the six pairs (pairs #1, 3, 4, and 5), microbiota derived from individuals with PD promoted increased αSyn-mediated motor dysfunction (FIGS. 14A-14F). Beam traversal, pole descent, and nasal adhesive removal were significantly impaired in ASO animals colonized with PD microbiota compared to genotype-matched recipient mice harboring gut bacteria from healthy controls. Hindlimb reflex scores, on the other hand, were generally not different between individual donors. Interestingly, microbiota from one pair of samples did not induce significant genotype effects in the beam traversal and pole descent tasks (pair #2, FIG. 14B), reflecting potential heterogeneity in the population that needs to be addressed through well-powered cohort studies. No notable effects in motor function by WT recipient animals colonized with microbiota from either donor group were observed (FIGS. 14A-14F). This finding in a preclinical mouse model indicates that the PD microbiota contributes to disease symptoms in genetically susceptible hosts. Also, recipient animals displayed little alteration to weight and GI function as measured by fecal output (FIGS. 15A-15F). Compilation of performance data from all groups revealed that microbiota from PD patients induced increased motor impairment in ASO animals compared to microbes from healthy controls in three of four tests used in this study (FIG. 14G). In fact, depicting all motor function by PCoA displayed striking global differences between animals colonized with microbiota from PD donors, compared to those colonized with gut bacteria derived from healthy individuals (FIG. 15G).

Altogether, these data that gut bacteria from PD patients compared to healthy controls enhance motor deficits in a mouse model provides evidence for a functional contribution by the microbiota to synuclienopathies.

As described herein, the intestinal microbiota influence neurodevelopment, modulate behavior, and contribute to neurological disorders. Without being bound by any particular theory, it is believed that there is a functional link between gut bacteria and neurodegenerative diseases remains unexplored. Synucleinopathies are characterized by aggregation of the protein α-synuclein (αSyn), often resulting in motor dysfunction as exemplified by Parkinson's disease (PD). As shown in Examples 1-8, using mice that overexpress αSyn, gut microbiota are found to be required for motor deficits, microglia activation, and αSyn pathology. Antibiotic treatment ameliorates, while microbial re-colonization promotes, pathophysiology in adult animals, suggesting that postnatal signaling between the gut and the brain modulates disease. Oral administration of specific microbial metabolites to germ-free mice promotes neuroinflammation and motor symptoms. In addition, colonization of αSyn-overexpressing mice with microbiota from PD-affected patients enhances physical impairments compared to microbiota transplants from healthy human donors. These findings indicate that gut bacteria regulate movement disorders in mice and alterations in the human microbiome represent a risk factor for PD.

Example 9

Treatment of Parkinson's Disease (PD)

This example illustrates the treatment of a patient suffering from PD.

The rate of α-Syn aggregation, or the level of α-Syn aggregation (e.g., the amount of α-Syn aggregate), or both in a subject is determined. The abnormal rate of α-Syn aggregation, or level of α-Syn aggregation (e.g., the amount of α-Syn aggregate), or both in the subject is indicative that the subject has PD. The composition of gut microbiota in the subject is adjusted. It is expected that the adjustment in gut microbiota composition in the subject will relieve one or more symptoms of PD, such as improve one or more motor deficits, in the subject.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of reducing neuroinflammation in a subject having a disease, the method comprising:
   administering a composition comprising an inhibitor of a short chain fatty acid (SCFA) comprising propionate or butyrate; and
   increasing a level of a Parkinson's disease (PD)-protective bacteria in a gut microbiota of the subject; or
   decreasing a level of a PD-enhancing bacteria in a gut microbiota of the subject,
   wherein increasing the level of the PD-protective bacteria or decreasing the level of the PD-enhancing bacteria reduces neuroinflammation in the subject,
   wherein the PD-protective bacteria is Lachnospiraceae, *Rikenellaceae, Peptostreptococcaceae*, or *Butyricicoccus* and
   wherein the PD-enhancing bacteria belongs to *Proteus* species, *Bilophila* species, *Roseburia* species, *Pseudoramibacter Eubacterium*, or *Veillonellaceae* family.

2. The method of claim 1, wherein the disease is a neurodegenerative disease.

3. The method of claim 1, wherein the disease is PD, dementia with Lewy body disease, or multiple system atrophy.

4. The method of claim 1, wherein increasing the level of the PD-protective bacteria in the gut microbiota of the subject comprises introducing gut microbiota from a healthy subject to the subject.

5. The method of claim 4, wherein introducing gut microbiota from a healthy subject comprises fecal transplantation, microbiota conventionalization, microbial colonization, reconstitution of gut microbiota, probiotic treatment, or a combination thereof.

6. The method of claim 1, further comprising administering one or more antibiotics to the subject.

7. The method of claim 6, wherein the one or more antibiotics comprise ampicillin, vancomycin, neomycin, gentamycin, erythromycin, or any combination thereof.

8. The method of claim 1, wherein reducing neuroinflammation comprises reducing TNF-α production, reducing interleukin-6 (IL-6), or reducing αSyn aggregation.

9. The method of claim 2, wherein reducing neuroinflammation comprises reducing microglia activation in the subject.

10. The method of claim 2, further comprising identifying the subject as having a disease when the subject has an abnormal level of aggregation of α-synuclein (αSyn).

11. The method of claim 10, further comprising measuring a rate and/or level of αSyn aggregation in the brain of the subject, the clearance rate and/or level of insoluble αSyn protein aggregate in the brain of the subject, or a combination thereof.

12. The method of claim 1, wherein the composition further comprises a pharmaceutically acceptable carrier.

13. The method of claim 2, wherein the composition is formulated for oral administration.

14. The method of claim 1, wherein the method further comprises:
   administering a composition comprising an inhibitor of a short chain fatty acid (SCFA) comprising propionate or butyrate;
   increasing a level of a Parkinson's disease (PD)-protective bacteria in a gut microbiota of the subject; and
   decreasing a level of a PD-enhancing bacteria in a gut microbiota of the subject,
   wherein increasing the level of the PD-protective bacteria and decreasing the level of the PD-enhancing bacteria reduces neuroinflammation in the subject.

* * * * *

SEQUENCE LISTING

```
Sequence total quantity: 12
SEQ ID NO: 1            moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 1
ttgcagcagc cactggcttt g                                                    21

SEQ ID NO: 2            moltype = DNA  length = 25
FEATURE                 Location/Qualifiers
misc_feature            1..25
                        note = Synthetic oligonucleotide
source                  1..25
                        mol_type = other DNA
                        organism = synthetic construct
SEQUENCE: 2
ggatccacag gcatatcttc cagaa                                                25

SEQ ID NO: 3            moltype = DNA  length = 23
FEATURE                 Location/Qualifiers
misc_feature            1..23
                        note = Synthetic oligonucleotide
```

```
source                     1..23
                           mol_type = other DNA
                           organism = synthetic construct
SEQUENCE: 3
ccctcacact cagatcatct tct                                              23

SEQ ID NO: 4               moltype = DNA   length = 19
FEATURE                    Location/Qualifiers
misc_feature               1..19
                           note = Synthetic oligonucleotide
source                     1..19
                           mol_type = other DNA
                           organism = synthetic construct
SEQUENCE: 4
gctacgacgt gggctacag                                                   19

SEQ ID NO: 5               moltype = DNA   length = 23
FEATURE                    Location/Qualifiers
misc_feature               1..23
                           note = Synthetic oligonucleotide
source                     1..23
                           mol_type = other DNA
                           organism = synthetic construct
SEQUENCE: 5
tagtccttcc tacccaatt tcc                                               23

SEQ ID NO: 6               moltype = DNA   length = 21
FEATURE                    Location/Qualifiers
misc_feature               1..21
                           note = Synthetic oligonucleotide
source                     1..21
                           mol_type = other DNA
                           organism = synthetic construct
SEQUENCE: 6
ttggtcctta gccactcctt c                                                21

SEQ ID NO: 7               moltype = DNA   length = 20
FEATURE                    Location/Qualifiers
misc_feature               1..20
                           note = Synthetic oligonucleotide
source                     1..20
                           mol_type = other DNA
                           organism = synthetic construct
SEQUENCE: 7
caaggcaaga gctgccatag                                                  20

SEQ ID NO: 8               moltype = DNA   length = 19
FEATURE                    Location/Qualifiers
misc_feature               1..19
                           note = Synthetic oligonucleotide
source                     1..19
                           mol_type = other DNA
                           organism = synthetic construct
SEQUENCE: 8
ccggtactta gcgtcaggg                                                   19

SEQ ID NO: 9               moltype = DNA   length = 22
FEATURE                    Location/Qualifiers
misc_feature               1..22
                           note = Synthetic oligonucleotide
source                     1..22
                           mol_type = other DNA
                           organism = synthetic construct
SEQUENCE: 9
tcatacttcg gttgcatgaa gg                                               22

SEQ ID NO: 10              moltype = DNA   length = 19
FEATURE                    Location/Qualifiers
misc_feature               1..19
                           note = Synthetic oligonucleotide
source                     1..19
                           mol_type = other DNA
                           organism = synthetic construct
SEQUENCE: 10
agacctctcg aacctgccc                                                   19

SEQ ID NO: 11              moltype = DNA   length = 20
FEATURE                    Location/Qualifiers
misc_feature               1..20
```

```
                        note = Synthetic oligonucleotide
source                  1..20
                        mol_type = other DNA
                        organism = synthetic construct
SEQUENCE: 11
catggccttc cgtgttccta                                                        20

SEQ ID NO: 12           moltype = DNA  length = 22
FEATURE                 Location/Qualifiers
misc_feature            1..22
                        note = Synthetic oligonucleotide
source                  1..22
                        mol_type = other DNA
                        organism = synthetic construct
SEQUENCE: 12
cctgcttcac caccttcttg at                                                     22
```